(12) United States Patent
Fukui et al.

(10) Patent No.: US 7,906,286 B2
(45) Date of Patent: Mar. 15, 2011

(54) PROBE SET, PROBE CARRIER, AND METHOD FOR DETERMINING AND IDENTIFYING FUNGUS

(75) Inventors: Toshifumi Fukui, Yokohama (JP); Nobuhiro Tomatsu, Yokohama (JP); Nobuyoshi Shimizu, Sakura (JP); Atsushi Takayanagi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 270 days.

(21) Appl. No.: 12/120,177

(22) Filed: May 13, 2008

(65) Prior Publication Data

US 2009/0081666 A1 Mar. 26, 2009

(30) Foreign Application Priority Data

May 14, 2007 (JP) .................................. 2007-128664

(51) Int. Cl.
*C12Q 1/68* (2006.01)
*C07H 21/02* (2006.01)
(52) U.S. Cl. ............................. 435/6; 435/975; 536/23.1
(58) Field of Classification Search ........................ None
See application file for complete search history.

(56) References Cited

U.S. PATENT DOCUMENTS

| | | | |
|---|---|---|---|
| 5,426,027 A | 6/1995 | Lott et al. | |
| 5,512,446 A | 4/1996 | Miyazaki et al. | |
| 5,700,647 A | 12/1997 | Miyazaki et al. | |
| 5,846,730 A | 12/1998 | Miyazaki et al. | |
| 6,747,137 B1 * | 6/2004 | Weinstock et al. | 536/23.1 |
| 2004/0241643 A1 | 12/2004 | Yamamoto et al. | |
| 2007/0134702 A1 | 6/2007 | Fukui et al. | |
| 2008/0113363 A1 | 5/2008 | Fukui et al. | |
| 2008/0113364 A1 | 5/2008 | Fukui et al. | |
| 2008/0113365 A1 | 5/2008 | Kuribayashi et al. | |
| 2008/0113366 A1 | 5/2008 | Kuribayashi et al. | |
| 2008/0124733 A1 | 5/2008 | Fukui et al. | |
| 2008/0161192 A1 | 7/2008 | Yoshii et al. | |
| 2008/0286791 A1 | 11/2008 | Tomatsu et al. | |
| 2008/0286792 A1 | 11/2008 | Tomatsu et al. | |
| 2008/0287312 A1 | 11/2008 | Tomatsu et al. | |
| 2008/0293061 A1 | 11/2008 | Tomatsu et al. | |
| 2008/0293062 A1 | 11/2008 | Tomatsu et al. | |
| 2008/0293063 A1 | 11/2008 | Tomatsu et al. | |
| 2008/0293064 A1 | 11/2008 | Tomatsu et al. | |
| 2008/0293065 A1 | 11/2008 | Tomatsu et al. | |
| 2008/0293066 A1 | 11/2008 | Tomatsu et al. | |
| 2008/0293067 A1 | 11/2008 | Tomatsu et al. | |
| 2008/0299569 A1 | 12/2008 | Tomatsu et al. | |
| 2008/0299570 A1 | 12/2008 | Tomatsu et al. | |
| 2008/0299571 A1 | 12/2008 | Tomatsu et al. | |
| 2008/0299572 A1 | 12/2008 | Tomatsu et al. | |
| 2008/0299573 A1 | 12/2008 | Tomatsu et al. | |
| 2008/0299574 A1 | 12/2008 | Tomatsu et al. | |
| 2008/0299575 A1 | 12/2008 | Tomatsu et al. | |
| 2008/0299576 A1 | 12/2008 | Tomatsu et al. | |
| 2008/0299577 A1 | 12/2008 | Tomatsu et al. | |
| 2008/0299578 A1 | 12/2008 | Tomatsu et al. | |
| 2008/0305487 A1 | 12/2008 | Tomatsu et al. | |
| 2008/0305488 A1 | 12/2008 | Tomatsu et al. | |
| 2009/0004659 A1 | 1/2009 | Tomatsu et al. | |
| 2009/0011419 A1 | 1/2009 | Tomatsu et al. | |
| 2009/0068661 A1 | 3/2009 | Tomatsu et al. | |

FOREIGN PATENT DOCUMENTS

| | | |
|---|---|---|
| JP | 3-167154 | 7/1991 |
| JP | 6-339399 | 12/1994 |
| JP | 11-142409 | 5/1999 |
| JP | 2004-258024 | 9/2004 |
| JP | 2004-313181 | 11/2004 |

OTHER PUBLICATIONS

Japanese Journal of Medical Mycology, vol. 46, Supplement 1, 2005, p. 89, p. 73.
U.S. Appl. No. 12/295,276; filed Mar. 30, 2007, Applicants: Hideto Kuribayashi, et al.
U.S. Appl. No. 12/294,915; filed Mar. 30, 2007, Applicants: Hideto Kuribayashi, et al.
U.S. Appl. No. 12/295,277; filed Mar. 30, 2007, Applicants: Toshifumi Fukui, et al.
U.S. Appl. No. 12/295,273; filed Mar. 30, 2007, Applicants: Hideto Kuribayashi, et al.
U.S. Appl. No. 12/294,910, filed Mar. 30, 2007, Applicants: Hideto Kuribayashi, et al.
U.S. Appl. No. 12/294,914, filed Mar. 30, 2007, Applicant(s): Toshifumi Fukui, et al.
U.S. Appl. No. 12/295,581, filed Mar. 30, 2007, Applicant(s): Hideto Kuribayashi, et al.
U.S. Appl. No. 12/295,584, filed Mar. 30, 2007, Applicant(s): Toshifumi Fukui, et al.
U.S. Appl. No. 12/295,583, filed Mar. 30, 2007, Applicant(s): Toshifumi Fukui, et al.
U.S. Appl. No. 12/295,579, filed Mar. 30, 2007, Applicant(s): Toshifumi Fukui, et al.
U.S. Appl. No. 11/935,930, filed Nov. 6, 2007, Applicant(s): Hiroto Yoshii, et al.
U.S. Appl. No. 11/935,807, filed Nov. 6, 2007, Applicant(s): Hideto Kuribayashi, et al.
U.S. Appl. No. 11/935,789, filed Nov. 6, 2007, Applicant(s): Toshifumi Fukui, et al. U.S. Appl. No. 11/935,820, filed Nov. 6, 2007, Applicant(s): Hideto Kuribayashi, et al.
U.S. Appl. No. 11/935,849, filed Nov. 6, 2007, Applicant(s): Hiroto Yoshii, et al.
U.S. Appl. No. 12/120,172, filed May 13, 2008, Applicants(s): Nobuhiro Tomatsu, et al.

\* cited by examiner

*Primary Examiner* — Mark Navarro
(74) *Attorney, Agent, or Firm* — Fitzpatrick, Cella, Harper & Scinto

(57) ABSTRACT

It is intended to provide a method for identifying a causative fungus of skin disease. The method includes: simultaneously performing amplification treatments under the same conditions using primers common to plural fungal species; then simultaneously performing hybridization procedures under the same conditions using probes respectively specific to fungi; and determining the presence or absence of each fungus from the hybridization intensity of each probe.

10 Claims, 5 Drawing Sheets

SEQUENCE LISTING

```
<160> NUMBER OF SEQ ID NOS: 83

<210> SEQ ID NO 1
<211> LENGTH: 26
<212> TYPE: DNA
<213> ORGANISM: Artificial Sequence
<220> FEATURE:
<223> OTHER INFORMATION: Probe

<400> SEQUENCE: 1
tctttgaaac aaacttgctt tggcgg                                        26

<210> SEQ ID NO 2
<211> LENGTH: 25
<212> TYPE: DNA
<213> ORGANISM: Artificial Sequence
<220> FEATURE:
<223> OTHER INFORMATION: Probe

<400> SEQUENCE: 2
ccgccagagg tctaaactta caacc                                         25

<210> SEQ ID NO 3
<211> LENGTH: 22
<212> TYPE: DNA
<213> ORGANISM: Artificial Sequence
<220> FEATURE:
<223> OTHER INFORMATION: Probe

<400> SEQUENCE: 3
gacggtagtg gtaaggcggg at                                            22

<210> SEQ ID NO 4
<211> LENGTH: 22
<212> TYPE: DNA
<213> ORGANISM: Artificial Sequence
<220> FEATURE:
<223> OTHER INFORMATION: Probe
```

```
<400> SEQUENCE: 4
ggcggtaacg tccaccacgt at                                              22

<210> SEQ ID NO 5
<211> LENGTH: 29
<212> TYPE: DNA
<213> ORGANISM: Artificial Sequence
<220> FEATURE:
<223> OTHER INFORMATION: Probe

<400> SEQUENCE: 5
tgtgttttgt tctggacaaa cttgctttg                                       29

<210> SEQ ID NO 6
<211> LENGTH: 25
<212> TYPE: DNA
<213> ORGANISM: Artificial Sequence
<220> FEATURE:
<223> OTHER INFORMATION: Probe

<400> SEQUENCE: 6
ctgccgccag aggacataaa cttac                                           25

<210> SEQ ID NO 7
<211> LENGTH: 26
<212> TYPE: DNA
<213> ORGANISM: Artificial Sequence
<220> FEATURE:
<223> OTHER INFORMATION: Probe

<400> SEQUENCE: 7
tagtggtata aggcggagat gcttga                                          26

<210> SEQ ID NO 8
<211> LENGTH: 25
<212> TYPE: DNA
<213> ORGANISM: Artificial Sequence
<220> FEATURE:
<223> OTHER INFORMATION: Probe

<400> SEQUENCE: 8
tctggcgtcg cccattttat tcttc                                           25

<210> SEQ ID NO 9
<211> LENGTH: 26
<212> TYPE: DNA
<213> ORGANISM: Artificial Sequence
<220> FEATURE:
<223> OTHER INFORMATION: Probe

<400> SEQUENCE: 9
ggtgttttat cacacgactc gacact                                          26

<210> SEQ ID NO 10
<211> LENGTH: 24
<212> TYPE: DNA
<213> ORGANISM: Artificial Sequence
<220> FEATURE:
<223> OTHER INFORMATION: Probe

<400> SEQUENCE: 10
ggagttctcc cagtggatgc aaac                                            24

<210> SEQ ID NO 11
<211> LENGTH: 24
```

```
<212> TYPE: DNA
<213> ORGANISM: Artificial Sequence
<220> FEATURE:
<223> OTHER INFORMATION: Probe

<400> SEQUENCE: 11
ggccatatca gtatgtggga cacg                                          24

<210> SEQ ID NO 12
<211> LENGTH: 28
<212> TYPE: DNA
<213> ORGANISM: Artificial Sequence
<220> FEATURE:
<223> OTHER INFORMATION: Probe

<400> SEQUENCE: 12
aggttttacc aactcggtgt tgatctag                                      28

<210> SEQ ID NO 13
<211> LENGTH: 22
<212> TYPE: DNA
<213> ORGANISM: Artificial Sequence
<220> FEATURE:
<223> OTHER INFORMATION: Probe

<400> SEQUENCE: 13
gcttaactgc gcggcgaaaa ac                                            22

<210> SEQ ID NO 14
<211> LENGTH: 26
<212> TYPE: DNA
<213> ORGANISM: Artificial Sequence
<220> FEATURE:
<223> OTHER INFORMATION: Probe

<400> SEQUENCE: 14
agataggttg ggccagaggt ttaaca                                        26

<210> SEQ ID NO 15
<211> LENGTH: 25
<212> TYPE: DNA
<213> ORGANISM: Artificial Sequence
<220> FEATURE:
<223> OTHER INFORMATION: Probe

<400> SEQUENCE: 15
tcttagtcgg actaggcgtt tgctt                                         25

<210> SEQ ID NO 16
<211> LENGTH: 22
<212> TYPE: DNA
<213> ORGANISM: Artificial Sequence
<220> FEATURE:
<223> OTHER INFORMATION: Probe

<400> SEQUENCE: 16
tcgttgaatg gtgtggcggg at                                            22

<210> SEQ ID NO 17
<211> LENGTH: 27
<212> TYPE: DNA
<213> ORGANISM: Artificial Sequence
<220> FEATURE:
<223> OTHER INFORMATION: Probe

<400> SEQUENCE: 17
gtgttgcctt ccgaaatatc acagttg                                       27
```

<210> SEQ ID NO 18
<211> LENGTH: 29
<212> TYPE: DNA
<213> ORGANISM: Artificial Sequence
<220> FEATURE:
<223> OTHER INFORMATION: Probe

<400> SEQUENCE: 18
cagttgtcgc aatacgttac ttcaactttt                              29

<210> SEQ ID NO 19
<211> LENGTH: 23
<212> TYPE: DNA
<213> ORGANISM: Artificial Sequence
<220> FEATURE:
<223> OTHER INFORMATION: Probe

<400> SEQUENCE: 19
gcggccagtt cttgattctc tgc                                     23

<210> SEQ ID NO 20
<211> LENGTH: 26
<212> TYPE: DNA
<213> ORGANISM: Artificial Sequence
<220> FEATURE:
<223> OTHER INFORMATION: Probe

<400> SEQUENCE: 20
agctcgtctc tccagtggac ataaac                                  26

<210> SEQ ID NO 21
<211> LENGTH: 22
<212> TYPE: DNA
<213> ORGANISM: Artificial Sequence
<220> FEATURE:
<223> OTHER INFORMATION: Probe

<400> SEQUENCE: 21
ttgaaagtgg ctagccgttg cc                                      22

<210> SEQ ID NO 22
<211> LENGTH: 26
<212> TYPE: DNA
<213> ORGANISM: Artificial Sequence
<220> FEATURE:
<223> OTHER INFORMATION: Probe

<400> SEQUENCE: 22
tcgtggtaag cttgggtcat agagac                                  26

<210> SEQ ID NO 23
<211> LENGTH: 24
<212> TYPE: DNA
<213> ORGANISM: Artificial Sequence
<220> FEATURE:
<223> OTHER INFORMATION: Probe

<400> SEQUENCE: 23
agcggaacga aaacaacaac acct                                    24

<210> SEQ ID NO 24
<211> LENGTH: 24
<212> TYPE: DNA
<213> ORGANISM: Artificial Sequence
<220> FEATURE:
<223> OTHER INFORMATION: Probe

```
<400> SEQUENCE: 24
acctagtgtg aattgcagcc atcg                                          24

<210> SEQ ID NO 25
<211> LENGTH: 22
<212> TYPE: DNA
<213> ORGANISM: Artificial Sequence
<220> FEATURE:
<223> OTHER INFORMATION: Probe

<400> SEQUENCE: 25
gacgtgtaaa gagcgtcgga gc                                            22

<210> SEQ ID NO 26
<211> LENGTH: 25
<212> TYPE: DNA
<213> ORGANISM: Artificial Sequence
<220> FEATURE:
<223> OTHER INFORMATION: Probe

<400> SEQUENCE: 26
gcgagtgttg cgagacaaca aaaag                                         25

<210> SEQ ID NO 27
<211> LENGTH: 22
<212> TYPE: DNA
<213> ORGANISM: Artificial Sequence
<220> FEATURE:
<223> OTHER INFORMATION: Probe

<400> SEQUENCE: 27
ctcgaggcat tcctcgaggc at                                            22

<210> SEQ ID NO 28
<211> LENGTH: 24
<212> TYPE: DNA
<213> ORGANISM: Artificial Sequence
<220> FEATURE:
<223> OTHER INFORMATION: Probe

<400> SEQUENCE: 28
aggcgttgct ccgaaatatc aacc                                          24

<210> SEQ ID NO 29
<211> LENGTH: 23
<212> TYPE: DNA
<213> ORGANISM: Artificial Sequence
<220> FEATURE:
<223> OTHER INFORMATION: Probe

<400> SEQUENCE: 29
tggggcctgc cagagattaa act                                           23

<210> SEQ ID NO 30
<211> LENGTH: 23
<212> TYPE: DNA
<213> ORGANISM: Artificial Sequence
<220> FEATURE:
<223> OTHER INFORMATION: Probe

<400> SEQUENCE: 30
gtgttgagcg atacgctggg ttt                                           23

<210> SEQ ID NO 31
<211> LENGTH: 29
```

<212> TYPE: DNA
<213> ORGANISM: Artificial Sequence
<220> FEATURE:
<223> OTHER INFORMATION: Probe

<400> SEQUENCE: 31
gttttttcca ctcattggta caaactcca                               29

<210> SEQ ID NO 32
<211> LENGTH: 27
<212> TYPE: DNA
<213> ORGANISM: Artificial Sequence
<220> FEATURE:
<223> OTHER INFORMATION: Probe

<400> SEQUENCE: 32
accgccagag gttataacta aaccaaa                                 27

<210> SEQ ID NO 33
<211> LENGTH: 29
<212> TYPE: DNA
<213> ORGANISM: Artificial Sequence
<220> FEATURE:
<223> OTHER INFORMATION: Probe

<400> SEQUENCE: 33
gagcaatacg ctaggtttgt ttgaaagaa                               29

<210> SEQ ID NO 34
<211> LENGTH: 24
<212> TYPE: DNA
<213> ORGANISM: Artificial Sequence
<220> FEATURE:
<223> OTHER INFORMATION: Probe

<400> SEQUENCE: 34
acgcttattt tgctagtggc cacc                                    24

<210> SEQ ID NO 35
<211> LENGTH: 29
<212> TYPE: DNA
<213> ORGANISM: Artificial Sequence
<220> FEATURE:
<223> OTHER INFORMATION: Probe

<400> SEQUENCE: 35
tgaactgttg attgacttcg gtcaattga                               29

<210> SEQ ID NO 36
<211> LENGTH: 26
<212> TYPE: DNA
<213> ORGANISM: Artificial Sequence
<220> FEATURE:
<223> OTHER INFORMATION: Probe

<400> SEQUENCE: 36
gcgtgtttaa cttgtcttat ctggcg                                  26

<210> SEQ ID NO 37
<211> LENGTH: 26
<212> TYPE: DNA
<213> ORGANISM: Artificial Sequence
<220> FEATURE:
<223> OTHER INFORMATION: Probe

<400> SEQUENCE: 37
gttctactac ttgacgcaag tcgagt                                  26

```
<210> SEQ ID NO 38
<211> LENGTH: 23
<212> TYPE: DNA
<213> ORGANISM: Artificial Sequence
<220> FEATURE:
<223> OTHER INFORMATION: Probe

<400> SEQUENCE: 38
ttgggcgtct gcgatttctg atc                                              23

<210> SEQ ID NO 39
<211> LENGTH: 23
<212> TYPE: DNA
<213> ORGANISM: Artificial Sequence
<220> FEATURE:
<223> OTHER INFORMATION: Probe

<400> SEQUENCE: 39
caacggatct cttggcttcc aca                                              23

<210> SEQ ID NO 40
<211> LENGTH: 29
<212> TYPE: DNA
<213> ORGANISM: Artificial Sequence
<220> FEATURE:
<223> OTHER INFORMATION: Probe

<400> SEQUENCE: 40
ttgagagtca tgaaaatctc aatccctcg                                        29

<210> SEQ ID NO 41
<211> LENGTH: 24
<212> TYPE: DNA
<213> ORGANISM: Artificial Sequence
<220> FEATURE:
<223> OTHER INFORMATION: Probe

<400> SEQUENCE: 41
cccgtgtcta tcgtaccttg ttgc                                             24

<210> SEQ ID NO 42
<211> LENGTH: 26
<212> TYPE: DNA
<213> ORGANISM: Artificial Sequence
<220> FEATURE:
<223> OTHER INFORMATION: Probe

<400> SEQUENCE: 42
tgaacgctgt tctgaaagta tgcagt                                           26

<210> SEQ ID NO 43
<211> LENGTH: 23
<212> TYPE: DNA
<213> ORGANISM: Artificial Sequence
<220> FEATURE:
<223> OTHER INFORMATION: Probe

<400> SEQUENCE: 43
gccagccgac acccaacttt att                                              23

<210> SEQ ID NO 44
<211> LENGTH: 25
<212> TYPE: DNA
<213> ORGANISM: Artificial Sequence
<220> FEATURE:
<223> OTHER INFORMATION: Probe
```

```
<400> SEQUENCE: 44
cccatccgtg tctattgtac cctgt                                    25

<210> SEQ ID NO 45
<211> LENGTH: 24
<212> TYPE: DNA
<213> ORGANISM: Artificial Sequence
<220> FEATURE:
<223> OTHER INFORMATION: Probe

<400> SEQUENCE: 45
acacgaacac tgtctgaaag cgtg                                     24

<210> SEQ ID NO 46
<211> LENGTH: 22
<212> TYPE: DNA
<213> ORGANISM: Artificial Sequence
<220> FEATURE:
<223> OTHER INFORMATION: Probe

<400> SEQUENCE: 46
cctgccgacg ttttccaacc at                                       22

<210> SEQ ID NO 47
<211> LENGTH: 24
<212> TYPE: DNA
<213> ORGANISM: Artificial Sequence
<220> FEATURE:
<223> OTHER INFORMATION: Probe

<400> SEQUENCE: 47
tctctctgaa tgctggacgg tgtc                                     24

<210> SEQ ID NO 48
<211> LENGTH: 24
<212> TYPE: DNA
<213> ORGANISM: Artificial Sequence
<220> FEATURE:
<223> OTHER INFORMATION: Probe

<400> SEQUENCE: 48
ctcgccgaag gagtgattct caga                                     24

<210> SEQ ID NO 49
<211> LENGTH: 22
<212> TYPE: DNA
<213> ORGANISM: Artificial Sequence
<220> FEATURE:
<223> OTHER INFORMATION: Probe

<400> SEQUENCE: 49
ttccaccggg agaggagaaa gg                                       22

<210> SEQ ID NO 50
<211> LENGTH: 22
<212> TYPE: DNA
<213> ORGANISM: Artificial Sequence
<220> FEATURE:
<223> OTHER INFORMATION: Probe

<400> SEQUENCE: 50
acaaaaccag cgccttcagg ac                                       22

<210> SEQ ID NO 51
<211> LENGTH: 23
```

```
<212> TYPE: DNA
<213> ORGANISM: Artificial Sequence
<220> FEATURE:
<223> OTHER INFORMATION: Probe

<400> SEQUENCE: 51
cctgaggggg actcttgttt cct                                              23

<210> SEQ ID NO 52
<211> LENGTH: 24
<212> TYPE: DNA
<213> ORGANISM: Artificial Sequence
<220> FEATURE:
<223> OTHER INFORMATION: Probe

<400> SEQUENCE: 52
cgccggagga ttactctgga aaac                                             24

<210> SEQ ID NO 53
<211> LENGTH: 22
<212> TYPE: DNA
<213> ORGANISM: Artificial Sequence
<220> FEATURE:
<223> OTHER INFORMATION: Probe

<400> SEQUENCE: 53
gtccggggac aatcaactcc ct                                               22

<210> SEQ ID NO 54
<211> LENGTH: 27
<212> TYPE: DNA
<213> ORGANISM: Artificial Sequence
<220> FEATURE:
<223> OTHER INFORMATION: Probe

<400> SEQUENCE: 54
aatccatgaa tactgttccg tctgagc                                          27

<210> SEQ ID NO 55
<211> LENGTH: 23
<212> TYPE: DNA
<213> ORGANISM: Artificial Sequence
<220> FEATURE:
<223> OTHER INFORMATION: Probe

<400> SEQUENCE: 55
ggccggtttt ctggcctagt ttt                                              23

<210> SEQ ID NO 56
<211> LENGTH: 22
<212> TYPE: DNA
<213> ORGANISM: Artificial Sequence
<220> FEATURE:
<223> OTHER INFORMATION: Probe

<400> SEQUENCE: 56
agcctctttg ggggctttag ct                                               22

<210> SEQ ID NO 57
<211> LENGTH: 29
<212> TYPE: DNA
<213> ORGANISM: Artificial Sequence
<220> FEATURE:
<223> OTHER INFORMATION: Probe

<400> SEQUENCE: 57
acagacatca aaaatcttg gaaagctgt                                         29
```

<210> SEQ ID NO 58
<211> LENGTH: 22
<212> TYPE: DNA
<213> ORGANISM: Artificial Sequence
<220> FEATURE:
<223> OTHER INFORMATION: Probe

<400> SEQUENCE: 58
ctgggcgaat gggcagtcaa ac                                              22

<210> SEQ ID NO 59
<211> LENGTH: 22
<212> TYPE: DNA
<213> ORGANISM: Artificial Sequence
<220> FEATURE:
<223> OTHER INFORMATION: Probe

<400> SEQUENCE: 59
ctctggcctt cccccaaatc tc                                              22

<210> SEQ ID NO 60
<211> LENGTH: 29
<212> TYPE: DNA
<213> ORGANISM: Artificial Sequence
<220> FEATURE:
<223> OTHER INFORMATION: Probe

<400> SEQUENCE: 60
agacaccaag aaaaaattct ctgaagagc                                       29

<210> SEQ ID NO 61
<211> LENGTH: 22
<212> TYPE: DNA
<213> ORGANISM: Artificial Sequence
<220> FEATURE:
<223> OTHER INFORMATION: Probe

<400> SEQUENCE: 61
gaatgggcag ccaattcagc gc                                              22

<210> SEQ ID NO 62
<211> LENGTH: 20
<212> TYPE: DNA
<213> ORGANISM: Artificial Sequence
<220> FEATURE:
<223> OTHER INFORMATION: Probe

<400> SEQUENCE: 62
cttctgggag cctcgagccg                                                 20

<210> SEQ ID NO 63
<211> LENGTH: 22
<212> TYPE: DNA
<213> ORGANISM: Artificial Sequence
<220> FEATURE:
<223> OTHER INFORMATION: Probe

<400> SEQUENCE: 63
cggcgagcct ctctttatag cg                                              22

<210> SEQ ID NO 64
<211> LENGTH: 24
<212> TYPE: DNA
<213> ORGANISM: Artificial Sequence
<220> FEATURE:
<223> OTHER INFORMATION: Probe

<400> SEQUENCE: 64
cctctcttta tagcggctca acgc                                    24

<210> SEQ ID NO 65
<211> LENGTH: 22
<212> TYPE: DNA
<213> ORGANISM: Artificial Sequence
<220> FEATURE:
<223> OTHER INFORMATION: Probe

<400> SEQUENCE: 65
ggctttctag gcgaatgggc aa                                      22

<210> SEQ ID NO 66
<211> LENGTH: 29
<212> TYPE: DNA
<213> ORGANISM: Artificial Sequence
<220> FEATURE:
<223> OTHER INFORMATION: Probe

<400> SEQUENCE: 66
aggacagaca tcaaaaaatc ttgaagagc                               29

<210> SEQ ID NO 67
<211> LENGTH: 22
<212> TYPE: DNA
<213> ORGANISM: Artificial Sequence
<220> FEATURE:
<223> OTHER INFORMATION: Probe

<400> SEQUENCE: 67
aagctcggct tgtgtgatgg ac                                      22

<210> SEQ ID NO 68
<211> LENGTH: 26
<212> TYPE: DNA
<213> ORGANISM: Artificial Sequence
<220> FEATURE:
<223> OTHER INFORMATION: Probe

<400> SEQUENCE: 68
acaccaagga aaattctctg aagggc                                  26

<210> SEQ ID NO 69
<211> LENGTH: 26
<212> TYPE: DNA
<213> ORGANISM: Artificial Sequence
<220> FEATURE:
<223> OTHER INFORMATION: Probe

<400> SEQUENCE: 69
ccaaggaaaa ttctctgaag gctgt                                   26

<210> SEQ ID NO 70
<211> LENGTH: 24
<212> TYPE: DNA
<213> ORGANISM: Artificial Sequence
<220> FEATURE:
<223> OTHER INFORMATION: Probe

<400> SEQUENCE: 70
tctctttagt ggctcaacgc tgga                                    24

<210> SEQ ID NO 71
<211> LENGTH: 29

```
<212> TYPE: DNA
<213> ORGANISM: Artificial Sequence
<220> FEATURE:
<223> OTHER INFORMATION: Probe

<400> SEQUENCE: 71
ggacagacgc aaaaaaattc tttcagaag                              29

<210> SEQ ID NO 72
<211> LENGTH: 22
<212> TYPE: DNA
<213> ORGANISM: Artificial Sequence
<220> FEATURE:
<223> OTHER INFORMATION: Probe

<400> SEQUENCE: 72
tgggcaataa ccagcgcctc ta                                     22

<210> SEQ ID NO 73
<211> LENGTH: 25
<212> TYPE: DNA
<213> ORGANISM: Artificial Sequence
<220> FEATURE:
<223> OTHER INFORMATION: Probe

<400> SEQUENCE: 73
tcagggatgc atttctctgc gaatc                                  25

<210> SEQ ID NO 74
<211> LENGTH: 25
<212> TYPE: DNA
<213> ORGANISM: Artificial Sequence
<220> FEATURE:
<223> OTHER INFORMATION: Probe

<400> SEQUENCE: 74
cctctcttta gtggctaaac gctgg                                  25

<210> SEQ ID NO 75
<211> LENGTH: 22
<212> TYPE: DNA
<213> ORGANISM: Artificial Sequence
<220> FEATURE:
<223> OTHER INFORMATION: Probe

<400> SEQUENCE: 75
cgccctggcc tcaaaatctg tt                                     22

<210> SEQ ID NO 76
<211> LENGTH: 23
<212> TYPE: DNA
<213> ORGANISM: Artificial Sequence
<220> FEATURE:
<223> OTHER INFORMATION: Probe

<400> SEQUENCE: 76
ttcgagcgtc atttcaaccc ctc                                    23

<210> SEQ ID NO 77
<211> LENGTH: 24
<212> TYPE: DNA
<213> ORGANISM: Artificial Sequence
<220> FEATURE:
<223> OTHER INFORMATION: Probe

<400> SEQUENCE: 77
gttgacctcg gatcaggtag ggat                                   24
```

<210> SEQ ID NO 78
<211> LENGTH: 28
<212> TYPE: DNA
<213> ORGANISM: Artificial Sequence
<220> FEATURE:
<223> OTHER INFORMATION: Probe

<400> SEQUENCE: 78
aactttcaac aacggatctc ttggttct                                    28

<210> SEQ ID NO 79
<211> LENGTH: 22
<212> TYPE: DNA
<213> ORGANISM: Artificial Sequence
<220> FEATURE:
<223> OTHER INFORMATION: Probe

<400> SEQUENCE: 79
gcatcgatga agaacgcagc ga                                          22

<210> SEQ ID NO 80
<211> LENGTH: 27
<212> TYPE: DNA
<213> ORGANISM: Artificial Sequence
<220> FEATURE:
<223> OTHER INFORMATION: Probe

<400> SEQUENCE: 80
gtgaatcatc gaatctttga acgcaca                                     27

<210> SEQ ID NO 81
<211> LENGTH: 19
<212> TYPE: DNA
<213> ORGANISM: Artificial Sequence
<220> FEATURE:
<223> OTHER INFORMATION: Primer

<400> SEQUENCE: 81
tccgtaggtg aacctgcgg                                              19

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
tcctccgctt attgatatgc                                             20

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
tcctccgctt attgatatgc                                             20

PROBE SET, PROBE CARRIER, AND METHOD FOR DETERMINING AND IDENTIFYING FUNGUS

BACKGROUND OF THE INVENTION

1. Field of the Invention

The present invention relates to a method for examining a gene which is useful for the detection and identification of a causative fungus of disease attributed to infection and to a kit for gene examination.

2. Description of the Related Art

Examples of infection caused by fungi include skin disease and deep-seated mycosis.

Meanwhile, some skin diseases cause itching and smallpox in the skin. The causes of these diseases are impossible to visually identify. In general, these skin diseases may be caused by *Trichophyton* (athlete's foot) or may be caused by yeast-like fungi such as *Candida*. These skin diseases are infections caused by fungi. Alternatively, skin disease may be caused not by such fungi but by herpes viruses or may be atopic dermatitis. A drug to be administered totally differs depending on such a different cause of skin disease. Under these circumstances, the development of a method has been demanded by which the cause of skin disease is rapidly diagnosed by determining whether the skin disease is attributed to fungi, bacteria or viruses or attributed to, among the fungi, filamentous fungi or yeast-like fungi.

In general, a specimen collected from an affected area is treated with a potassium hydroxide solution and observed under a microscope. If a hypha can be confirmed in this observation, a fungus is determined as the cause of the disease. In addition, a species of the fungus is usually identified by culture.

On the other hand, a method for identifying an organism species performed by the determination of a nucleic acid sequence is known. Japanese Patent Publication No. H08-024600 discloses a method for detecting a fungus in a specimen, including amplifying ribosomal RNA universally held by pathogenic fungi. Alternatively, Japanese Patent No. 3167154 discloses a method for detecting *Candida albicans* among pathogenic fungi, including amplifying the mitochondrial DNA of this fungus. Likewise, U.S. Pat. No. 5,426,027 discloses primers that can be used in a method including: isolating *Candida albicans* in blood; amplifying a nucleic acid thereof; and detecting this fungus.

Alternatively, Japanese Patent Application Laid-Open No. 2004-258024 discloses a method for identifying a dermatophyte, including performing antigen-antibody reaction with the surface of an isolated fungus using magnetic beads.

On the other hand, Yasuzawa et al. have reported that a nucleic acid is directly amplified by PCR without isolating a fungus from a nail, and a fungal species thereof is identified from the length or number of fragments of the amplification product treated with a restriction enzyme (Yasuzawa et al., (2005), Japanese Journal of Medical Mycology, Vol. 46, No. 1 (Suppl.), p. 89).

Furthermore, the conventional method for identifying an organism species by the determination of a nucleic acid sequence generally involves separating a fungus with specific antibody-immobilized particles and then detecting a gene, as described in detail in, for example, Japanese Patent Application Laid-Open No. H11-142409. Alternatively, Japanese Patent Application Laid-Open No. 2004-313181 discloses a method capable of collectively detecting plural candidates of causative microorganism species by one experiment using a DNA chip.

Thus, a causative fungal species of skin disease can be identified by such conventional techniques.

However, in the visual identification using a microscope, fungal cells are generally difficult to find in the microscope field of view. It may also be difficult to determine whether a filamentous object that has been found is a hypha of a filamentous fungus, a pseudohypha of a yeast-like fungus or dust. Even if the fungus of interest is confirmed to be a yeast-like fungus or filamentous fungus, a fungal species thereof is often impossible to visually identify.

Moreover, the fungal species identification by culture, which is currently performed as a standard method, usually requires a period as very long as approximately 4 weeks. It is not easy to reliably culture a sample collected from a patient. Therefore, such unsuccessful culture highly probably derives a wrong result (false negative) indicating the absence of a fungus in the sample.

In the skin, microorganisms called indigenous microorganisms are also usually present which do not always cause disease. Only these indigenous microorganisms may be grown selectively. In such a case, a causative fungus of disease cannot correctly be identified.

Furthermore, the conventional method for identifying an organism species by the determination of a nucleic acid sequence generally involves separating a fungus with specific antibody-immobilized particles and then detecting a gene, as described in detail in, for example, Japanese Patent Application Laid-Open No. H11-142409. Specifically, after the isolation operation of a fungus, a nucleic acid is further extracted, and the extracted nucleic acid is further sequenced. Thus, this method requires very complicated operation.

Furthermore, the conventional method for identifying an organism species by the determination of a nucleic acid sequence requires designing a primer set for each fungal species to be identified and then performing an amplification experiment by PCR for each possible fungal species. Therefore, the experiment must be performed plural times corresponding to the number of the possible fungal species. Alternatively, a method for multiplexing PCR using plural primer sets by one experiment has been devised and practiced generally as multiplex PCR. In this multiplex PCR method, the experiment is inevitably complicated. This method also requires, for example, respectively introducing different labels for primers or conducting thermal analysis after PCR and as a result, can simultaneously detect only the limited number of fungal species. Both of such an experiment performed plural times or multiplexing by one experiment may be performed. However, in either case, amplification using primers designed for each candidate fungal species is performed for all the candidates. Therefore, the problem is that the amount of a sample collected must be increased according to the number of candidate fungal species.

Japanese Patent Application Laid-Open No. 2004-313181 discloses a method for solving such problems associated with the determination of a nucleic acid sequence. The document discloses a method capable of collectively detecting plural candidates of causative microorganism species by one experiment using a DNA chip. The method disclosed in Japanese Patent Application Laid-Open No. 2004-313181 is directed to a 16S rRNA region of the causative bacterium. However, fungi do not contain such 16S rRNA. Therefore, this method cannot be used for fungi.

The detection method using antigen-antibody reaction, as described in Japanese Patent Application Laid-Open No. 2004-258024, requires isolating fungal cells from a fungus-containing analyte for removing inhibitors of antigen-antibody reaction. Moreover, this antigen-antibody reaction utilizes an antigen on the surface of the fungus. Thus, it is not easy to prepare an antibody capable of sufficiently distinguishing among, for example, closely related fungi, which have similar surface structures.

The method for identifying a fungal species by PCR-RFLP disclosed in Yasuzawa et al., (2005), Japanese Journal of Medical Mycology, Vol. 46, No. 1 (Suppl.), p. 89 indicates the restriction enzyme treatment of PCR amplification products, by which a cleavage site differing among fungal species is expected. In this method, a fungal species is identified from characteristics such as the number or length of fragments produced depending on a fungal species after restriction enzyme treatment. Plural fungal species to be detected may be present. In such a case, according to this method, restriction enzymes must be selected such that the number and length of fragments produced by restriction enzyme treatment differ among these fungal species. Therefore, the selection of appropriate restriction enzymes is more complicated with increases in the number of fungal species to be detected. In the skin, microorganisms called indigenous microorganisms are also present, as already known, which are not always pathogens of infection. The direct extraction of a nucleic acid without isolating a fungus, as described in the document, highly probably causes the coexistence of the nucleic acid of a pathogen of infection with the nucleic acids of such indigenous microorganisms. In this case, the nucleic acid of interest may be contaminated with the nucleic acids derived from unexpected indigenous microorganisms. Therefore, characteristics such as the number or length of fragments obtained by restriction enzyme treatment lead to unexpected complicated combination. Thus, a fungal species is difficult to identify.

SUMMARY OF THE INVENTION

The present invention relates to a method for identifying a fungal species, comprising: extracting a nucleic acid from an affected tissue; amplifying the extracted nucleic acid using a primer set capable of amplifying at least a portion of a nucleic acid sequence region held in common by fungi; and obtaining information about a partial sequence of the amplified nucleic acid which permits fungal species identification and determining and identifying the fungal species of the amplified nucleic acid.

Furthermore, the present invention relates to the method for identifying a fungal species, wherein the amplification reaction using the primer set is PCR.

Furthermore, the present invention relates to the method for identifying a fungal species, wherein the region held in common by fungi is selected from the group consisting of an 18S ribosomal RNA sequence, an ITS region and a 23S ribosomal RNA sequence.

Furthermore, the present invention relates to the method for identifying a fungal species, wherein the determining and identifying the fungal species of the amplified nucleic acid comprises performing hybridization reaction with a nucleic acid probe designed from a partial sequence specific to a fungal species and determining and identifying the fungal species from the obtained hybridization signal intensity.

Furthermore, the present invention relates to the method for identifying a fungal species, wherein the determining and identifying the fungal species of the amplified nucleic acid comprises constituting a probe set from nucleic acid probes designed from partial sequences respectively specific to plural fungal species and using a carrier in which the constituted probe set is immobilized.

Furthermore, the present invention relates to the method for identifying a fungal species, wherein the plural probes constituting the probe set are arranged at a distance from each other on the carrier and used as a probe carrier.

Furthermore, the present invention relates to the method for identifying a fungal species, wherein the nucleic acid probes constituting the probe set have uniform properties such that hybridization conditions can be unified.

Furthermore, the present invention relates to the method for identifying a fungal species, wherein the nucleic acid probes constituting the probe set are designed to have a uniform melting temperature falling within a predetermined range.

Furthermore, the present invention relates to the method for identifying a fungal species, wherein the determining and identifying the fungal species of the amplified nucleic acid comprises using the fact that probes respectively designed for fungal species produce hybridization signal intensities different from each other.

Furthermore, the present invention relates to the method for identifying a fungal species, wherein a probe set is used, the probe set comprising, as the nucleic acid probe, (1) a first probe belonging to any group selected from the following groups 1 to 29 and a second probe belonging to any group selected from the following groups 1 to 29 and not belonging to the group to which the first probe belongs, or (2) a third probe having a nucleotide sequence complementary to the first probe and a fourth probe having a nucleotide sequence complementary to the second probe:

group 1: (1) a probe having a nucleotide sequence tctttgaaacaaacttgctttggcgg (SEQ ID NO: 1), (2) a probe having a nucleotide sequence ccgccagaggtctaaacttacaacc (SEQ ID NO: 2), (3) a probe having a nucleotide sequence gacggtagtggtaaggcgggat (SEQ ID NO: 3), (4) a probe having a nucleotide sequence ggcggtaacgtccaccacgtat (SEQ ID NO: 4), and (5) a probe having a variant sequence of any one of the sequences of SEQ ID NOs: 1 to 4 which has deletion, substitution or addition of a base within a range which can maintain functions as the probe;

group 2: (1) a probe having a nucleotide sequence tgtgttttgttctggacaaacttgctttg (SEQ ID NO: 5), (2) a probe having a nucleotide sequence ctgccgccagaggacataaacttac (SEQ ID NO: 6), (3) a probe having a nucleotide sequence tagtggtataaggcggagatgcttga (SEQ ID NO: 7), (4) a probe having a nucleotide sequence tctggcgtcgcccattttattcttc (SEQ ID NO: 8), and (5) a probe having a variant sequence of any one of the sequences of SEQ ID NOs: 5 to 8 which has deletion, substitution or addition of a base within a range which can maintain functions as the probe;

group 3: (1) a probe having a nucleotide sequence ggtgttttatcacacgactcgacact (SEQ ID NO: 9), (2) a probe having a nucleotide sequence ggagttctcccagtggatgcaaac (SEQ ID NO: 10), (3) a probe having a nucleotide sequence ggccatatcagtatgtgggacacg (SEQ ID NO: 11), (4) a probe having a nucleotide sequence aggttttaccaactcggtgttgatctag (SEQ ID NO: 12), and (5) a probe having a variant sequence of any one of the sequences of SEQ ID NOs: 9 to 12 which has deletion, substitution or addition of a base within a range which can maintain functions as the probe;

group 4: (1) a probe having a nucleotide sequence gcttaactgcgcggcgaaaaac (SEQ ID NO: 13), (2) a probe having a nucleotide sequence agataggttgggccagaggtttaaca (SEQ ID NO: 14), (3) a probe having a nucleotide sequence tcttagtcgactaggcgtttgctt (SEQ ID NO: 15), (4) a probe having a nucleotide sequence tcgttgaatggtgtggcgggat (SEQ ID NO: 16), and (5) a probe having a variant sequence of any one of the sequences of SEQ ID NOs: 13 to 16 which has deletion, substitution or addition of a base within a range which can maintain functions as the probe;

group 5: (1) a probe having a nucleotide sequence gtgttgcttccgaaatatcacagttg (SEQ ID NO: 17), (2) a probe having a nucleotide sequence cagttgtcgcaatacgttacttcaacttt (SEQ ID NO: 18), and (3) a probe having a variant sequence of any one of the sequences of SEQ ID NOs: 17 to 18 which has deletion, substitution or addition of a base within a range which can maintain functions as the probe;

group 6: (1) a probe having a nucleotide sequence gcggccagttcttgattctctgc (SEQ ID NO: 19), (2) a probe having a nucleotide sequence agctcgtctctccagtggacataaac (SEQ ID NO: 20), (3) a probe having a nucleotide sequence ttgaaagtggctagccgttgcc (SEQ ID NO: 21), (4) a probe having a nucleotide sequence tcgtggtaagcttgggtcatagagac (SEQ ID NO: 22), and (5) a probe having a variant sequence of any one of the sequences of SEQ ID NOs: 19 to 22 which has deletion, substitution or addition of a base within a range which can maintain functions as the probe;

group 7: (1) a probe having a nucleotide sequence agcggaacgaaaacaacaacacct (SEQ ID NO: 23), (2) a probe having a nucleotide sequence acctagtgtgaattgcagccatcg (SEQ ID NO: 24), (3) a probe having a nucleotide sequence gacgtgtaaagagcgtcggagc (SEQ ID NO: 25), (4) a probe having a nucleotide sequence gcgagtgttgcgagacaacaaaaag (SEQ ID NO: 26), and (5) a probe having a variant sequence of any one of the sequences of SEQ ID NOs: 23 to 26 which has deletion, substitution or addition of a base within a range which can maintain functions as the probe;

group 8: (1) a probe having a nucleotide sequence ctcgaggcattcctcgaggcat (SEQ ID NO: 27), (2) a probe having a nucleotide sequence aggcgttgctccgaaatatcaacc (SEQ ID NO: 28), and (3) a probe having a variant sequence of any one of the sequences of SEQ ID NOs: 27 to 28 which has deletion, substitution or addition of a base within a range which can maintain functions as the probe;

group 9: (1) a probe having a nucleotide sequence tggggcctgccagagattaaact (SEQ ID NO: 29), (2) a probe having a nucleotide sequence gtgttgagcgatacgctgggttt (SEQ ID NO: 30), (3) a probe having a nucleotide sequence gtttttccactcattggtacaaactcca (SEQ ID NO: 31), and (4) a probe having a variant sequence of any one of the sequences of SEQ ID NOs: 29 to 31 which has deletion, substitution or addition of a base within a range which can maintain functions as the probe;

group 10: (1) a probe having a nucleotide sequence accgccagaggttataactaaaccaaa (SEQ ID NO: 32), (2) a probe having a nucleotide sequence gagcaatacgctaggtttgtttgaaagaa (SEQ ID NO: 33), (3) a probe having a nucleotide sequence acgcttattttgctagtggccacc (SEQ ID NO: 34), and (4) a probe having a variant sequence of any one of the sequences of SEQ ID NOs: 32 to 34 which has deletion, substitution or addition of a base within a range which can maintain functions as the probe;

group 11: (1) a probe having a nucleotide sequence tgaactgttgattgacttcggtcaattga (SEQ ID NO: 35), (2) a probe having a nucleotide sequence gcgtgtttaacttgtcttatctggcg (SEQ ID NO: 36), and (3) a probe having a variant sequence of any one of the sequences of SEQ ID NOs: 35 to 36 which has deletion, substitution or addition of a base within a range which can maintain functions as the probe;

group 12: (1) a probe having a nucleotide sequence gttctactacttgacgcaagtcgagt (SEQ ID NO: 37), (2) a probe having a nucleotide sequence ttgggcgtctgcgatttctgatc (SEQ ID NO: 38), and (3) a probe having a variant sequence of any one of the sequences of SEQ ID NOs: 37 to 38 which has deletion, substitution or addition of a base within a range which can maintain functions as the probe;

group 13: (1) a probe having a nucleotide sequence caacggatctcttggcttccaca (SEQ ID NO: 39), (2) a probe having a nucleotide sequence ttgagagtcatgaaaatctcaatccctcg (SEQ ID NO: 40), and (3) a probe having a variant sequence of any one of the sequences of SEQ ID NOs: 39 to 40 which has deletion, substitution or addition of a base within a range which can maintain functions as the probe;

group 14: (1) a probe having a nucleotide sequence cccgtgtctatcgtaccttgttgc (SEQ ID NO: 41), (2) a probe having a nucleotide sequence tgaacgctgttctgaaagtatgcagt (SEQ ID NO: 42), (3) a probe having a nucleotide sequence gccagccgacaccaactttatt (SEQ ID NO: 43), and (4) a probe having a variant sequence of any one of the sequences of SEQ ID NOs: 41 to 43 which has deletion, substitution or addition of a base within a range which can maintain functions as the probe;

group 15: (1) a probe having a nucleotide sequence cccatccgtgtctattgtaccctgt (SEQ ID NO: 44), (2) a probe having a nucleotide sequence acacgaacactgtctgaaagcgtg (SEQ ID NO: 45), (3) a probe having a nucleotide sequence cctgccgacgttttcaaccat (SEQ ID NO: 46), and (4) a probe having a variant sequence of any one of the sequences of SEQ ID NOs: 44 to 46 which has deletion, substitution or addition of a base within a range which can maintain functions as the probe;

group 16: (1) a probe having a nucleotide sequence tctctctgaatgctggacggtgtc (SEQ ID NO: 47), (2) a probe having a nucleotide sequence ctcgccgaaggagtgattctcaga (SEQ ID NO: 48), (3) a probe having a nucleotide sequence ttccaccgggagaggagaaagg (SEQ ID NO: 49), (4) a probe having a nucleotide sequence acaaaaccagcgccttcaggac (SEQ ID NO: 50), and (5) a probe having a variant sequence of any one of the sequences of SEQ ID NOs: 47 to 50 which has deletion, substitution or addition of a base within a range which can maintain functions as the probe;

group 17: (1) a probe having a nucleotide sequence cctgaggggactcttgtttcct (SEQ ID NO: 51), (2) a probe having a nucleotide sequence cgccggaggattactctggaaaac (SEQ ID NO: 52), and (3) a probe having a variant sequence of any one of the sequences of SEQ ID NOs: 51 and 52 which has deletion, substitution or addition of a base within a range which can maintain functions as the probe;

group 18: (1) a probe having a nucleotide sequence gtccggggacaatcaactccct (SEQ ID NO: 53), (2) a probe having a nucleotide sequence aatccatgaatactgttccgtctgagc (SEQ ID NO: 54), (3) a probe having a nucleotide sequence ggccggttttctggcctagtttt (SEQ ID NO: 55), and (4) a probe having a variant sequence of any one of the sequences of SEQ ID NOs: 53 to 55 which has deletion, substitution or addition of a base within a range which can maintain functions as the probe, group 19: (1) a probe having a nucleotide sequence agcctctttgggggctttagct (SEQ ID NO: 56), (2) a probe having a nucleotide sequence acagacatcaaaaaatcttggaaagctgt (SEQ ID NO: 57), (3) a probe having a nucleotide sequence ctgggcgaatgggcagtcaaac (SEQ ID NO: 58), (4) a probe having a nucleotide sequence ctctggccttcccccaaatctc (SEQ ID NO: 59), and (5) a probe having a variant sequence of any one of the sequences of SEQ ID NOs: 56 to 59 which has deletion, substitution or addition of a base within a range which can maintain functions as the probe;

group 20: (1) a probe having a nucleotide sequence agacaccaagaaaaaattctctgaagagc (SEQ ID NO: 60), (2) a probe having a nucleotide sequence gaatgggcagccaattcagcgc (SEQ ID NO: 61), (3) a probe having a nucleotide sequence cttctggagcctcgagccg (SEQ ID NO: 62), and (4) a probe having a variant sequence of any one of the sequences of SEQ ID NOs: 60 to 62 which has deletion, substitution or addition of a base within a range which can maintain functions as the probe;

group 21: (1) a probe having a nucleotide sequence cggcgagc-
tctctttatagcg (SEQ ID NO: 63), (2) a probe having a nucle-
otide sequence cctctctttatagcggctcaacgc (SEQ ID NO: 64),
(3) a probe having a nucleotide sequence ggctttctaggc-
gaatgggcaa (SEQ ID NO: 65), and (4) a probe having a variant
sequence of any one of the sequences of SEQ ID NOs: 63 to
65 which has deletion, substitution or addition of a base
within a range which can maintain functions as the probe;
group 22: (1) a probe having a nucleotide sequence aggaca-
gacatcaaaaaatcttgaagagc (SEQ ID NO: 66), (2) a probe hav-
ing a nucleotide sequence aagctcggcttgtgtgatggac (SEQ ID
NO: 67), and (3) a probe having a variant sequence of any one
of the sequences of SEQ ID NOs: 66 and 67 which has
deletion, substitution or addition of a base within a range
which can maintain functions as the probe;
group 23: (1) a probe having a nucleotide sequence acaccaag-
gaaaattctctgaagggc (SEQ ID NO: 68), (2) a probe having a
nucleotide sequence ccaaggaaaattctctgaagggctgt (SEQ ID
NO: 69), and (3) a probe having a variant sequence of any one
of the sequences of SEQ ID NOs: 68 and 69 which has
deletion, substitution or addition of a base within a range
which can maintain functions as the probe;
group 24: (1) a probe having a nucleotide sequence tctctt-
tagtggctcaacgctgga (SEQ ID NO: 70), (2) a probe having a
nucleotide sequence ggacagacgcaaaaaaattctttcagaag (SEQ
ID NO: 71), and (3) a probe having a variant sequence of any
one of the sequences of SEQ ID NOs: 70 and 71 which has
deletion, substitution or addition of a base within a range
which can maintain functions as the probe;
group 25: (1) a probe having a nucleotide sequence
tgggcaataaccagcgcctcta (SEQ ID NO: 72), (2) a probe having
a nucleotide sequence tcagggatgcatttctctgcgaatc (SEQ ID
NO: 73), and (3) a probe having a variant sequence of any one
of the sequences of SEQ ID NOs: 72 and 73 which has
deletion, substitution or addition of a base within a range
which can maintain functions as the probe;
group 26: (1) a probe having a nucleotide sequence cctctctt-
tagtggctaaacgctgg (SEQ ID NO: 74), (2) a probe having a
nucleotide sequence cgccctggcctcaaaatctgtt (SEQ ID NO:
75), and (3) a probe having a variant sequence of any one of
the sequences of SEQ ID NOs: 74 and 75 which has deletion,
substitution or addition of a base within a range which can
maintain functions as the probe;
group 27: (1) a probe having a nucleotide sequence ttcgagcgt-
catttcaaccccctc (SEQ ID NO: 76), and (2) a probe having a
variant sequence of the sequence of SEQ ID NO: 76 which
has deletion, substitution or addition of a base within a range
which can maintain functions as the probe;
group 28: (1) a probe having a nucleotide sequence gttgac-
ctcggatcaggtagggat (SEQ ID NO: 77), and (2) a probe having
a variant sequence of the sequence of SEQ ID NO: 77 which
has deletion, substitution or addition of a base within a range
which can maintain functions as the probe; and
group 29: (1) a probe having a nucleotide sequence aactttcaa-
caacggatctcttggttct (SEQ ID NO: 78), (2) a probe having a
nucleotide sequence gcatcgatgaagaacgcagcga (SEQ ID NO:
79), (3) a probe having a nucleotide sequence gtgaatcatc-
gaatctttgaacgcaca (SEQ ID NO: 80), and (4) a probe having a
variant sequence of any one of the sequences of SEQ ID NOs:
78 to 80 which has deletion, substitution or addition of a base
within a range which can maintain functions as the probe.

Furthermore, the present invention relates to a kit for fun-
gal species identification comprising: the probe carrier; and a
reagent for detecting the reaction between the probe and a
target nucleic acid.

According to the present invention, the identification of the
presence or absence of a causative fungus of disease, or a
fungal species thereof can be performed more reliably and
rapidly than a conventional method by microscopic examina-
tion or culture. Furthermore, the present invention enables
more convenient identification of a fungal species than a
conventional method including designing primers for each
possible fungus and identifying a fungal species from the
amplification products. The present invention also enables
more convenient identification of a fungal species than a
conventional method including isolating a fungus from an
affected area and then performing gene examination and anti-
body examination. The present invention can also be applied
to nucleic acids extracted from plural fungal species. In such
a case, the hybridization signals of probes respectively
designed for fungi can be analyzed independently. Therefore,
the present invention enables reliable identification of a fun-
gal species.

Further features of the present invention will become
apparent from the following description of exemplary
embodiments with reference to the attached drawings.

DESCRIPTION OF THE EMBODIMENTS

Preferred embodiments of the present invention will now
be described in detail in accordance with the accompanying
drawings.

Figure 1:
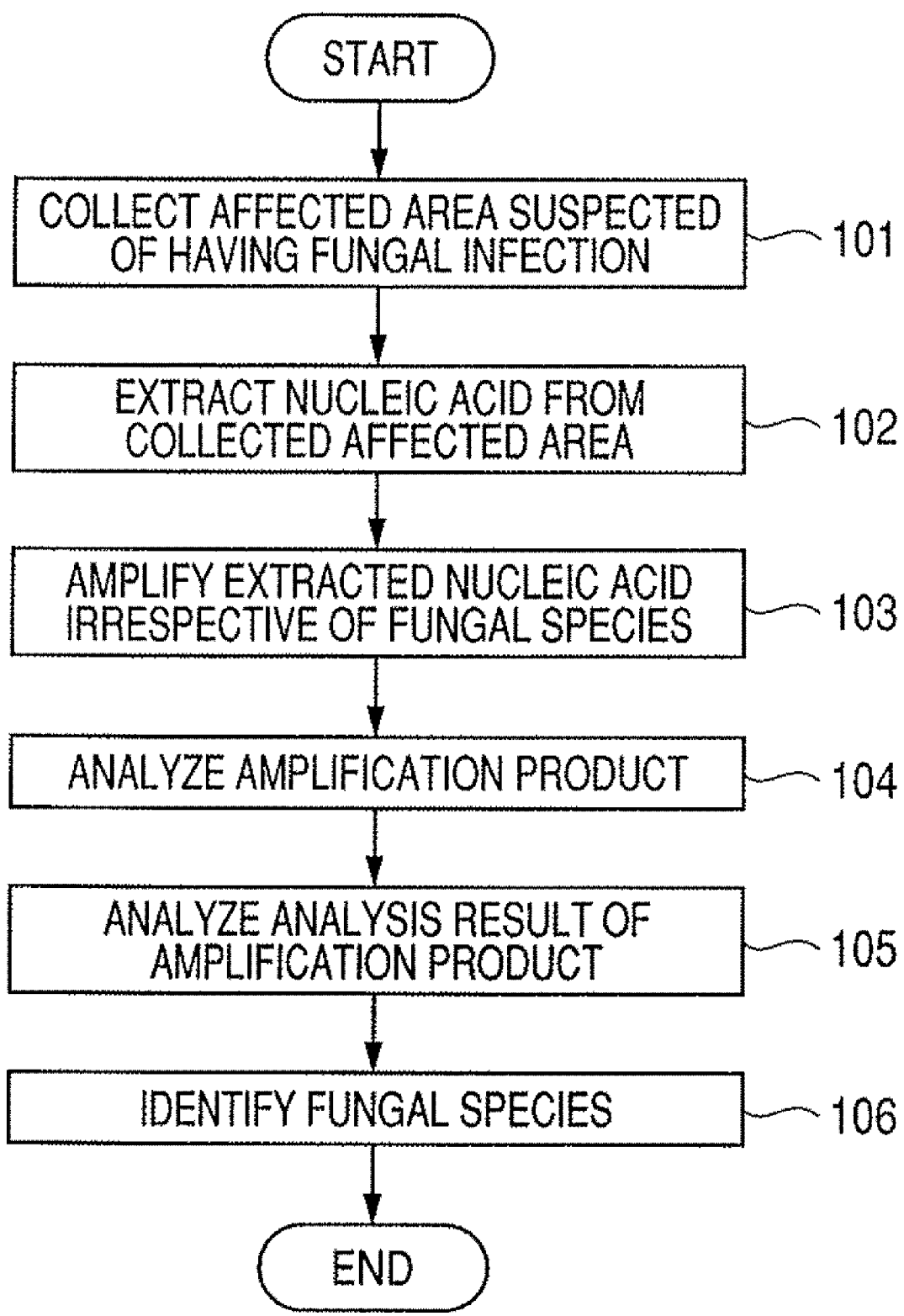
FIG. 1 is a flow chart illustrating an embodiment of the
present invention.

An embodiment of the present invention will be described
with reference to FIG. 1. FIG. 1 is a flow chart illustrating the
outline of a method for identifying a fungal species according
to the present invention. An affected area infected with a
fungus is collected (101). The affected area together with the
fungus is then dissolved or disrupted to extract a nucleic acid
(102). The extracted nucleic acid is amplified (103) using
primers having a nucleic acid sequence capable of amplifying
a region which is possessed commonly by fungi but of which
sequence is not common in these 26 fungal species. Then,
analysis is conducted (104) for obtaining information about a
partial sequence of the amplified nucleic acid (amplification
product) which permits fungal species identification. This
analysis result is analyzed (105), and a fungal species is
identified (106).

In the nucleic acid amplification, primers capable of col-
lectively amplifying the genomic sequences of fungi to be
detected, irrespective of fungal species, may be used alone or
as a primer set including plural combined primers.

In the nucleic acid amplification, a label may be intro-
duced.

The analysis for obtaining information about a partial
sequence of the amplified nucleic acid which permits fungal
species identification includes various methods such as hybridization using a probe, the sequencing of a fungal species-specific partial sequence, and mass spectrometry.

To use the approach of hybridization using a probe, probes designed from partial sequences respectively specific to plural possible fungal species can be used simultaneously. This is because a highly possible fungus and a low possible fungus can be determined clearly by comprehensive determination after the determination of the hybridization intensity of each probe. This is also because plural fungal species, if simultaneously causing infections, can be identified individually from the hybridization intensity of each probe. Furthermore, this is because increases in the number of probes simultaneously used can impart redundancy to information obtained from hybridization results. Furthermore, this is because the hybridization results serve as listing data indicating results of simultaneously detecting plural fungi.

The method of the present invention may be directed to skin disease as fungal infection. In such a case, both of a causative fungus of skin disease and indigenous microorganisms usually present even in normal individuals may be present in a skin disease-affected area. A causative fungus of disease is usually present in larger amounts in an affected area than that of indigenous microorganisms. Therefore, a quantitative ratio of extractable nucleic acids differs between the causative fungus and the indigenous microorganism. In this context, according to the method of the present invention, amplification treatment is performed using nucleic acid primers capable of amplifying both of the indigenous microorganism and the causative fungus of disease. Difference in the amount of nucleic acids after amplification is larger than that in the amount of nucleic acids after extraction. As a result, in the detection of hybridization signal intensity, an intensity ratio thereof is increased. The indigenous microorganisms and the causative fungus can be discriminated from the signal intensity ratio.

Staphylococci, which are observed as indigenous microorganisms, have a ribosomal RNA region sequence different from fungi. Therefore, amplification using a ribosomal RNA region specific to fungi can eliminate staphylococcus-derived nucleic acids from the nucleic acid amplification products. Thus, the indigenous microorganisms and the causative fungus can be discriminated.

A nucleic acid extracted from a skin disease-affected tissue slice contains skin-derived human genomes. For the amplification using nucleic acid primers, the design and use of primers are important which do not permit the amplification of these human genomes. Examples of the nucleic acid sequence region held in common by fungi include 18S ribosomal RNA, an ITS region and 26S ribosomal RNA. The design of primers or a primer set is important which are capable of collectively amplifying at least a portion of these regions in fungi, independently of fungal species. These primers or primer set are designed based on the premise that the primers or primer set do not permit the amplification of human genomes.

On the other hand, cells such as hair free of a root, keratinized skin and nails are enucleated. Therefore, nucleic acids extracted from these specimens do not contain human genomes. Accordingly, if nucleic acids can be extracted from specimens and amplified using the primer set capable of amplifying at least a portion of a nucleic acid sequence region held in common by fungi, the specimens are shown to contain some fungus.

The method of the present invention may also be directed to blood disease as fungal infection. In such a case, an extracted nucleic acid contains leukocyte-derived human genomes. In this case as well, primers must be designed for use which are capable of selectively amplifying only fungal genomes without amplifying the human genomes.

According to the method of the present invention, nucleic acid amplification may not be observed using the primer set capable of amplifying at least a portion of a nucleic acid sequence region held in common by fungi. In such a case, it can be determined that skin disease is not caused by fungi. In this case, other causes such as bacteria, viruses, atopy, autoimmune disease and drug eruption are expected. Therefore, drug candidates used for treatment can be narrowed down rapidly.

Figure 5:
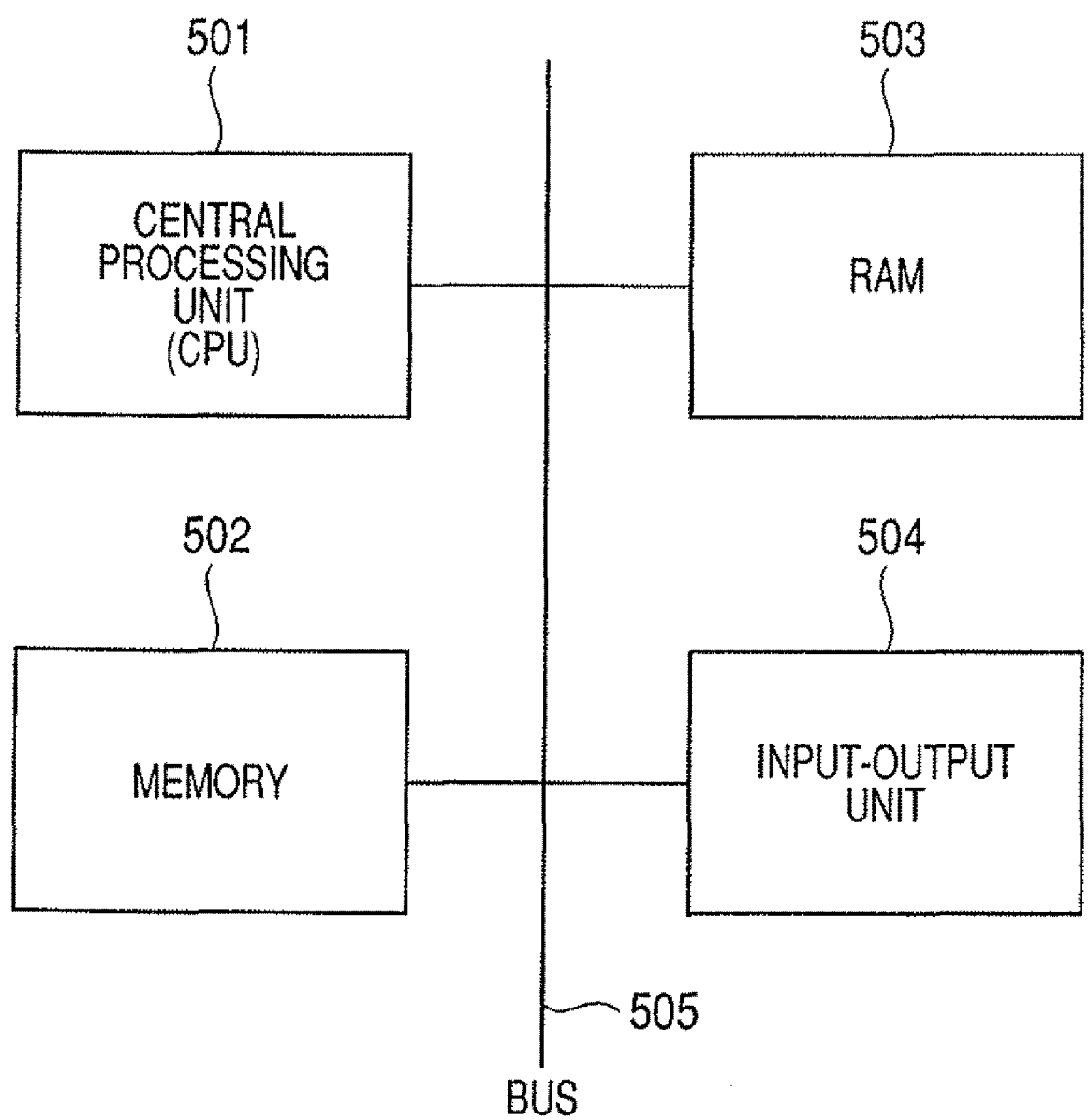
FIG. 5 is a diagram illustrating an information processing
apparatus in which determination software is operated.

In the analysis for obtaining information about a partial sequence of the amplified nucleic acid which permits fungal species identification, the approach of hybridization using a nucleic acid probe may be used. In such a case, a fungal species can be identified by analyzing hybridization signals. To identify a fungal species by analyzing hybridization signals, determination software may be used in which fungal species determination logic is incorporated. FIG. 5 is a block diagram illustrating an information processing apparatus in which determination software according to the present embodiment is operated. The determination software is installed in an apparatus which includes a central processing unit (CPU) 501, a memory 502, RAM 503 and an input-output unit 504 connected via a bus 505. Specifically, this software can be installed in a general personal computer, a workstation, or the like. In FIG. 5, the central processing unit (CPU) 501 temporarily stores, on the RAM 503, the program of the present embodiment stored in the memory 502 or data necessary for executing the program of the present embodiment and executes the program of the present embodiment. The input-output unit 504 includes a display, a keyboard, a pointing device, a printing apparatus, a network interface, and so on, and performs user interaction to execute the program of the present embodiment. In many cases, a user executes the program of the present embodiment via this input-output unit 504. A user also reads execution results or controls parameters during program execution via this input-output unit 504. The determination software receives data on hybridization results by input and normalizes the input data, if necessary, for data analysis. As a result, the software outputs the presence or absence of a fungus in the hybridized sample, existing probability of a fungus, or the name of a fungus that is present.

The present invention further provides a probe set including two or more combined probes for fungal species identification. The use of this probe set permits the detection of any one of 26 fungi below or the simultaneous detection of plural species thereof.

1) *Candida albicans*
2) *Candida dubliniensis*
3) *Candida glabrata*
4) *Candida guilliermondii*
5) *Candida intermedia*
6) *Candida kefyr*
7) *Candida krusei*
8) *Candida lusitaniae*
9) *Candida parapsilosis*
10) *Candida tropicalis*
11) *Trichosporon cutaneum*
12) *Trichosporon asahii*
13) *Cryptococcus neoformans*
14) *Aspergillus fumigatus*
15) *Aspergillus niger*
16) *Epidermophyton floccosum*
17) *Arthroderma otae*
18) *Arthroderma gypseum*
19) *Arthroderma benhamiae*

20) *Trichophyton rubrum*
21) *Trichophyton tonsurans*
22) *Trichophyton verrucosum*
23) *Trichophyton violaceum*
24) *Arthroderma vanbreuseghemii*
25) *Arthroderma incurvatum*
26) *Trichophyton interdigitale*

Specifically, the present invention provides a probe set for sufficiently detecting an ITS region which is possessed commonly by fungi but of which sequence is not common in these 26 fungal species. Probes constituting the probe set according to the present invention are reacted with a sample containing a nucleic acid having the DNA sequence itself of a fungal ITS region or a nucleotide sequence specific to the ITS region. The probes constituting the probe set used in fungal species identification according to the present invention are selected as the following combination (1) or (2): (1) a first probe belonging to any group selected from the following groups 1 to 29 and a second probe belonging to any group selected from the following groups 1 to 29 and not belonging to the group to which the first probe belongs, or (2) a third probe having a nucleotide sequence complementary to the first probe and a fourth probe having a nucleotide sequence complementary to the second probe:

group 1: (1) a probe having a nucleotide sequence tctttgaaacaaacttgctttggcgg (SEQ ID NO: 1), (2) a probe having a nucleotide sequence ccgccagaggtctaaacttacaacc (SEQ ID NO: 2), (3) a probe having a nucleotide sequence gacggtagtggtaaggcgggat (SEQ ID NO: 3), (4) a probe having a nucleotide sequence ggcggtaacgtccaccacgtat (SEQ ID NO: 4), and (5) a probe having a variant sequence of any one of the sequences of SEQ ID NOs: 1 to 4 which has deletion, substitution or addition of a base within a range which can maintain functions as the probe;

group 2: (1) a probe having a nucleotide sequence tgtgttttgttctggacaaacttgctttg (SEQ ID NO: 5), (2) a probe having a nucleotide sequence ctgccgccagaggacataaacttac (SEQ ID NO: 6), (3) a probe having a nucleotide sequence tagtggtataaggcggagatgcttga (SEQ ID NO: 7), (4) a probe having a nucleotide sequence tctggcgtcgcccattttattcttc (SEQ ID NO: 8), and (5) a probe having a variant sequence of any one of the sequences of SEQ ID NOs: 5 to 8 which has deletion, substitution or addition of a base within a range which can maintain functions as the probe;

group 3: (1) a probe having a nucleotide sequence ggtgttttatcacacgactcgacact (SEQ ID NO: 9), (2) a probe having a nucleotide sequence ggagttctcccagtggatgcaaac (SEQ ID NO: 10), (3) a probe having a nucleotide sequence ggccatatcagtatgtgggacacg (SEQ ID NO: 11), (4) a probe having a nucleotide sequence aggttttaccaactcggtgttgatctag (SEQ ID NO: 12), and (5) a probe having a variant sequence of any one of the sequences of SEQ ID NOs: 9 to 12 which has deletion, substitution or addition of a base within a range which can maintain functions as the probe;

group 4: (1) a probe having a nucleotide sequence gcttaactgcgcggcgaaaaac (SEQ ID NO: 13), (2) a probe having a nucleotide sequence agataggttgggccagaggtttaaca (SEQ ID NO: 14), (3) a probe having a nucleotide sequence tcttagtcggactaggcgtttgctt (SEQ ID NO: 15), (4) a probe having a nucleotide sequence tcgttgaatggtgtggcgggat (SEQ ID NO: 16), and (5) a probe having a variant sequence of any one of the sequences of SEQ ID NOs: 13 to 16 which has deletion, substitution or addition of a base within a range which can maintain functions as the probe;

group 5: (1) a probe having a nucleotide sequence gtgttgccttccgaaatatcacagttg (SEQ ID NO: 17), (2) a probe having a nucleotide sequence cagttgtcgcaatacgttacttcaacttt (SEQ ID NO: 18), and (3) a probe having a variant sequence of any one of the sequences of SEQ ID NOs: 17 to 18 which has deletion, substitution or addition of a base within a range which can maintain functions as the probe;

group 6: (1) a probe having a nucleotide sequence gcggccagttcttgattctctgc (SEQ ID NO: 19), (2) a probe having a nucleotide sequence agctcgtctctccagtggacataaac (SEQ ID NO: 20), (3) a probe having a nucleotide sequence ttgaaagtggctagccgttgcc (SEQ ID NO: 21), (4) a probe having a nucleotide sequence tcgtggtaagcttgggtcatagagac (SEQ ID NO: 22), and (5) a probe having a variant sequence of any one of the sequences of SEQ ID NOs: 19 to 22 which has deletion, substitution or addition of a base within a range which can maintain functions as the probe;

group 7: (1) a probe having a nucleotide sequence agcggaacgaaaacaacaacacct (SEQ ID NO: 23), (2) a probe having a nucleotide sequence acctagtgtgaattgcagccatcg (SEQ ID NO: 24), (3) a probe having a nucleotide sequence gacgtgtaaagagcgtcggagc (SEQ ID NO: 25), (4) a probe having a nucleotide sequence gcgagtgttgcgagacaacaaaaag (SEQ ID NO: 26), and (5) a probe having a variant sequence of any one of the sequences of SEQ ID NOs: 23 to 26 which has deletion, substitution or addition of a base within a range which can maintain functions as the probe;

group 8: (1) a probe having a nucleotide sequence ctcgaggcattcctcgaggcat (SEQ ID NO: 27), (2) a probe having a nucleotide sequence aggcgttgctccgaaatatcaacc (SEQ ID NO: 28), and (3) a probe having a variant sequence of any one of the sequences of SEQ ID NOs: 27 to 28 which has deletion, substitution or addition of a base within a range which can maintain functions as the probe;

group 9: (1) a probe having a nucleotide sequence tggggcctgccagagattaaact (SEQ ID NO: 29), (2) a probe having a nucleotide sequence gtgttgagcgatacgctgggttt (SEQ ID NO: 30), (3) a probe having a nucleotide sequence gttttttccactcattggtacaaactcca (SEQ ID NO: 31), and (4) a probe having a variant sequence of any one of the sequences of SEQ ID NOs: 29 to 31 which has deletion, substitution or addition of a base within a range which can maintain functions as the probe;

group 10: (1) a probe having a nucleotide sequence accgccagaggttataactaaaccaaa (SEQ ID NO: 32), (2) a probe having a nucleotide sequence gagcaatacgctaggtttgtttgaaagaa (SEQ ID NO: 33), (3) a probe having a nucleotide sequence acgcttattttgctagtggccacc (SEQ ID NO: 34), and (4) a probe having a variant sequence of any one of the sequences of SEQ ID NOs: 32 to 34 which has deletion, substitution or addition of a base within a range which can maintain functions as the probe;

group 11: (1) a probe having a nucleotide sequence tgaactgttgattgacttcggtcaattga (SEQ ID NO: 35), (2) a probe having a nucleotide sequence gcgtgtttaacttgtcttatctggcg (SEQ ID NO: 36), and (3) a probe having a variant sequence of any one of the sequences of SEQ ID NOs: 35 to 36 which has deletion, substitution or addition of a base within a range which can maintain functions as the probe;

group 12: (1) a probe having a nucleotide sequence gttctactacttgacgcaagtcgagt (SEQ ID NO: 37), (2) a probe having a nucleotide sequence ttgggcgtctgcgatttctgatc (SEQ ID NO: 38), and (3) a probe having a variant sequence of any one of the sequences of SEQ ID NOs: 37 to 38 which has deletion, substitution or addition of a base within a range which can maintain functions as the probe;

group 13: (1) a probe having a nucleotide sequence caacggatctcttggcttccaca (SEQ ID NO: 39), (2) a probe having a nucleotide sequence ttgagagtcatgaaaatctcaatccctcg (SEQ ID NO: 40), and (3) a probe having a variant sequence of any one of the sequences of SEQ ID NOs: 39 to 40 which has deletion, substitution or addition of a base within a range which can maintain functions as the probe;

group 14: (1) a probe having a nucleotide sequence cccgtgtctatcgtaccttgttgc (SEQ ID NO: 41), (2) a probe having a nucleotide sequence tgaacgctgttctgaaagtatgcagt (SEQ ID NO: 42), (3) a probe having a nucleotide sequence gccagccgacaccaactttatt (SEQ ID NO: 43), and (4) a probe having a variant sequence of any one of the sequences of SEQ ID NOs: 41 to 43 which has deletion, substitution or addition of a base within a range which can maintain functions as the probe;

group 15: (1) a probe having a nucleotide sequence cccatccgtgtctattgtaccctgt (SEQ ID NO: 44), (2) a probe having a nucleotide sequence acacgaacactgtctgaaagcgtg (SEQ ID NO: 45), (3) a probe having a nucleotide sequence cctgccgacgttttcaaccat (SEQ ID NO: 46), and (4) a probe having a variant sequence of any one of the sequences of SEQ ID NOs: 44 to 46 which has deletion, substitution or addition of a base within a range which can maintain functions as the probe;

group 16: (1) a probe having a nucleotide sequence tctctctgaatgctggacggtgtc (SEQ ID NO: 47), (2) a probe having a nucleotide sequence ctcgccgaaggagtgattctcaga (SEQ ID NO: 48), (3) a probe having a nucleotide sequence ttccaccgggagaggagaaagg (SEQ ID NO: 49), (4) a probe having a nucleotide sequence acaaaaccagcgccttcaggac (SEQ ID NO: 50), and (5) a probe having a variant sequence of any one of the sequences of SEQ ID NOs: 47 to 50 which has deletion, substitution or addition of a base within a range which can maintain functions as the probe;

group 17: (1) a probe having a nucleotide sequence cctgaggggactcttgtttcct (SEQ ID NO: 51), (2) a probe having a nucleotide sequence cgccggaggattactctggaaaac (SEQ ID NO: 52), and (3) a probe having a variant sequence of any one of the sequences of SEQ ID NOs: 51 and 52 which has deletion, substitution or addition of a base within a range which can maintain functions as the probe;

group 18: (1) a probe having a nucleotide sequence gtccgggacaatcaactccct (SEQ ID NO: 53), (2) a probe having a nucleotide sequence aatccatgaatactgttccgtctgagc (SEQ ID NO: 54), (3) a probe having a nucleotide sequence ggccggttttctgcctagttt (SEQ ID NO: 55), and (4) a probe having a variant sequence of any one of the sequences of SEQ ID NOs: 53 to 55 which has deletion, substitution or addition of a base within a range which can maintain functions as the probe;

group 19: (1) a probe having a nucleotide sequence agcctctttggggcttagct (SEQ ID NO: 56), (2) a probe having a nucleotide sequence acagacatcaaaaaatcttggaaagctgt (SEQ ID NO: 57), (3) a probe having a nucleotide sequence ctgggcgaatgggcagtcaaac (SEQ ID NO: 58), (4) a probe having a nucleotide sequence ctctggccttcccccaaatctc (SEQ ID NO: 59), and (5) a probe having a variant sequence of any one of the sequences of SEQ ID NOs: 56 to 59 which has deletion, substitution or addition of a base within a range which can maintain functions as the probe;

group 20: (1) a probe having a nucleotide sequence agacaccaagaaaaaattctctgaagagc (SEQ ID NO: 60), (2) a probe having a nucleotide sequence gaatgggcagccaattcagcgc (SEQ ID NO: 61), (3) a probe having a nucleotide sequence cttctggagcctcgagccg (SEQ ID NO: 62), and (4) a probe having a variant sequence of any one of the sequences of SEQ ID NOs: 60 to 62 which has deletion, substitution or addition of a base within a range which can maintain functions as the probe;

group 21: (1) a probe having a nucleotide sequence cggcgagctctctttatagcg (SEQ ID NO: 63), (2) a probe having a nucleotide sequence cctctctttatagcggctcaacgc (SEQ ID NO: 64), (3) a probe having a nucleotide sequence ggctttctaggcgaatgggcaa (SEQ ID NO: 65), and (4) a probe having a variant sequence of any one of the sequences of SEQ ID NOs: 63 to 65 which has deletion, substitution or addition of a base within a range which can maintain functions as the probe;

group 22: (1) a probe having a nucleotide sequence aggacagacatcaaaaaattcttgaagagc (SEQ ID NO: 66), (2) a probe having a nucleotide sequence aagctcggcttgtgtgatggac (SEQ ID NO: 67), and (3) a probe having a variant sequence of any one of the sequences of SEQ ID NOs: 66 and 67 which has deletion, substitution or addition of a base within a range which can maintain functions as the probe;

group 23: (1) a probe having a nucleotide sequence acaccaaggaaaattctctgaagggc (SEQ ID NO: 68), (2) a probe having a nucleotide sequence ccaaggaaaattctctgaagggctgt (SEQ ID NO: 69), and (3) a probe having a variant sequence of any one of the sequences of SEQ ID NOs: 68 and 69 which has deletion, substitution or addition of a base within a range which can maintain functions as the probe;

group 24: (1) a probe having a nucleotide sequence tctctttagtggctcaacgctgga (SEQ ID NO: 70), (2) a probe having a nucleotide sequence ggacagacgcaaaaaaattcttcagaag (SEQ ID NO: 71), and (3) a probe having a variant sequence of any one of the sequences of SEQ ID NOs: 70 and 71 which has deletion, substitution or addition of a base within a range which can maintain functions as the probe;

group 25: (1) a probe having a nucleotide sequence tgggcaataaccagcgcctcta (SEQ ID NO: 72), (2) a probe having a nucleotide sequence tcagggatgcatttctctgcgaatc (SEQ ID NO: 73), and (3) a probe having a variant sequence of any one of the sequences of SEQ ID NOs: 72 and 73 which has deletion, substitution or addition of a base within a range which can maintain functions as the probe;

group 26: (1) a probe having a nucleotide sequence cctctctttagtggctaaacgctgg (SEQ ID NO: 74), (2) a probe having a nucleotide sequence cgccctggcctcaaaatctgtt (SEQ ID NO: 75), and (3) a probe having a variant sequence of any one of the sequences of SEQ ID NOs: 74 and 75 which has deletion, substitution or addition of a base within a range which can maintain functions as the probe;

group 27: (1) a probe having a nucleotide sequence ttcgagcgtcatttcaacccctc (SEQ ID NO: 76), and (2) a probe having a variant sequence of the sequence of SEQ ID NO: 76 which has deletion, substitution or addition of a base within a range which can maintain functions as the probe;

group 28: (1) a probe having a nucleotide sequence gttgacctcggatcaggtagggat (SEQ ID NO: 77), and (2) a probe having a variant sequence of the sequence of SEQ ID NO: 77 which has deletion, substitution or addition of a base within a range which can maintain functions as the probe; and group 29: (1) a probe having a nucleotide sequence aactttcaacaacggatctcttggttct (SEQ ID NO: 78), (2) a probe having a nucleotide sequence gcatcgatgaagaacgcagcga (SEQ ID NO: 79), (3) a probe having a nucleotide sequence gtgaatcatcgaatctttgaacgcaca (SEQ ID NO: 80), and (4) a probe having a variant sequence of any one of the sequences of SEQ ID NOs: 78 to 80 which has deletion, substitution or addition of a base within a range which can maintain functions as the probe.

One to four probes belong to each of the groups. The probe set includes at least two probes and at most 80 probes.

The variant sequence has a variation within a range which does not impair functions as the probe, that is, within a range which can detect a target nucleic acid sequence to be detected by hybridization. Particularly, the variant sequence can have a variation within a range which permits hybridization with a target nucleic acid sequence to be detected under stringent conditions. Examples of suitable hybridization conditions that specify the range of the variation can include conditions described in Examples below. In this context, the target to be detected is contained in an analyte for hybridization and may be the nucleotide sequence itself specific to a pathogen of infection or a complementary sequence of this specific nucleotide sequence. Examples of the variation can include the deletion, substitution or addition of one or several bases, which is performed within a range which can maintain functions as the probe.

These probe functions largely depend on the specificity of the probe sequence to a target nucleic acid sequence to be examined. The specificity of the probe sequence can be evaluated from base match to the target nucleic acid sequence and melting temperatures between the target nucleic acid sequence and the probe sequence. The performance of a probe constituting the probe set also depends on variations from the melting temperatures of other probe sequences.

To design these probe sequences, a universal region among fungal species is selected such that the selected region does not vary even among different strains of the same species. Moreover, a specific region is selected which has base mismatch of three or more bases from the sequence of a fungal species other than the fungal species of interest. The probe sequences are designed such that melting temperatures between the probe sequence and the sequence of the fungal species of interest differ by 10° C. or more from melting temperatures between the probe sequence and the sequence of a fungal species other than the fungal species of interest. Furthermore, the probes immobilized on one carrier are designed to have their respective melting temperatures falling within a predetermined range. The melting temperatures are controlled by deleting or adding a base in or to the highly specific region.

To design these probe sequences, low homology to the sequence of *Malassezia* known as an indigenous fungus in the skin is taken into consideration. Thus, a pathogenic fungus to be detected by the probe set of the present invention and *Malassezia* as an indigenous fungus can be discriminated. Specifically, the probe of the present invention is capable of identifying the fungal species to be detected in the presence of *Malassezia*.

Experiments of the present inventors have demonstrated that a probe sequence in which 80% or more of its consecutive sequence is conserved gives little attenuation of hybridization intensity. This means that a variant sequence in which 80% or more of consecutive nucleotide sequence in the probe sequence disclosed by the present application is conserved does not impair probe functions.

In this context, the detection functions of each of the groups are shown below.
group 1: *Candida albicans*
group 2: *Candida dubliniensis*
group 3: *Candida glabrata*
group 4: *Candida guilliermondii*
group 5: *Candida intermedia*
group 6: *Candida kefyr*
group 7: *Candida krusei*
group 8: *Candida lusitaniae*
group 9: *Candida parapsilosis*
group 10: *Candida tropicalis*
group 11: *Trichosporon cutaneum*
group 12: *Trichosporon asahii*
group 13: *Cryptococcus neoformans*
group 14: *Aspergillus fumigatus*
group 15: *Aspergillus niger*
group 16: *Epidermophyton floccosum*
group 17: *Arthroderma otae*
group 18: *Arthroderma gypseum*
group 19: *Arthroderma benhamiae*
group 20: *Trichophyton rubrum*
group 21: *Trichophyton tonsurans*
group 22: *Trichophyton verrucosum*
group 23: *Trichophyton violaceum*
group 24: *Arthroderma vanbreuseghemii*
group 25: *Arthroderma incurvatum*
group 26: *Trichophyton interdigitale*
group 27: For detection of *Trichophyton* (fungi in groups 16 to 26 and their closely related fungi)
group 28: For detection of filamentous fungi (fungi in groups 14 to 26 and their closely related fungi)
group 29: For detection of fungi (fungi in groups 1 to 26 and their closely related fungi)

Sequences complementary to these probe sequences have the same functions and are also effective as probe sequences. Two or more probes having these complementary sequences can be used to constitute a probe set.

The probes were respectively designed for fungi from the ITS region portion in the DNA sequence such that very high specificity to the fungi, no variations among the probe nucleotide sequences, and sufficient hybridization sensitivity can be expected.

The nucleotide sequences of these probes are designed to have a melting temperature falling within a predetermined range such that the probes form stable hybrids with analytes in the hybridization reaction between one or more of the probes bound with and immobilized on a carrier and the analytes and produce favorable results. The melting temperature is controlled by adjusting the length of the nucleotide sequences and a constituent ratio of bases.

These probe sequences are also designed to permit fungal species determination by combining plural characteristic portions without determining the whole sequence of the ITS region.

Accordingly, the information about a partial sequence of the amplified nucleic acid which permits fungal species identification can be obtained using these probe sequences.

Moreover, the combined use of the probes specific to fungal species and the probes specific to fungal groups can more increase distinct sites in portions characteristics of the fungi and enables more precise determination of a fungal species.

Specifically, determination using only one probe of the present invention enables acquisition of sequence information based on only the number of bases in the nucleotide sequence of each probe, that is, detection of the presence or absence of a complementary sequence.

Such determination is performed by increasing the number of probes for different sequence regions to 2, 3, etc. and is achieved based on the total number of bases of the sequences. Specifically, increases in the number of probes more improve the precision of determination of the presence or absence of the fungal sequence.

Such probes for determination may be selected as probes that are not limited to specific sequences held by particular fungal species. These probes are group probes. Therefore, the use of both of the group and species probes further improves determination precision.

Furthermore, a probe carrier (e.g., a DNA chip) in which the probes for fungal species identification according to the present invention are immobilized can be obtained by supplying the probes to predetermined positions in a carrier and immobilizing the probes thereon. The supply of the probes to a carrier can be performed using various methods. For example, a method that can be used is capable of immobilizing probes onto a carrier through a chemical bond (e.g., a covalent bond) and includes adding solutions containing these probes to predetermined positions in the carrier by an inkjet printing method. As a result, the probes are hardly dissociated from the carrier, and the effect of improving sensitivity is also additionally produced. Specifically, a DNA chip prepared by a conventional stamping method called the Stanford method generally used has the disadvantage that DNA applied to a carrier is easily dissociated therefrom. An alternative method for preparing a DNA chip includes arranging probes by DNA synthesis on carrier surface (e.g., Affymetrix oligonucleotide array). For this method including synthesizing probes on a carrier, the probes are difficult to synthesize in uniform amounts. Therefore, the amount of the probe immobilized tends to considerably differ among probe-immobilized regions (spots). Due to such variations in the amount of the probe immobilized, precise evaluation may not be made on detection results obtained using such a probe carrier. From these viewpoints, the probe carrier according to the present invention can be prepared using the inkjet printing method. The inkjet printer method has the advantage that: probes are stably immobilized on a carrier and hardly dissociated therefrom; and a probe carrier capable of achieving highly sensitive and highly precise detection can be provided efficiently.

To immobilize plural probes on a carrier for use, the probes can be designed to have a predetermined melting temperature such that a hybridization protocol can be simplified and unified.

Hereinafter, an exemplary embodiment of the present invention will be described in more detail.

Terms used herein will be described below.

A "specimen" refers to an object obtained for examination. An "analyte" refers to such a specimen adjusted to contain DNA or nucleic acid fragments. A "sample" refers to an object to be reacted with probes. The specimen may be reacted directly with probes. In such a case, the "sample" encompasses the specimen. Alternatively, the analyte adjusted from the specimen may be reacted with probes. In such a case, the "sample" encompasses the analyte.

The sample to be examined using the probe carrier (e.g., a DNA chip) used in the method for identifying a fungal species according to the present invention includes those derived from animals such as humans and livestock. For example, any of body fluids (e.g., blood, spinal fluid, sputum, stomach fluid, vaginal secretions and oral mucus), tissue slices (e.g., nails, skin and hair), and excretions (urine and feces) probably having bacteria can be used as a sample to be examined. Alternative examples of the sample to be examined include all media probably contaminated with bacteria, such as: food and water in the environment (e.g., drink water and hot spring water) which cause food poisoning or are contaminated; and filters for air cleaners. Furthermore, animals and plants to be quarantined during import and export are used as samples to be examined.

Such a specimen may be used directly in reaction with the DNA chip. In such a case, the specimen is reacted as a sample with the DNA chip, and the obtained results are analyzed. Alternatively, such a specimen may not directly be reacted with the DNA chip. In such a case, the specimen is subjected to necessary treatment such as the extraction and purification of a target substance to obtain an analyte. Then, this analyte is reacted as a sample with the DNA chip. For example, an extract probably containing a target nucleic acid is prepared from an analyte derived from a specimen containing the target nucleic acid and further subjected to necessary treatment such as washing or dilution to prepare a specimen solution. Then, this specimen solution may be reacted with the DNA chip. A specimen containing a target nucleic acid is subjected to various amplification treatments such as PCR amplification to amplify this target nucleic acid. Then, the resulting specimen may be reacted with the DNA chip. Such a nucleic acid analyte for amplification includes the following:

(a) an analyte prepared using PCR reaction primers designed for detecting an ITS region,
(b) an analyte prepared by further subjecting the PCR amplification product to PCR reaction,
(c) an analyte prepared by an amplification method other than PCR, and
(d) an analyte labeled by various labeling methods for visualization.

Any carrier that can satisfy characteristics which permit solid phase-liquid phase reaction of interest may be used in the preparation of the probe-immobilized carrier such as a DNA chip. For example, flat substrates (e.g., glass substrates, plastic substrates and silicon wafers), three-dimensional structures having asperities, spherical (e.g., beads), rod-shaped, cord-shaped, and thread-shaped carriers can be used. Furthermore, the carrier may be surface-treated such that probes can be immobilized thereon. Particularly, a carrier having functional groups for chemical reaction introduced to its surface is stably bound with probes in the process of hybridization reaction and is suitable in terms of reproducibility.

The immobilization of probes can be performed using various methods. One example thereof can include a method using the combination of maleimide and thiol (—SH) groups. This method includes binding thiol (—SH) groups to the ends of probes and treating carrier (solid phase) surface to have maleimide groups. As a result, the thiol groups of the probes supplied to the carrier surface are reacted with the maleimide groups on the carrier surface to immobilize the probes via the covalent bonds formed therebetween.

The introduction of maleimide groups can be performed using a method including first reacting an aminosilane coupling agent with a glass substrate and next introducing maleimide groups through the reaction between the amino groups thereof and an EMCS reagent (N-(6-Maleimidocaproyloxy) succinimide, manufactured by DOJINDO LABORATORIES). The introduction of thiol groups to DNA can be performed using 5'-Thiol-Modifier C6 (manufactured by Glen Research) in an automatic DNA synthesizer. Examples of the combination of functional groups used in the immobilization include, in addition to the combination of the thiol and maleimide groups, the combination of epoxy (on a solid phase) and amino (at the ends of nucleic acid probes) groups. Surface treatment using various silane coupling agents is also effective. In this case, probes are used in which functional groups capable of reacting with functional groups introduced using the silane coupling agent are introduced. A method including coating a carrier with a resin having functional groups is also available.

The detection of the DNA of a pathogen of infection using the probe carrier according to the present invention can be performed by a DNA detection method including at least:

(i) preparing a sample from a nucleic acid extracted from an affected area;
(ii) reacting the sample with the probe carrier in which the probes according to the present invention are immobilized; and
(iii) detecting the intensity of the reaction between the probe on the probe carrier and the nucleic acid in the sample.

Alternatively, the detection method can include at least:

(A) preparing a sample from a nucleic acid extracted from an affected area;
(B) reacting the sample with the probe carrier in which the probes according to the present invention are immobilized;

(C) detecting the presence or absence of the reaction between the probe on the probe carrier and the nucleic acid in the sample; and
(D) when the reaction between the probe and the nucleic acid in the sample is detected, identifying the probe reacted with the nucleic acid in the sample and identifying the DNA of a pathogen of infection contained in the sample, based on the nucleotide sequence of the identified probe.

As described above, an ITS region may be targeted as a region which is possessed commonly by fungi but of which sequence is not common in these 26 fungal species. The nucleotide sequence of the ITS region may be amplified by PCR to prepare a sample for reaction with the probe carrier. In such a case, a primer set for detection of a pathogen of infection can be used. Primers suitable for this primer set are oligonucleotides having the following generally known nucleotide sequences:
(1) 5' tccgtaggtgaacctgcgg 3' (ITS1; SEQ ID NO: 81), and
(2) 5' tcctccgcttattgatatgc 3' (ITS4; SEQ ID NO: 82).
Accordingly, the method for identifying a fungal species according to the present invention may further include PCR-amplifying a target nucleic acid in the specimen using the primer set having the nucleotide sequences of ITS1 and ITS4.

At least the probe set described above and a reagent for detecting the reaction between a nucleic acid in a sample and each probe can be used to constitute a kit for fungal species identification. The probe set in this kit may be provided, as described above, as a probe set immobilized on a carrier. Alternatively, the reagent for detection may contain a label for reaction detection and primers for amplification as pretreatment. The reagent for detection containing primers can include primers for amplifying the DNA of a fungal ITS region.

EXAMPLES

Hereinafter, the present invention will be described in more detail.

Example 1

Preparation of DNA Chip for Fungal Species Identification

A DNA chip is prepared which is capable of identifying a fungal species by hybridization with nucleic acids amplified from the common regions of fungal species to be detected.

1. Selection of Fungi to be Detected

One embodiment of a method for identifying a fungal species described in the present invention was directed to fungi shown in Table 1 below as fungi to be detected.

TABLE 1

| Possible fungal species | |
|---|---|
| No. | Fungal Name |
| 1 | Candida albicans |
| 2 | Candida dubliniensis |
| 3 | Candida glabrata |
| 4 | Candida guilliermondii |
| 5 | Candida intermedia |
| 6 | Candida kefyr |
| 7 | Candida krusei |
| 8 | Candida lusitaniae |
| 9 | Candida parapsilosis |
| 10 | Candida tropicalis |
| 11 | Trichosporon cutaneum |

TABLE 1-continued

| Possible fungal species | |
|---|---|
| No. | Fungal Name |
| 12 | Trichosporon asahii |
| 13 | Cryptococcus neoformans |
| 14 | Aspergillus fumigatus |
| 15 | Aspergillus niger |
| 16 | Epidermophyton floccosum |
| 17 | Arthroderma otae |
| 18 | Arthroderma gypseum |
| 19 | Arthroderma benhamiae |
| 20 | Trichophyton rubrum |
| 21 | Trichophyton tonsurans |
| 22 | Trichophyton verrucosum |
| 23 | Trichophyton violaceum |
| 24 | Arthroderma vanbreuseghemii |
| 25 | Arthroderma incurvatum |
| 26 | Trichophyton interdigitale |

The fungal species shown in Table 1 are listed for describing one embodiment of the present invention. It is obvious that the same identification method as in the present invention can also be applied to embodiments including fungi to be detected other than those described above.

2. Selection of Region to be Amplified

One embodiment of the method for identifying a fungal species described in the present invention was directed to an ITS region as a region which is possessed commonly by fungi but of which sequence is not common in these 26 fungal specie. In addition, generally known primers shown in Table 2 below were used as primers capable of amplifying in common the ITS regions of the fungal species shown in Table 1.

TABLE 2

| Primer capable of amplification irrespective of fungal species | | | |
|---|---|---|---|
| Primer Type | Primer Name | Primer Sequence | SEQ ID No: |
| Forward Primer | ITS1 | 5' tccgtaggtgaacctgcgg 3' | 81 |
| Reverse Primer | ITS4 | 5' tcctccgcttattgatatgc 3' | 82 |

The primers shown in Table 2 amplify the ITS region selected as a region to be amplified. It is obvious that if another gene region is used, primers capable of amplifying in common the gene region irrespective of fungal species may be used according to the nucleic acid sequence thereof.

3. Design of Fungus-Specific Probe

For the regions amplified with the primers shown in Table 2, probes shown in Tables 3 to 5 below were designed from regions respectively specific to the fungi shown in Table 1.

TABLE 3

| Group | Fungal Name | Probe Name | Nucleotide Sequence | SEQ ID No: |
|---|---|---|---|---|
| 1 | Candida albicans | P0101 | 5' tctttgaaacaaacttgctttggcgg 3' | 1 |
| | | P0102 | 5' ccgccagaggtctaaacttacaacc 3' | 2 |
| | | P0103 | 5' gacggtagtggtaaggcgggat 3' | 3 |
| | | P0104 | 5' ggcggtaacgtccaccacgtat 3' | 4 |
| 2 | Candida dubliniensis | P0201 | 5' tgtgttttgttctggacaaacttgctttg 3' | 5 |
| | | P0202 | 5' ctgccgccagaggacataaacttac 3' | 6 |
| | | P0204 | 5' tagtggtataaggcggagatgcttga 3' | 7 |
| | | P0205 | 5' tctggcgtcgcccattttattcttc 3' | 8 |
| 3 | Candida glabrata | P0302 | 5' ggtgttttatcacacgactcgacact 3' | 9 |
| | | P0303 | 5' ggagttctcccagtggatgcaaac 3' | 10 |
| | | P0304 | 5' ggccatatcagtatgtgggacacg 3' | 11 |
| | | P0305 | 5' aggttttaccaactcggtgttgatctag 3' | 12 |
| 4 | Candida guilliermondii | P0401 | 5' gcttaactgcgcggcgaaaaac 3' | 13 |
| | | P0402 | 5' agataggttgggccagaggtttaaca 3' | 14 |
| | | P0403 | 5' tcttagtcggactaggcgtttgctt 3' | 15 |
| | | P0404 | 5' tcgttgaatggtgtggcgggat 3' | 16 |
| 5 | Candida intermedia | P0503 | 5' gtgttgccttccgaaatatcacagttg 3' | 17 |
| | | P0502 | 5' cagttgtcgcaatacgttacttcaactttt 3' | 18 |
| 6 | Candida kefyr | P0601 | 5' gcggccagttcttgattctctgc 3' | 19 |
| | | P0602 | 5' agctcgtctctccagtggacataaac 3' | 20 |
| | | P0603 | 5' ttgaaagtggctagccgttgcc 3' | 21 |
| | | P0604 | 5' tcgtggtaagcttgggtcatagagac 3' | 22 |
| 7 | Candida krusei | P0701 | 5' agcggaacgaaaacaacaacacct 3' | 23 |
| | | P0702 | 5' acctagtgtgaattgcagccatcg 3' | 24 |
| | | P0703 | 5' gacgtgtaaagagcgtcggagc 3' | 25 |
| | | P0704 | 5' gcgagtgttgcgagacaacaaaaag 3' | 26 |
| 8 | Candida lusitaniae | P0801 | 5' ctcgaggcattcctcgaggcat 3' | 27 |
| | | P0803 | 5' aggcgttgctccgaaatatcaacc 3' | 28 |

TABLE 4

| Group | Fungal Name | Probe Name | Nucleotide Sequence | SEQ ID No: |
|---|---|---|---|---|
| 9 | Candida parapsilosis | P0901 | 5' tggggcctgccagagattaaact 3' | 29 |
| | | P0902 | 5' gtgttgagcgatacgctgggttt 3' | 30 |
| | | P0903 | 5' gttttttccactcattggtacaaactcca 3' | 31 |
| 10 | Candida tropicalis | P1102 | 5' accgccagaggttataactaaaccaaa 3' | 32 |
| | | P1103 | 5' gagcaatacgctaggtttgtttgaaagaa 3' | 33 |
| | | P1104 | 5' acgcttattttgctagtggccacc 3' | 34 |
| 11 | Trichosporon cutaneum | P2701 | 5' tgaactgttgattgacttcggtcaattga 3' | 35 |
| | | P2702 | 5' gcgtgtttaacttgtcttatctggcg 3' | 36 |
| 12 | Trichosporon asahii | P2801 | 5' gttctactacttgacgcaagtcgagt 3' | 37 |
| | | P2802 | 5' ttgggcgtctgcgatttctgatc 3' | 38 |
| 13 | Cryptococcus neoformans | P3301 | 5' caacggatctcttggcttccaca 3' | 39 |
| | | P3302 | 5' ttgagagtcatgaaaatctcaatccctcg 3' | 40 |
| 14 | Aspergillus fumigatus | P2901 | 5' cccgtgtctatcgtaccttgttgc 3' | 41 |
| | | P2902 | 5' tgaacgctgttctgaaagtatgcagt 3' | 42 |
| | | P2903 | 5' gccagccgacacccaactttatt 3' | 43 |
| 15 | Aspergillus niger | P3001 | 5' cccatccgtgtctattgtaccctgt 3' | 44 |
| | | P3002 | 5' acacgaacactgtctgaaagcgtg 3' | 45 |
| | | P3003 | 5' cctgccgacgttttccaaccat 3' | 46 |
| 16 | Epidermophyton flocoosum | P1901 | 5' tctctctgaatgctggacggtgtc 3' | 47 |
| | | P1902 | 5' ctcgccgaaggagtgattctcaga 3' | 48 |
| | | P1903 | 5' ttccaccgggagaggagaaagg 3' | 49 |
| | | P1904 | 5' acaaaaccagcgccttcaggac 3' | 50 |

TABLE 4-continued

| Group | Fungal Name | Probe Name | Nucleotide Sequence | SEQ ID No: |
|---|---|---|---|---|
| 17 | Arthroderma otae | P2001 | 5' cctgaggggactcttgtttcct 3' | 51 |
|  |  | P2002 | 5' cgccggaggattactctggaaaac 3' | 52 |
| 18 | Arthroderma gypseum | P2105 | 5' gtccggggacaatcaactccct 3' | 53 |
|  |  | P2102 | 5' aatccatgaatactgttccgtctgagc 3' | 54 |
|  |  | P2103 | 5' ggccggttttctggcctagtttt 3' | 55 |

TABLE 5

| Group | Fungal Name | Probe Name | Nucleotide Sequence | SEQ ID No: |
|---|---|---|---|---|
| 19 | Arthroderma benhamiae | P2205 | 5' agcctctttgggggctttagct 3' | 56 |
|  |  | P2202 | 5' acagacatcaaaaaatcttggaaagctgt 3' | 57 |
|  |  | P2203 | 5' ctgggcgaatgggcagtcaaac 3' | 58 |
|  |  | P2204 | 5' ctctggccttcccccaaatctc 3' | 59 |
| 20 | Trichophyton rubrum | P2302 | 5' agacaccaagaaaaaattctctgaagagc 3' | 60 |
|  |  | P2306 | 5' gaatgggcagccaattcagcgc 3' | 61 |
|  |  | P2305 | 5' cttctgggagcctcgagccg 3' | 62 |
| 21 | Trichophyron tonsurans | P2405 | 5' cggcgagcctctctttatagcg 3' | 63 |
|  |  | P2402 | 5' cctctctttatagcggctcaacgc 3' | 64 |
|  |  | P2403 | 5' ggcttttctaggcgaatgggcaa 3' | 65 |
| 22 | Trichophyton verrucosum | P2501 | 5' aggacagacatcaaaaaatcttgaagagc 3' | 66 |
|  |  | P2502 | 5' aagctcggcttgtgtgatggac 3' | 67 |
| 23 | Trichophyton violaceum | P2604 | 5' acaccaaggaaaattctctgaagggc 3' | 68 |
|  |  | P2601 | 5' ccaaggaaaattctctgaagggctgt 3' | 69 |
| 24 | Arthroderma vanbreuseghemii | P3101 | 5' tctctttagtggctcaacgctgga 3' | 70 |
|  |  | P3102 | 5' ggacagacgcaaaaaaattctttcagaag 3' | 71 |
| 25 | Arthroderma incurvatum | P3201 | 5' tgggcaataaccagcgcctcta 3' | 72 |
|  |  | P3202 | 5' tcagggatgcatttctctgcgaatc 3' | 73 |
| 26 | Trichophyton interdigitale | P3401 | 5' cctctctttagtggctaaacgctgg 3' | 74 |
|  |  | P3402 | 5' cgccctggcctcaaaatctgtt 3' | 75 |
| 27 | Common to Trichophyton | Ptricho1 | 5' ttcgagcgtcatttcaaccctc 3' | 76 |
| 28 | Common to Filamentous Fungi | Pfila1 | 5' gttgacctcggatcaggtagggat 3' | 77 |
| 29 | Common to Fungi | Pfungi1 | 5' aactttcaacaacggatctcttggttct 3' | 78 |
|  |  | Pfungi2 | 5' gcatcgatgaagaacgcagcga 3' | 79 |
|  |  | Pfungi3 | 5' gtgaatcatcgaatctttgaacgcaca 3' | 80 |

The designed probes were not only probes respectively specific to fungal species but also probes respectively specific to groups of fungi (Groups 27, 28 and 29).

The probe common to *Trichophyton* of the group 27 is designed from a sequence common to the fungi in the groups 16 to 26. The probe common to filamentous fungi of the group 28 is designed from a sequence common to the fungi in the groups 14 to 26. The probe common to fungi of the group 29 is designed from a sequence common to the fungi in the groups 1 to 26.

4. Preparation of DNA Chip

To achieve collective detection using the probes shown in Tables 3 to 5, a DNA chip was prepared in which these probes were immobilized on a glass substrate.

4-1. Washing of Glass Substrate

A synthetic quartz glass substrate (size: 25 mm×75 mm×1 mm; manufactured by IIYAMA PRECISION GLASS CO., LTD.) was placed in a rack resistant to heat and alkali and dipped in a washing solution for ultrasonic washing prepared to a predetermined concentration. After overnight dipping in the washing solution, the substrate was ultrasonically washed for 20 minutes. Subsequently, the substrate was taken out of the solution and lightly rinsed with pure water. The substrate was then ultrasonically washed in ultrapure water for 20 minutes. Next, the substrate was dipped for 10 minutes in a 1 N aqueous sodium hydroxide solution heated to 80° C. The substrate was washed again with pure water and then with ultrapure water to prepare a quartz glass substrate for a DNA chip.

4-2. Surface Treatment

A silane coupling agent KBM-603 (manufactured by Shin-Etsu Chemical Co., Ltd.) was dissolved at a concentration of 1% by weight (wt %) in pure water and stirred at room temperature for 2 hours. Subsequently, the previously washed glass substrate was dipped in the aqueous solution of the silane coupling agent and left at room temperature for 20 minutes. The glass substrate was pulled out of the solution. The surface of the substrate was lightly washed with pure water. Nitrogen gas was then sprayed on both surfaces of the substrate to dry the substrate. Next, the dried substrate was baked for 1 hour in an oven heated to 120° C. to complete the coupling agent treatment such that amino groups were introduced in the substrate surface. Subsequently, N-maleimidocaproyloxysuccinimide (hereinafter, abbreviated to EMCS) was dissolved at a final concentration of 0.3 mg/ml in a 1:1 (by volume) mixed solvent of dimethyl sulfoxide and ethanol to prepare an EMCS solution. The EMCS used is (N-(6-Maleimidocaproyloxy)succinimide) manufactured by DOJINDO LABORATORIES.

The completely baked glass substrate was allowed to cool and dipped in the prepared EMCS solution at room temperature for 2 hours. This treatment caused the reaction between the amino groups introduced in the surface by the silane coupling agent and the succinimide groups of EMCS such that the maleimide groups were introduced in the glass substrate surface. The glass substrate pulled out of the EMCS solution was washed with the mixed solvent containing the EMCS dissolved therein and further with ethanol and then dried in a nitrogen gas atmosphere.

4-3. Probe DNA

The probes in the probe set for fungus detection prepared in the paragraph '3. Design of fungus-specific probe' were separately dissolved in pure water and dispensed at a final concentration of 10 μM (in terms of a concentration after dissolution in ink). The solutions were freeze-dried to remove water.

4-4. Discharge of DNA Using Inkjet Printer and Binding Thereof to Substrate

An aqueous solution was prepared which contained 7.5 wt % glycerin, 7.5 wt % thiodiglycol, 7.5 wt % urea and 1.0 wt % Acetylenol EH (manufactured by Kawaken Fine Chemicals Co., Ltd.). Subsequently, the previously prepared 80 probes (Tables 3 to 5) were separately dissolved at the specified concentration in the mixed solvent. The obtained DNA solutions were charged into an ink tank for an inkjet printer (trade name: BJF-850 manufactured by Canon Inc.), which was mounted on a print head.

The inkjet printer used here was modified to permit flat plate printing. This inkjet printer is capable of inputting a print pattern according to a predetermined file creation method such that approximately 5 picoliters of a DNA solution are spotted with a pitch of approximately 120 μm.

Subsequently, print operation using this modified inkjet printer was conducted on one glass substrate to prepare an array. After confirmation that printing was performed with reliability, the substrate was left standing in a humidifying chamber for 30 minutes to cause the reaction between the maleimide groups in the glass substrate surface and the thiol groups at the ends of the nucleic acid probes.

4-5. Washing

After 30-minute reaction, the DNA solution remaining on the substrate surface was washed away with a 10 mM phosphate buffer solution (pH 7.0) containing 100 mM NaCl to obtain a DNA chip in which single-stranded DNAs were immobilized on the glass substrate surface.

5. DNA Collection from Fungi

To confirm the performance of the prepared DNA chip, DNA was extracted from fungal strains shown below.

5-1. Microorganism Culture and DNA Extraction

Fungal strains shown in Table 6 below were cultured according to a standard method. DNA extraction and purification were performed from this microorganism culture solution using a nucleic acid purification kit (FastPrep FP100A and FastDNA Kit; manufactured by Funakoshi Co., Ltd.).

TABLE 6

| Fungal species and strain name | | |
|---|---|---|
| No. | Fungal Name | Strain Name |
| 1 | Candida albicans | JCM 1542 |
| 2 | Candida dubliniensis | ATCC MYA-646 |
| 3 | Candida glabrata | JCM 3761 |
| 4 | Candida guilliermondii | ATCC 6260 |
| 5 | Candida intermedia | ATCC 14439 |
| 6 | Candida kefyr | ATCC 42265 |
| 7 | Candida krusei | JCM 1609 |
| 8 | Candida lusitaniae | ATCC 34449 |
| 9 | Candida parapsilosis | JCM 1618 |
| 10 | Candida tropicalis | JCM 1541 |
| 11 | Trichosporon cutaneum | JCM 1462 |
| 12 | Trichosporon asahii | JCM 1809 |
| 13 | Cryptococcus neoformans | ATCC 32045 |
| 14 | Aspergillus fumigatus | JCM 10253 |
| 15 | Aspergillus niger | JCM 10254 |
| 16 | Epidermophyton floccosum | ATCC 52063 |
| 17 | Arthroderma otae | ATCC 28327 |
| 18 | Arthroderma gypseum | ATCC 24163 |
| 19 | Arthroderma benhamiae | ATCC 16781 |
| 20 | Trichophyton rubrum | ATCC 10218 |
| 21 | Trichophyton tonsurans | ATCC 10217 |
| 22 | Trichophyton verrucosum | ATCC 28203 |
| 23 | Trichophyton violaceum | ATCC 28944 |
| 24 | Arthroderma vanbreuseghemii | ATCC 28145 |
| 25 | Arthroderma incurvatum | ATCC 24005 |
| 26 | Trichophyton interdigitale | IFM 55365 |

5-2. Examination of Collected DNA

The collected DNA of each fungal strain was subjected to agarose electrophoresis and absorbance measurement at 260/280 nm according to a standard method to assay the quality thereof (the amount of low-molecular-weight nucleic acids contaminating and the degree of degradation) and the amount of DNA collected. In the present Example, approximately 10 μg of DNA was collected, and DNA degradation or ribosomal RNA contamination were not observed. The collected DNA was dissolved at a final concentration of 50 ng/μl in a TE buffer solution, and this solution was used in Examples below.

6. Amplification and Labeling 6-1. Nucleic Acid Amplification: 1st PCR

The extracted nucleic acids were amplified. Specifically, PCR was performed according to solution composition shown in Table 7 using the primers shown in Table 2.

TABLE 7

| 1st PCR solution composition | |
|---|---|
| TaKaRa ExTaq | 25.0 μL |
| Primer mix | 2.0 μL |
| Forward Primer | 1.0 μL |
| Reverse Primer | 1.0 μL |
| Template | 1.0 μL |
| Water | up to 50 μL |
| Total | 50 μL |

Figure 2:
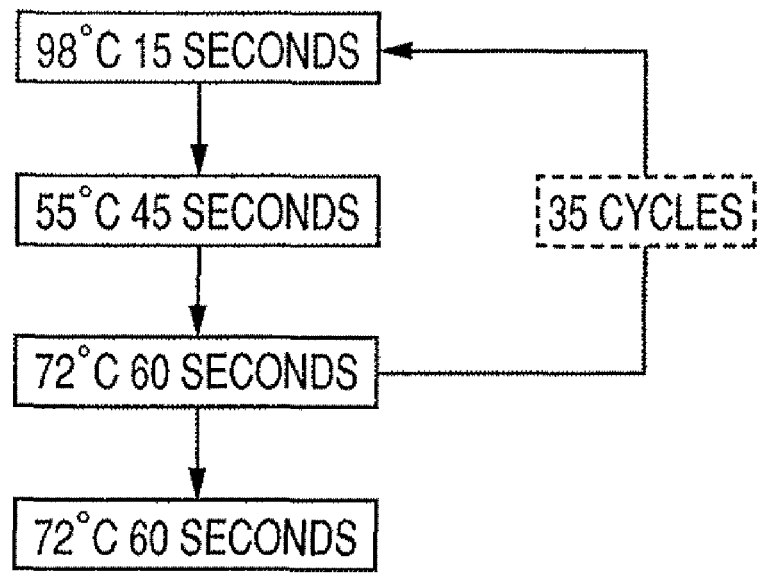
FIG. 2 is a flow chart illustrating a 1st PCR protocol.

The reaction solution having the composition shown in Table 7 was subjected to amplification reaction according to a protocol shown in FIG. 2 using a commercially available thermal cycler.

After the completion of reaction, the amplification products were purified using a purification column (QIAGEN QIAquick PCR Purification Kit) and then quantified.

In this context, obvious nucleic acid amplification was observed, demonstrating the presence of some fungus in the specimens.

6-2. Nucleic Acid Amplification/Labeling: 2nd PCR

2nd PCR was performed using a primer for labeling shown in Table 8.

TABLE 8

Primer for labeling

| Primer Type | Primer Name | Primer Sequence | SEQ ID No: |
|---|---|---|---|
| Primer for Labeling | Cy3-labeled-ITS4 | 5' tcctccgcttattgatatgc 3' | 83 |

Specifically, Cy3 was introduced to the 5' end of the ITS4 primer shown in Table 2, and the resulting primer was used as a primer for labeling.

Figure 3:
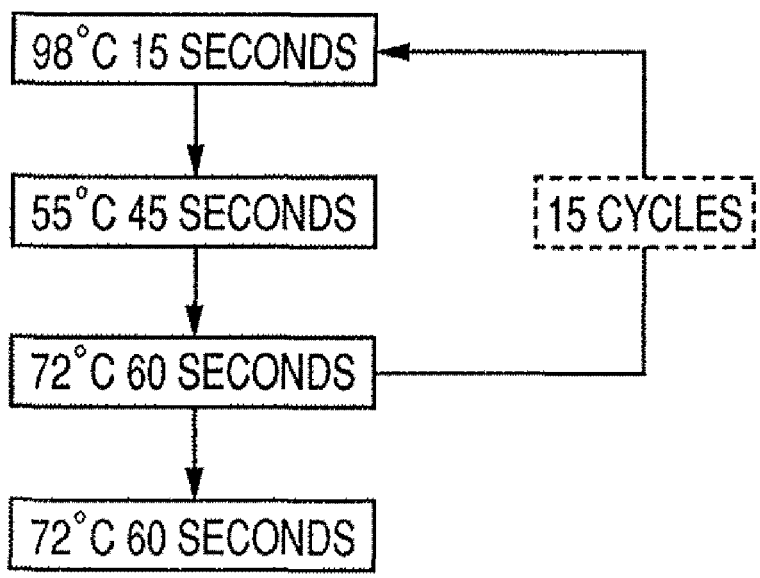
FIG. 3 is a flow chart illustrating a 2nd PCR protocol.

A reaction solution having composition shown in Table 9 below was subjected to amplification reaction according to a protocol shown in FIG. 3 using a commercially available thermal cycler.

TABLE 9

2nd PCR solution composition

| | |
|---|---|
| TaKaRa ExTaq | 25.0 μL |
| Primer or Labeling | 5.0 μL |
| Template DNA (1st PCR Product) | variable (30 ng/tube) |
| Water | up to 50 μL |
| Total | 50 μL |

After the completion of reaction, the amplification products were purified using a purification column (QIAGEN QIAquick PCR Purification Kit) and used as labeled samples.

7. Hybridization 7-1. Hybridization Reaction

Hybridization reaction was performed using the amplified/labeled, specimen-derived nucleic acids obtained by the treatment described in the paragraph '6-2. 2nd PCR' and the DNA chip prepared by the method described in the paragraph '4. Preparation of DNA chip'.

Figure 4:
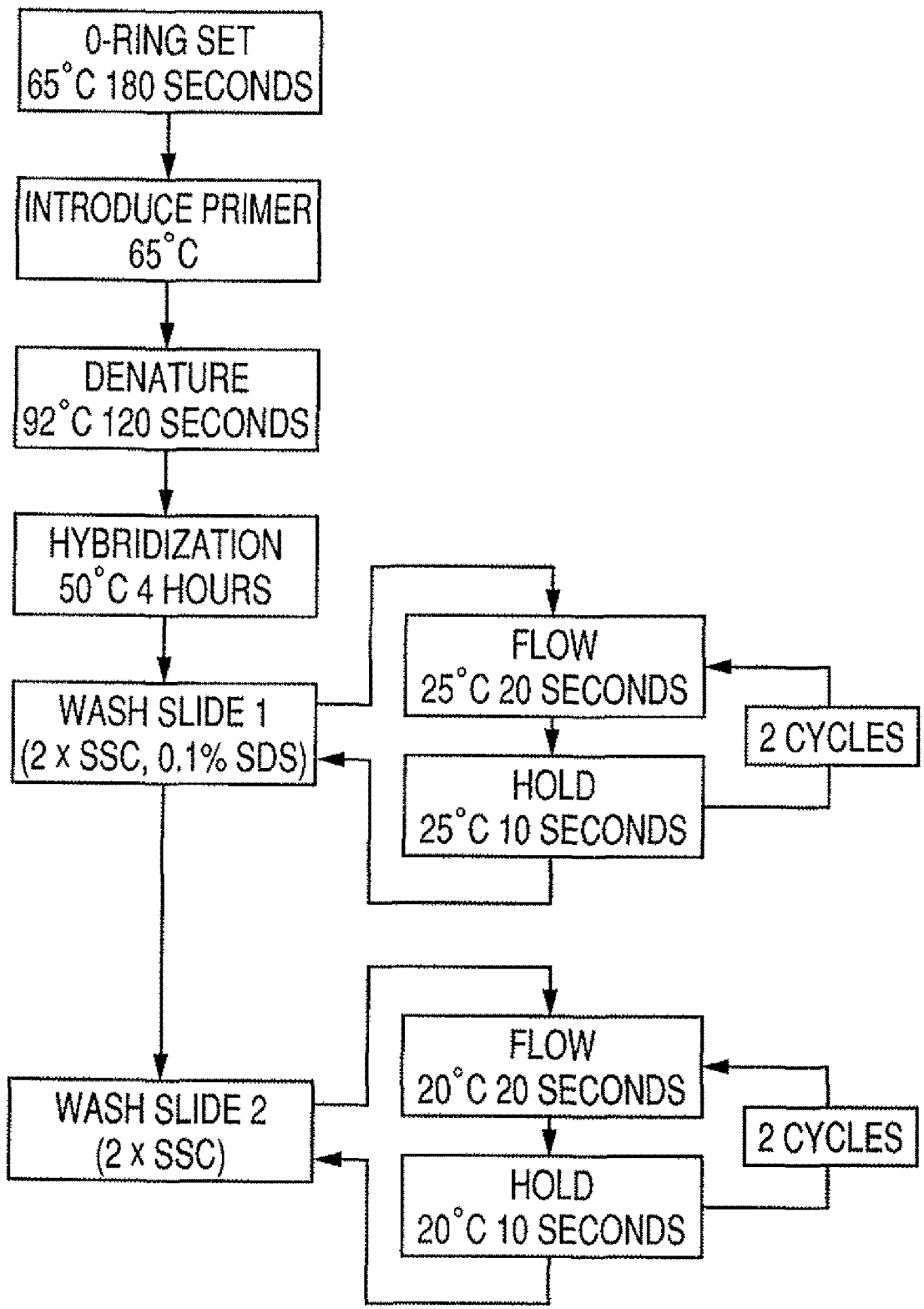
FIG. 4 is a flow chart illustrating a hybridization protocol.

Specifically, hybridization reaction was performed according to a protocol shown in FIG. 4 using a hybridization solution shown in Table 10.

TABLE 10

| | |
|---|---|
| 20 × SSPE | 39.0 μL |
| Formamide | 13.0 μL |
| 25 nM Positive Control | 1.3 μL |
| Water | 13.7 μL |
| Template DNA (2nd PCR Product) | 50 μL |
| 0.5% SDS | 13.0 μL |
| total | 130 μL |

7-2. Fluorescence Measurement

After the completion of the hybridization reaction, fluorescence measurement was performed using a fluorescence detection apparatus (manufactured by Axon, GenePix 4000B).

8. Analysis of Results

Fluorescence intensities obtained by the fluorescence measurement are shown in Tables 11 to 88 below.

TABLE 11

Candida albicans

| Group | Probe Name | SEQ ID No: | 1st Intensity | 1st S/N | 2nd Intensity | 2nd S/N |
|---|---|---|---|---|---|---|
| 1 | P0101 | 1 | 16696.4 | 194.2 | 13186.9 | 269.0 |
| | P0102 | 2 | 25680.8 | 298.6 | 16178.1 | 330.1 |
| | P0103 | 3 | 25387.4 | 295.2 | 18482.3 | 377.1 |
| | P0104 | 4 | 31495.4 | 366.3 | 24985.8 | 509.7 |
| 2 | P0201 | 5 | 92.7 | 1.1 | 52.1 | 1.1 |
| | P0202 | 6 | 953.1 | 11.1 | 196.5 | 4.0 |
| | P0204 | 7 | 651.6 | 7.6 | 166.2 | 3.4 |
| | P0205 | 8 | 77.9 | 0.9 | 46.0 | 0.9 |
| 3 | P0302 | 9 | 75.2 | 0.9 | 44.1 | 0.9 |
| | P0303 | 10 | 79.1 | 0.9 | 43.7 | 0.9 |
| | P0304 | 11 | 78.6 | 0.9 | 43.3 | 0.9 |
| | P0305 | 12 | 76.9 | 0.9 | 45.3 | 0.9 |
| 4 | P0401 | 13 | 83.1 | 1.0 | 44.4 | 0.9 |
| | P0402 | 14 | 81.2 | 0.9 | 45.7 | 0.9 |
| | P0403 | 15 | 87.2 | 1.0 | 43.8 | 0.9 |
| | P0404 | 16 | 436.8 | 5.1 | 97.5 | 2.0 |
| 5 | P0503 | 17 | 78.1 | 0.9 | 43.8 | 0.9 |
| | P0502 | 18 | 80.9 | 0.9 | 43.2 | 0.9 |
| 6 | P0601 | 19 | 80.8 | 0.9 | 44.0 | 0.9 |
| | P0602 | 20 | 73.7 | 0.9 | 43.2 | 0.9 |
| | P0603 | 21 | 76.5 | 0.9 | 44.4 | 0.9 |
| | P0604 | 22 | 79.8 | 0.9 | 46.0 | 0.9 |
| 7 | P0701 | 23 | 82.7 | 1.0 | 44.7 | 0.9 |
| | P0702 | 24 | 114.9 | 1.3 | 47.7 | 1.0 |
| | P0703 | 25 | 80.2 | 0.9 | 45.3 | 0.9 |
| | P0704 | 26 | 84.2 | 1.0 | 44.2 | 0.9 |
| 8 | P0801 | 27 | 105.1 | 1.2 | 50.5 | 1.0 |
| | P0803 | 28 | 74.2 | 0.9 | 47.5 | 1.0 |

TABLE 12

Candida albicans

| Group | Probe Name | SEQ ID No: | 1st Intensity | 1st S/N | 2nd Intensity | 2nd S/N |
|---|---|---|---|---|---|---|
| 9 | P0901 | 29 | 97.2 | 1.1 | 52.0 | 1.1 |
| | P0902 | 30 | 439.1 | 5.1 | 163.9 | 3.3 |
| | P0903 | 31 | 81.0 | 0.9 | 47.2 | 1.0 |
| 10 | P1102 | 32 | 114.3 | 1.3 | 49.8 | 1.0 |
| | P1103 | 33 | 403.5 | 4.7 | 55.3 | 1.1 |
| | P1104 | 34 | 78.9 | 0.9 | 151.3 | 3.1 |
| 11 | P2701 | 35 | 79.4 | 0.9 | 46.1 | 0.9 |
| | P2702 | 36 | 78.8 | 0.9 | 46.7 | 1.0 |
| 12 | P2801 | 37 | 81.8 | 1.0 | 45.9 | 0.9 |
| | P2802 | 38 | 79.1 | 0.9 | 46.8 | 1.0 |
| 13 | P3301 | 39 | 111.1 | 1.3 | 53.8 | 1.1 |
| | P3302 | 40 | 83.9 | 1.0 | 45.2 | 0.9 |
| 14 | P2901 | 41 | 84.2 | 1.0 | 45.9 | 0.9 |
| | P2902 | 42 | 75.4 | 0.9 | 46.6 | 1.0 |
| | P2903 | 43 | 76.9 | 0.9 | 45.1 | 0.9 |
| 15 | P3001 | 44 | 78.2 | 0.9 | 45.2 | 0.9 |
| | P3002 | 45 | 77.4 | 0.9 | 44.8 | 0.9 |
| | P3003 | 46 | 80.3 | 0.9 | 46.4 | 0.9 |
| 16 | P1901 | 47 | 76.8 | 0.9 | 44.4 | 0.9 |
| | P1902 | 48 | 81.5 | 0.9 | 43.6 | 0.9 |
| | P1903 | 49 | 83.2 | 1.0 | 44.4 | 0.9 |
| | P1904 | 50 | 81.6 | 0.9 | 45.1 | 0.9 |
| 17 | P2001 | 51 | 82.0 | 1.0 | 48.9 | 1.0 |
| | P2002 | 52 | 83.4 | 1.0 | 42.7 | 0.9 |
| 18 | P2105 | 53 | 73.8 | 0.9 | 43.4 | 0.9 |
| | P2102 | 54 | 74.4 | 0.9 | 43.8 | 0.9 |
| | P2103 | 55 | 75.4 | 0.9 | 44.4 | 0.9 |

TABLE 13

Candida albicans

| Group | Probe Name | SEQ ID No: | 1st Intensity | 1st S/N | 2nd Intensity | 2nd S/N |
|---|---|---|---|---|---|---|
| 19 | P2205 | 56 | 80.4 | 0.9 | 56.0 | 1.1 |
|  | P2202 | 57 | 75.9 | 0.9 | 43.5 | 0.9 |
|  | P2203 | 58 | 81.3 | 0.9 | 45.5 | 0.9 |
|  | P2204 | 59 | 74.7 | 0.9 | 46.9 | 1.0 |
| 20 | P2302 | 60 | 80.9 | 0.9 | 44.6 | 0.9 |
|  | P2306 | 61 | 82.9 | 1.0 | 43.9 | 0.9 |
|  | P2305 | 62 | 79.9 | 0.9 | 44.8 | 0.9 |
| 21 | P2405 | 63 | 77.3 | 0.9 | 44.7 | 0.9 |
|  | P2402 | 64 | 81.8 | 1.0 | 44.5 | 0.9 |
|  | P2403 | 65 | 75.3 | 0.9 | 44.2 | 0.9 |
| 22 | P2501 | 66 | 77.4 | 0.9 | 45.2 | 0.9 |
|  | P2502 | 67 | 73.6 | 0.9 | 45.7 | 0.9 |
| 23 | P2604 | 68 | 80.9 | 0.9 | 44.4 | 0.9 |
|  | P2601 | 69 | 83.0 | 1.0 | 46.1 | 0.9 |
| 24 | P3101 | 70 | 79.2 | 0.9 | 46.2 | 0.9 |
|  | P3102 | 71 | 79.2 | 0.9 | 44.0 | 0.9 |
| 25 | P3201 | 72 | 75.6 | 0.9 | 45.0 | 0.9 |
|  | P3202 | 73 | 78.5 | 0.9 | 43.4 | 0.9 |
| 26 | P3401 | 74 | 78.7 | 0.9 | 47.3 | 1.0 |
|  | P3402 | 75 | 79.1 | 0.9 | 47.6 | 1.0 |
| 27 | Ptricho1 | 76 | 78.0 | 0.9 | 44.9 | 0.9 |
| 28 | Pfila1 | 77 | 293.4 | 3.4 | 68.3 | 1.4 |
| 29 | Pfungi1 | 78 | 24243.6 | 281.9 | 23631.5 | 482.1 |
|  | Pfungi2 | 79 | 15604.1 | 181.5 | 14957.7 | 305.2 |
|  | Pfungi3 | 80 | 24244.6 | 281.9 | 24264.3 | 495.0 |

TABLE 14

Candida dubliniensis

| Group | Probe Name | SEQ ID No: | 1st Intensity | 1st S/N | 2nd Intensity | 2nd S/N |
|---|---|---|---|---|---|---|
| 1 | P0101 | 1 | 7289.3 | 66.3 | 1477.8 | 31.7 |
|  | P0102 | 2 | 2548.6 | 23.2 | 1046.0 | 22.4 |
|  | P0103 | 3 | 301.3 | 2.7 | 93.9 | 2.0 |
|  | P0104 | 4 | 105.0 | 1.0 | 44.8 | 1.0 |
| 2 | P0201 | 5 | 26899.4 | 244.8 | 14128.3 | 302.7 |
|  | P0202 | 6 | 20909.2 | 190.3 | 10805.3 | 231.5 |
|  | P0204 | 7 | 36715.8 | 334.2 | 19906.9 | 426.6 |
|  | P0205 | 8 | 42855.0 | 390.0 | 15913.4 | 341.0 |
| 3 | P0302 | 9 | 96.9 | 0.9 | 43.1 | 0.9 |
|  | P0303 | 10 | 81.8 | 0.7 | 43.3 | 0.9 |
|  | P0304 | 11 | 86.0 | 0.8 | 43.2 | 0.9 |
|  | P0305 | 12 | 75.5 | 0.7 | 42.6 | 0.9 |
| 4 | P0401 | 13 | 92.1 | 0.8 | 44.7 | 1.0 |
|  | P0402 | 14 | 73.3 | 0.7 | 46.1 | 1.0 |
|  | P0403 | 15 | 81.8 | 0.7 | 47.1 | 1.0 |
|  | P0404 | 16 | 74.3 | 0.7 | 47.4 | 1.0 |
| 5 | P0503 | 17 | 73.3 | 0.7 | 45.3 | 0.9 |
|  | P0502 | 18 | 70.5 | 0.6 | 43.6 | 1.0 |
| 6 | P0601 | 19 | 74.8 | 0.7 | 44.3 | 0.9 |
|  | P0602 | 20 | 75.3 | 0.7 | 43.6 | 0.9 |
|  | P0603 | 21 | 69.2 | 0.6 | 42.7 | 0.9 |
|  | P0604 | 22 | 68.8 | 0.6 | 44.3 | 0.9 |
| 7 | P0701 | 23 | 72.2 | 0.7 | 42.6 | 0.9 |
|  | P0702 | 24 | 113.5 | 1.0 | 47.2 | 1.0 |
|  | P0703 | 25 | 81.6 | 0.7 | 44.5 | 1.0 |
|  | P0704 | 26 | 73.8 | 0.7 | 44.0 | 0.9 |
| 8 | P0801 | 27 | 98.9 | 0.9 | 51.7 | 1.1 |
|  | P0803 | 28 | 72.1 | 0.7 | 44.8 | 1.0 |

TABLE 15

Candida dubliniensis

| Group | Probe Name | SEQ ID No: | 1st Intensity | 1st S/N | 2nd Intensity | 2nd S/N |
|---|---|---|---|---|---|---|
| 9 | P0901 | 29 | 77.7 | 0.7 | 48.2 | 1.0 |
|  | P0902 | 30 | 133.8 | 1.2 | 54.3 | 1.2 |
|  | P0903 | 31 | 68.7 | 0.6 | 45.1 | 1.0 |
| 10 | P1102 | 32 | 81.5 | 0.7 | 49.5 | 1.1 |
|  | P1103 | 33 | 309.7 | 2.8 | 46.7 | 1.0 |
|  | P1104 | 34 | 70.2 | 0.6 | 79.1 | 1.7 |
| 11 | P2701 | 35 | 79.0 | 0.7 | 44.1 | 0.9 |
|  | P2702 | 36 | 70.8 | 0.6 | 43.8 | 0.9 |
| 12 | P2801 | 37 | 73.2 | 0.7 | 43.5 | 0.9 |
|  | P2802 | 38 | 69.9 | 0.6 | 46.6 | 1.0 |
| 13 | P3301 | 39 | 136.2 | 1.2 | 50.5 | 1.1 |
|  | P3302 | 40 | 66.7 | 0.6 | 43.3 | 0.9 |
| 14 | P2901 | 41 | 77.3 | 0.7 | 44.0 | 0.9 |
|  | P2902 | 42 | 72.7 | 0.7 | 43.4 | 0.9 |
|  | P2903 | 43 | 71.2 | 0.6 | 42.3 | 0.9 |
| 15 | P3001 | 44 | 72.1 | 0.7 | 43.7 | 0.9 |
|  | P3002 | 45 | 75.6 | 0.7 | 44.4 | 1.0 |
|  | P3003 | 46 | 73.3 | 0.7 | 42.9 | 0.9 |
| 16 | P1901 | 47 | 73.9 | 0.7 | 44.1 | 0.9 |
|  | P1902 | 48 | 79.5 | 0.7 | 42.3 | 0.9 |
|  | P1903 | 49 | 71.0 | 0.6 | 42.8 | 0.9 |
|  | P1904 | 50 | 74.2 | 0.7 | 44.0 | 0.9 |
| 17 | P2001 | 51 | 77.2 | 0.7 | 46.5 | 1.0 |
|  | P2002 | 52 | 78.3 | 0.7 | 43.7 | 0.9 |
| 18 | P2105 | 53 | 73.4 | 0.7 | 44.3 | 0.9 |
|  | P2102 | 54 | 72.4 | 0.7 | 43.6 | 0.9 |
|  | P2103 | 55 | 74.6 | 0.7 | 43.7 | 0.9 |

TABLE 16

Candida dubliniensis

| Group | Probe Name | SEQ ID No: | 1st Intensity | 1st S/N | 2nd Intensity | 2nd S/N |
|---|---|---|---|---|---|---|
| 19 | P2205 | 56 | 84.2 | 0.8 | 54.9 | 1.2 |
|  | P2202 | 57 | 78.0 | 0.7 | 43.5 | 0.9 |
|  | P2203 | 58 | 74.1 | 0.7 | 44.9 | 1.0 |
|  | P2204 | 59 | 66.2 | 0.6 | 44.3 | 0.9 |
| 20 | P2302 | 60 | 77.0 | 0.7 | 42.5 | 0.9 |
|  | P2306 | 61 | 68.7 | 0.6 | 44.8 | 1.0 |
|  | P2305 | 62 | 73.8 | 0.7 | 43.9 | 0.9 |
| 21 | P2405 | 63 | 73.9 | 0.7 | 43.7 | 0.9 |
|  | P2402 | 64 | 75.7 | 0.7 | 43.2 | 0.9 |
|  | P2403 | 65 | 69.9 | 0.6 | 43.5 | 0.9 |
| 22 | P2501 | 66 | 76.4 | 0.7 | 44.5 | 1.0 |
|  | P2502 | 67 | 71.5 | 0.7 | 45.2 | 1.0 |
| 23 | P2604 | 68 | 75.6 | 0.7 | 43.2 | 0.9 |
|  | P2601 | 69 | 79.3 | 0.7 | 44.8 | 1.0 |
| 24 | P3101 | 70 | 73.8 | 0.7 | 43.7 | 0.9 |
|  | P3102 | 71 | 72.8 | 0.7 | 43.7 | 0.9 |
| 25 | P3201 | 72 | 71.7 | 0.7 | 43.3 | 0.9 |
|  | P3202 | 73 | 76.3 | 0.7 | 43.6 | 0.9 |
| 26 | P3401 | 74 | 75.6 | 0.7 | 46.1 | 1.0 |
|  | P3402 | 75 | 76.4 | 0.7 | 46.5 | 1.0 |
| 27 | Ptricho1 | 76 | 81.2 | 0.7 | 42.4 | 0.9 |
| 28 | Pfila1 | 77 | 521.6 | 4.7 | 82.7 | 1.8 |
| 29 | Pfungi1 | 78 | 27915.0 | 254.1 | 13552.2 | 290.4 |
|  | Pfungi2 | 79 | 17538.3 | 159.6 | 8943.8 | 191.6 |
|  | Pfungi3 | 80 | 29656.3 | 269.9 | 14534.7 | 311.4 |

TABLE 17

Candida glabrata

| Group | Probe Name | SEQ ID No: | 1st Intensity | 1st S/N | 2nd Intensity | 2nd S/N |
|---|---|---|---|---|---|---|
| 1 | P0101 | 1 | 82.9 | 0.8 | 43.2 | 1.0 |
|   | P0102 | 2 | 102.2 | 1.0 | 41.4 | 1.0 |
|   | P0103 | 3 | 111.7 | 1.1 | 42.7 | 1.0 |
|   | P0104 | 4 | 92.1 | 0.9 | 43.4 | 1.0 |
| 2 | P0201 | 5 | 82.9 | 0.8 | 43.2 | 1.0 |
|   | P0202 | 6 | 102.2 | 1.0 | 41.4 | 1.0 |
|   | P0204 | 7 | 111.7 | 1.1 | 42.7 | 1.0 |
|   | P0205 | 8 | 92.1 | 0.9 | 43.4 | 1.0 |
| 3 | P0302 | 9 | 15833.9 | 154.1 | 5529.2 | 127.3 |
|   | P0303 | 10 | 14015.9 | 136.4 | 4610.8 | 106.2 |
|   | P0304 | 11 | 10759.6 | 104.7 | 4087.5 | 94.1 |
|   | P0305 | 12 | 25439.3 | 247.5 | 8721.3 | 200.8 |
| 4 | P0401 | 13 | 97.8 | 1.0 | 43.3 | 1.0 |
|   | P0402 | 14 | 82.5 | 0.8 | 41.9 | 1.0 |
|   | P0403 | 15 | 93.9 | 0.9 | 44.6 | 1.0 |
|   | P0404 | 16 | 111.5 | 1.1 | 44.7 | 1.0 |
| 5 | P0503 | 17 | 89.0 | 0.9 | 41.6 | 1.0 |
|   | P0502 | 18 | 85.3 | 0.8 | 41.6 | 1.0 |
| 6 | P0601 | 19 | 88.6 | 0.9 | 42.6 | 1.0 |
|   | P0602 | 20 | 94.0 | 0.9 | 42.6 | 1.0 |
|   | P0603 | 21 | 86.8 | 0.8 | 41.3 | 1.0 |
|   | P0604 | 22 | 88.8 | 0.9 | 42.7 | 1.0 |
| 7 | P0701 | 23 | 89.7 | 0.9 | 43.1 | 1.0 |
|   | P0702 | 24 | 204.2 | 2.0 | 44.3 | 1.0 |
|   | P0703 | 25 | 82.5 | 0.8 | 41.8 | 1.0 |
|   | P0704 | 26 | 89.0 | 0.9 | 42.4 | 1.0 |
| 8 | P0801 | 27 | 80.4 | 0.8 | 43.8 | 1.0 |
|   | P0803 | 28 | 93.8 | 0.9 | 42.7 | 1.0 |

TABLE 18

Candida glabrata

| Group | Probe Name | SEQ ID No: | 1st Intensity | 1st S/N | 2nd Intensity | 2nd S/N |
|---|---|---|---|---|---|---|
| 9 | P0901 | 29 | 86.3 | 0.8 | 42.2 | 1.0 |
|   | P0902 | 30 | 91.4 | 0.9 | 41.8 | 1.0 |
|   | P0903 | 31 | 100.7 | 1.0 | 42.0 | 1.0 |
| 10 | P1102 | 32 | 92.3 | 0.9 | 45.3 | 1.0 |
|   | P1103 | 33 | 89.9 | 0.9 | 41.8 | 1.0 |
|   | P1104 | 34 | 78.3 | 0.8 | 41.9 | 1.0 |
| 11 | P2701 | 35 | 85.0 | 0.8 | 43.8 | 1.0 |
|   | P2702 | 36 | 83.8 | 0.8 | 42.7 | 1.0 |
| 12 | P2801 | 37 | 91.2 | 0.9 | 41.9 | 1.0 |
|   | P2802 | 38 | 87.3 | 0.8 | 41.7 | 1.0 |
| 13 | P3301 | 39 | 97.6 | 0.9 | 42.0 | 1.0 |
|   | P3302 | 40 | 84.4 | 0.8 | 43.6 | 1.0 |
| 14 | P2901 | 41 | 94.7 | 0.9 | 41.0 | 0.9 |
|   | P2902 | 42 | 88.3 | 0.9 | 41.0 | 0.9 |
|   | P2903 | 43 | 84.7 | 0.8 | 41.0 | 0.9 |
| 15 | P3001 | 44 | 89.7 | 0.9 | 41.8 | 1.0 |
|   | P3002 | 45 | 83.9 | 0.8 | 40.5 | 0.9 |
|   | P3003 | 46 | 85.3 | 0.8 | 42.3 | 1.0 |
| 16 | P1901 | 47 | 83.4 | 0.8 | 41.5 | 1.0 |
|   | P1902 | 48 | 84.9 | 0.8 | 42.1 | 1.0 |
|   | P1903 | 49 | 88.5 | 0.9 | 42.4 | 1.0 |
|   | P1904 | 50 | 87.8 | 0.9 | 44.8 | 1.0 |
| 17 | P2001 | 51 | 94.4 | 0.9 | 44.9 | 1.0 |
|   | P2002 | 52 | 82.9 | 0.8 | 41.6 | 1.0 |
| 18 | P2105 | 53 | 84.3 | 0.8 | 42.1 | 1.0 |
|   | P2102 | 54 | 84.7 | 0.8 | 41.8 | 1.0 |
|   | P2103 | 55 | 93.7 | 0.9 | 41.4 | 1.0 |
| 19 | P2205 | 56 | 91.7 | 0.9 | 55.2 | 1.3 |
|   | P2202 | 57 | 77.9 | 0.8 | 42.1 | 1.0 |
|   | P2203 | 58 | 99.4 | 1.0 | 43.0 | 1.0 |
|   | P2204 | 59 | 85.3 | 0.8 | 41.6 | 1.0 |

TABLE 19

Candida glabrata

| Group | Probe Name | SEQ ID No: | 1st Intensity | 1st S/N | 2nd Intensity | 2nd S/N |
|---|---|---|---|---|---|---|
| 20 | P2302 | 60 | 85.7 | 0.8 | 41.4 | 1.0 |
|   | P2306 | 61 | 89.0 | 0.9 | 41.9 | 1.0 |
|   | P2305 | 62 | 80.9 | 0.8 | 41.8 | 1.0 |
| 21 | P2405 | 63 | 79.7 | 0.8 | 42.4 | 1.0 |
|   | P2402 | 64 | 100.4 | 1.0 | 42.4 | 1.0 |
|   | P2403 | 65 | 87.0 | 0.8 | 42.1 | 1.0 |
| 22 | P2501 | 66 | 85.9 | 0.8 | 42.3 | 1.0 |
|   | P2502 | 67 | 78.1 | 0.8 | 42.1 | 1.0 |
| 23 | P2604 | 68 | 90.7 | 0.9 | 41.1 | 0.9 |
|   | P2601 | 69 | 88.3 | 0.9 | 41.7 | 1.0 |
| 24 | P3101 | 70 | 80.9 | 0.8 | 42.4 | 1.0 |
|   | P3102 | 71 | 91.3 | 0.9 | 41.0 | 0.9 |
| 25 | P3201 | 72 | 93.1 | 0.9 | 41.4 | 1.0 |
|   | P3202 | 73 | 96.4 | 0.9 | 42.8 | 1.0 |
| 26 | P3401 | 74 | 89.0 | 0.9 | 44.6 | 1.0 |
|   | P3402 | 75 | 88.5 | 0.9 | 44.7 | 1.0 |
| 27 | Ptricho1 | 76 | 99.5 | 1.0 | 42.1 | 1.0 |
| 28 | Pfila1 | 77 | 952.4 | 9.3 | 107.6 | 2.5 |
| 29 | Pfungi1 | 78 | 3649.8 | 35.5 | 1439.2 | 33.1 |
|   | Pfungi2 | 79 | 8597.1 | 83.6 | 3522.0 | 81.1 |
|   | Pfungi3 | 80 | 15934.8 | 155.0 | 5841.6 | 134.5 |

TABLE 20

Candida guilliermondii

| Group | Probe Name | SEQ ID No: | 1st Intensity | 1st S/N | 2nd Intensity | 2nd S/N |
|---|---|---|---|---|---|---|
| 1 | P0101 | 1 | 73.1 | 0.8 | 48.8 | 1.0 |
|   | P0102 | 2 | 71.9 | 0.8 | 46.9 | 1.0 |
|   | P0103 | 3 | 167.2 | 1.8 | 71.5 | 1.5 |
|   | P0104 | 4 | 75.6 | 0.8 | 47.4 | 1.0 |
| 2 | P0201 | 5 | 73.1 | 0.8 | 48.8 | 1.0 |
|   | P0202 | 6 | 71.9 | 0.8 | 46.9 | 1.0 |
|   | P0204 | 7 | 167.2 | 1.8 | 71.5 | 1.5 |
|   | P0205 | 8 | 75.6 | 0.8 | 47.4 | 1.0 |
| 3 | P0302 | 9 | 64.1 | 0.7 | 44.4 | 0.9 |
|   | P0303 | 10 | 81.6 | 0.9 | 45.1 | 0.9 |
|   | P0304 | 11 | 79.0 | 0.9 | 46.5 | 1.0 |
|   | P0305 | 12 | 95.2 | 1.0 | 52.7 | 1.1 |
| 4 | P0401 | 13 | 13730.3 | 148.0 | 6877.6 | 142.0 |
|   | P0402 | 14 | 30043.5 | 323.8 | 18892.8 | 390.1 |
|   | P0403 | 15 | 41016.3 | 442.1 | 24412.7 | 504.1 |
|   | P0404 | 16 | 28662.9 | 308.9 | 26971.4 | 557.0 |
| 5 | P0503 | 17 | 60.5 | 0.7 | 45.3 | 1.0 |
|   | P0502 | 18 | 76.3 | 0.8 | 46.4 | 0.9 |
| 6 | P0601 | 19 | 65.2 | 0.7 | 47.2 | 1.0 |
|   | P0602 | 20 | 65.6 | 0.7 | 45.1 | 0.9 |
|   | P0603 | 21 | 63.3 | 0.7 | 45.5 | 0.9 |
|   | P0604 | 22 | 63.5 | 0.7 | 48.7 | 1.0 |
| 7 | P0701 | 23 | 66.7 | 0.7 | 44.9 | 0.9 |
|   | P0702 | 24 | 84.6 | 0.9 | 49.8 | 1.0 |
|   | P0703 | 25 | 67.3 | 0.7 | 44.7 | 0.9 |
|   | P0704 | 26 | 63.9 | 0.7 | 44.9 | 0.9 |
| 8 | P0801 | 27 | 75.8 | 0.8 | 47.1 | 1.0 |
|   | P0803 | 28 | 66.7 | 0.7 | 45.9 | 0.9 |

TABLE 21

*Candida guilliermondii*

| Group | Probe Name | SEQ ID No: | 1st Intensity | S/N | 2nd Intensity | S/N |
|---|---|---|---|---|---|---|
| 9 | P0901 | 29 | 70.5 | 0.8 | 49.1 | 1.0 |
|  | P0902 | 30 | 60.3 | 0.6 | 45.0 | 0.9 |
|  | P0903 | 31 | 57.6 | 0.6 | 44.7 | 0.9 |
| 10 | P1102 | 32 | 105.8 | 1.1 | 51.5 | 1.1 |
|  | P1103 | 33 | 72.6 | 0.8 | 55.5 | 1.1 |
|  | P1104 | 34 | 50.1 | 0.6 | 45.8 | 0.9 |
| 11 | P2701 | 35 | 67.7 | 0.7 | 46.2 | 1.0 |
|  | P2702 | 36 | 60.4 | 0.7 | 45.2 | 0.9 |
| 12 | P2801 | 37 | 66.1 | 0.7 | 47.4 | 1.0 |
|  | P2802 | 38 | 62.4 | 0.7 | 46.4 | 1.0 |
| 13 | P3301 | 39 | 93.0 | 1.0 | 52.2 | 1.1 |
|  | P3302 | 40 | 59.8 | 0.6 | 46.7 | 1.0 |
| 14 | P2901 | 41 | 79.3 | 0.9 | 44.8 | 0.9 |
|  | P2902 | 42 | 68.3 | 0.7 | 46.1 | 1.0 |
|  | P2903 | 43 | 67.1 | 0.7 | 45.3 | 0.9 |
| 15 | P3001 | 44 | 65.8 | 0.7 | 45.7 | 0.9 |
|  | P3002 | 45 | 67.6 | 0.7 | 43.7 | 0.9 |
|  | P3003 | 46 | 62.7 | 0.7 | 44.3 | 0.9 |
| 16 | P1901 | 47 | 69.9 | 0.8 | 45.2 | 0.9 |
|  | P1902 | 48 | 73.2 | 0.8 | 44.8 | 0.9 |
|  | P1903 | 49 | 71.2 | 0.8 | 45.7 | 0.9 |
|  | P1904 | 50 | 68.2 | 0.7 | 46.7 | 1.0 |
| 17 | P2001 | 51 | 70.5 | 0.8 | 49.9 | 1.0 |
|  | P2002 | 52 | 69.4 | 0.7 | 46.8 | 1.0 |
| 18 | P2105 | 53 | 69.8 | 0.8 | 45.9 | 0.9 |
|  | P2102 | 54 | 64.2 | 0.7 | 45.3 | 0.9 |
|  | P2103 | 55 | 66.7 | 0.7 | 43.9 | 0.9 |

TABLE 22

*Candida guilliermondii*

| Group | Probe Name | SEQ ID No: | 1st Intensity | S/N | 2nd Intensity | S/N |
|---|---|---|---|---|---|---|
| 19 | P2205 | 56 | 68.2 | 0.7 | 59.5 | 1.2 |
|  | P2202 | 57 | 64.0 | 0.7 | 45.5 | 0.9 |
|  | P2203 | 58 | 67.2 | 0.7 | 46.3 | 1.0 |
|  | P2204 | 59 | 66.2 | 0.7 | 45.4 | 0.9 |
| 20 | P2302 | 60 | 62.4 | 0.7 | 43.9 | 0.9 |
|  | P2306 | 61 | 67.0 | 0.7 | 46.0 | 0.9 |
|  | P2305 | 62 | 63.6 | 0.7 | 45.4 | 0.9 |
| 21 | P2405 | 63 | 64.4 | 0.7 | 45.0 | 0.9 |
|  | P2402 | 64 | 65.6 | 0.7 | 44.6 | 0.9 |
|  | P2403 | 65 | 66.2 | 0.7 | 45.5 | 0.9 |
| 22 | P2501 | 66 | 64.0 | 0.7 | 45.5 | 0.9 |
|  | P2502 | 67 | 70.8 | 0.8 | 45.1 | 0.9 |
| 23 | P2604 | 68 | 68.9 | 0.7 | 42.7 | 0.9 |
|  | P2601 | 69 | 59.8 | 0.6 | 45.1 | 0.9 |
| 24 | P3101 | 70 | 62.5 | 0.7 | 44.8 | 0.9 |
|  | P3102 | 71 | 62.9 | 0.7 | 45.6 | 0.9 |
| 25 | P3201 | 72 | 77.7 | 0.8 | 45.5 | 0.9 |
|  | P3202 | 73 | 67.6 | 0.7 | 45.4 | 0.9 |
| 26 | P3401 | 74 | 66.9 | 0.7 | 47.9 | 1.0 |
|  | P3402 | 75 | 65.1 | 0.7 | 48.4 | 1.0 |
| 27 | Ptricho1 | 76 | 77.3 | 0.8 | 47.3 | 1.0 |
| 28 | Pfila1 | 77 | 435.5 | 4.7 | 100.4 | 2.1 |
| 29 | Pfungi1 | 78 | 32700.0 | 352.4 | 19752.5 | 407.9 |
|  | Pfungi2 | 79 | 19694.3 | 212.3 | 13434.9 | 277.4 |
|  | Pfungi3 | 80 | 31534.1 | 339.9 | 20458.9 | 422.5 |

TABLE 23

*Candida intermedia*

| Group | Probe Name | SEQ ID No: | 1st Intensity | S/N | 2nd Intensity | S/N |
|---|---|---|---|---|---|---|
| 1 | P0101 | 1 | 68.9 | 0.8 | 46.6 | 1.0 |
|  | P0102 | 2 | 62.7 | 0.8 | 44.0 | 0.9 |
|  | P0103 | 3 | 68.5 | 0.8 | 46.0 | 1.0 |
|  | P0104 | 4 | 62.5 | 0.8 | 45.2 | 0.9 |
| 2 | P0201 | 5 | 68.9 | 0.8 | 46.6 | 1.0 |
|  | P0202 | 6 | 62.7 | 0.8 | 44.0 | 0.9 |
|  | P0204 | 7 | 68.5 | 0.8 | 46.0 | 1.0 |
|  | P0205 | 8 | 62.5 | 0.8 | 45.2 | 0.9 |
| 3 | P0302 | 9 | 61.0 | 0.7 | 44.3 | 0.9 |
|  | P0303 | 10 | 60.9 | 0.7 | 44.7 | 0.9 |
|  | P0304 | 11 | 64.8 | 0.8 | 45.1 | 0.9 |
|  | P0305 | 12 | 61.6 | 0.8 | 44.7 | 0.9 |
| 4 | P0401 | 13 | 67.0 | 0.8 | 46.5 | 1.0 |
|  | P0402 | 14 | 60.5 | 0.7 | 45.2 | 0.9 |
|  | P0403 | 15 | 60.6 | 0.7 | 45.9 | 1.0 |
|  | P0404 | 16 | 62.8 | 0.8 | 48.9 | 1.0 |
| 5 | P0503 | 17 | 51448.9 | 632.4 | 33343.8 | 595.8 |
|  | P0502 | 18 | 50283.5 | 618.0 | 28719.5 | 0.9 |
| 6 | P0601 | 19 | 65.6 | 0.8 | 47.5 | 1.0 |
|  | P0602 | 20 | 58.4 | 0.7 | 44.3 | 0.9 |
|  | P0603 | 21 | 60.3 | 0.7 | 44.8 | 0.9 |
|  | P0604 | 22 | 57.4 | 0.7 | 44.9 | 0.9 |
| 7 | P0701 | 23 | 67.5 | 0.8 | 45.7 | 0.9 |
|  | P0702 | 24 | 68.8 | 0.8 | 45.4 | 0.9 |
|  | P0703 | 25 | 59.6 | 0.7 | 45.1 | 0.9 |
|  | P0704 | 26 | 65.7 | 0.8 | 44.8 | 0.9 |
| 8 | P0801 | 27 | 15715.7 | 193.2 | 9173.3 | 190.3 |
|  | P0803 | 28 | 79.7 | 1.0 | 49.6 | 1.0 |

TABLE 24

*Candida intermedia*

| Group | Probe Name | SEQ ID No: | 1st Intensity | S/N | 2nd Intensity | S/N |
|---|---|---|---|---|---|---|
| 9 | P0901 | 29 | 63.6 | 20.8 | 46.7 | 1.0 |
|  | P0902 | 30 | 56.0 | 0.7 | 45.7 | 0.9 |
|  | P0903 | 31 | 57.5 | 0.7 | 46.3 | 1.0 |
| 10 | P1102 | 32 | 60.4 | 0.7 | 51.3 | 1.1 |
|  | P1103 | 33 | 61.7 | 0.8 | 45.2 | 0.9 |
|  | P1104 | 34 | 55.7 | 0.7 | 45.6 | 0.9 |
| 11 | P2701 | 35 | 61.1 | 0.8 | 44.3 | 0.9 |
|  | P2702 | 36 | 59.6 | 0.7 | 44.5 | 0.9 |
| 12 | P2801 | 37 | 58.7 | 0.7 | 45.3 | 0.9 |
|  | P2802 | 38 | 61.5 | 0.8 | 45.8 | 0.9 |
| 13 | P3301 | 39 | 174.3 | 2.1 | 68.6 | 1.4 |
|  | P3302 | 40 | 60.1 | 0.7 | 45.5 | 0.9 |
| 14 | P2901 | 41 | 67.8 | 0.8 | 46.6 | 1.0 |
|  | P2902 | 42 | 60.1 | 0.7 | 43.9 | 0.9 |
|  | P2903 | 43 | 58.5 | 0.7 | 44.9 | 0.9 |
| 15 | P3001 | 44 | 61.0 | 0.7 | 44.6 | 0.9 |
|  | P3002 | 45 | 62.5 | 0.8 | 45.1 | 0.9 |
|  | P3003 | 46 | 58.6 | 0.7 | 45.9 | 1.0 |
| 16 | P1901 | 47 | 67.1 | 0.8 | 59.6 | 1.2 |
|  | P1902 | 48 | 59.4 | 0.7 | 44.7 | 0.9 |
|  | P1903 | 49 | 56.4 | 0.7 | 46.0 | 1.0 |
|  | P1904 | 50 | 60.2 | 0.7 | 47.4 | 1.0 |
| 17 | P2001 | 51 | 62.1 | 0.8 | 50.3 | 1.0 |
|  | P2002 | 52 | 56.6 | 0.7 | 44.5 | 0.9 |
| 18 | P2105 | 53 | 62.1 | 0.8 | 44.1 | 0.9 |
|  | P2102 | 54 | 61.4 | 0.8 | 44.7 | 0.9 |
|  | P2103 | 55 | 59.7 | 0.7 | 44.9 | 0.9 |

TABLE 25

Candida intermedia

| Group | Probe Name | SEQ ID No: | 1st Intensity | 1st S/N | 2nd Intensity | 2nd S/N |
|---|---|---|---|---|---|---|
| 19 | P2103 | 55 | 59.7 | 0.7 | 44.9 | 0.9 |
|  | P2205 | 56 | 67.1 | 0.8 | 59.6 | 1.2 |
|  | P2202 | 57 | 59.4 | 0.7 | 44.7 | 0.9 |
|  | P2203 | 58 | 56.4 | 0.7 | 46.0 | 1.0 |
|  | P2204 | 59 | 60.2 | 0.7 | 47.4 | 1.0 |
| 20 | P2302 | 60 | 55.5 | 0.7 | 45.7 | 0.9 |
|  | P2306 | 61 | 60.8 | 0.7 | 44.3 | 0.9 |
|  | P2305 | 62 | 60.4 | 0.7 | 45.1 | 0.9 |
| 21 | P2405 | 63 | 60.1 | 0.7 | 44.0 | 0.9 |
|  | P2402 | 64 | 60.7 | 0.7 | 43.6 | 0.9 |
|  | P2403 | 65 | 57.5 | 0.7 | 44.0 | 0.9 |
| 22 | P2501 | 66 | 58.7 | 0.7 | 45.1 | 0.9 |
|  | P2502 | 67 | 57.7 | 0.7 | 45.1 | 0.9 |
| 23 | P2604 | 68 | 62.0 | 0.8 | 43.5 | 0.9 |
|  | P2601 | 69 | 62.4 | 0.8 | 44.6 | 0.9 |
| 24 | P3101 | 70 | 62.8 | 0.8 | 44.5 | 0.9 |
|  | P3102 | 71 | 61.3 | 0.8 | 44.8 | 0.9 |
| 25 | P3201 | 72 | 61.4 | 0.8 | 43.6 | 0.9 |
|  | P3202 | 73 | 62.6 | 0.8 | 44.5 | 0.9 |
| 26 | P3401 | 74 | 61.0 | 0.7 | 48.2 | 1.0 |
|  | P3402 | 75 | 61.1 | 0.8 | 48.5 | 1.0 |
| 27 | Ptricho1 | 76 | 67.5 | 0.8 | 44.8 | 0.9 |
| 28 | Pfila1 | 77 | 145.7 | 1.8 | 51.5 | 1.1 |
| 29 | Pfungi1 | 78 | 42950.4 | 527.9 | 32385.8 | 671.8 |
|  | Pfungi2 | 79 | 37967.1 | 466.7 | 22023.4 | 456.9 |
|  | Pfungi3 | 80 | 26347.8 | 323.8 | 15280.4 | 317.0 |

TABLE 26

Candida kefyr

| Group | Probe Name | SEQ ID No: | 1st Intensity | 1st S/N | 2nd Intensity | 2nd S/N |
|---|---|---|---|---|---|---|
| 1 | P0101 | 1 | 66.0 | 0.8 | 42.7 | 0.9 |
|  | P0102 | 2 | 61.1 | 0.8 | 41.8 | 0.9 |
|  | P0103 | 3 | 65.5 | 0.8 | 44.0 | 1.0 |
|  | P0104 | 4 | 62.8 | 0.8 | 42.2 | 0.9 |
| 2 | P0201 | 5 | 66.0 | 0.8 | 42.7 | 0.9 |
|  | P0202 | 6 | 61.1 | 0.8 | 41.8 | 0.9 |
|  | P0204 | 7 | 65.5 | 0.8 | 44.0 | 1.0 |
|  | P0205 | 8 | 62.8 | 0.8 | 42.2 | 0.9 |
| 3 | P0302 | 9 | 61.3 | 0.8 | 43.0 | 0.9 |
|  | P0303 | 10 | 59.4 | 0.7 | 42.9 | 0.9 |
|  | P0304 | 11 | 59.5 | 0.7 | 43.2 | 0.9 |
|  | P0305 | 12 | 64.5 | 0.8 | 41.1 | 0.9 |
| 4 | P0401 | 13 | 67.2 | 0.8 | 42.3 | 0.9 |
|  | P0402 | 14 | 60.8 | 0.8 | 43.2 | 0.9 |
|  | P0403 | 15 | 60.6 | 0.7 | 42.6 | 0.9 |
|  | P0404 | 16 | 62.6 | 0.8 | 45.2 | 1.0 |
| 5 | P0503 | 17 | 56.6 | 0.7 | 40.7 | 0.9 |
|  | P0502 | 18 | 58.2 | 0.7 | 40.7 | 0.9 |
| 6 | P0601 | 19 | 7074.0 | 87.3 | 2535.2 | 55.8 |
|  | P0602 | 20 | 12223.7 | 150.9 | 4219.5 | 92.9 |
|  | P0603 | 21 | 9000.8 | 111.1 | 2951.8 | 65.0 |
|  | P0604 | 22 | 31074.6 | 383.7 | 14120.9 | 310.8 |
| 7 | P0701 | 23 | 61.1 | 0.8 | 45.8 | 1.0 |
|  | P0702 | 24 | 100.8 | 1.2 | 50.8 | 1.1 |
|  | P0703 | 25 | 60.0 | 0.7 | 41.7 | 0.9 |
|  | P0704 | 26 | 61.6 | 0.8 | 41.8 | 0.9 |
| 8 | P0801 | 27 | 67.6 | 0.8 | 44.8 | 1.0 |
|  | P0803 | 28 | 59.0 | 0.7 | 43.5 | 1.0 |

TABLE 27

Candida kefyr

| Group | Probe Name | SEQ ID No: | 1st Intensity | 1st S/N | 2nd Intensity | 2nd S/N |
|---|---|---|---|---|---|---|
| 9 | P0901 | 29 | 62.7 | 0.8 | 44.6 | 1.0 |
|  | P0902 | 30 | 59.6 | 0.7 | 43.2 | 1.0 |
|  | P0903 | 31 | 61.9 | 0.8 | 42.8 | 0.9 |
| 10 | P1102 | 32 | 60.3 | 0.7 | 45.9 | 1.0 |
|  | P1103 | 33 | 64.6 | 0.8 | 42.0 | 0.9 |
|  | P1104 | 34 | 58.0 | 0.7 | 41.5 | 0.9 |
| 11 | P2701 | 35 | 63.3 | 0.8 | 41.1 | 0.9 |
|  | P2702 | 36 | 60.3 | 0.7 | 42.5 | 0.9 |
| 12 | P2801 | 37 | 62.0 | 0.8 | 41.7 | 0.9 |
|  | P2802 | 38 | 58.4 | 0.7 | 42.1 | 0.9 |
| 13 | P3301 | 39 | 85.3 | 1.1 | 47.6 | 1.0 |
|  | P3302 | 40 | 56.3 | 0.7 | 42.5 | 0.9 |
| 14 | P2901 | 41 | 69.1 | 0.9 | 42.8 | 0.9 |
|  | P2902 | 42 | 58.9 | 0.7 | 41.9 | 0.9 |
|  | P2903 | 43 | 61.2 | 0.8 | 41.8 | 0.9 |
| 15 | P3001 | 44 | 61.3 | 0.8 | 42.0 | 0.9 |
|  | P3002 | 45 | 61.5 | 0.8 | 43.1 | 0.9 |
|  | P3003 | 46 | 58.6 | 0.7 | 42.6 | 0.9 |
| 16 | P1901 | 47 | 67.9 | 0.8 | 42.2 | 0.9 |
|  | P1902 | 48 | 58.9 | 0.7 | 42.8 | 0.9 |
|  | P1903 | 49 | 60.1 | 0.7 | 43.5 | 1.0 |
|  | P1904 | 50 | 59.0 | 0.7 | 43.6 | 1.0 |
| 17 | P2001 | 51 | 61.0 | 0.8 | 44.0 | 1.0 |
|  | P2002 | 52 | 63.1 | 0.8 | 43.1 | 0.9 |
| 18 | P2105 | 53 | 60.2 | 0.7 | 43.7 | 1.0 |
|  | P2102 | 54 | 61.9 | 0.8 | 42.4 | 0.9 |
|  | P2103 | 55 | 61.2 | 0.8 | 41.3 | 0.9 |

TABLE 28

Candida kefyr

| Group | Probe Name | SEQ ID No: | 1st Intensity | 1st S/N | 2nd Intensity | 2nd S/N |
|---|---|---|---|---|---|---|
| 19 | P2205 | 56 | 66.7 | 0.8 | 50.8 | 1.1 |
|  | P2202 | 57 | 60.8 | 0.8 | 41.7 | 0.9 |
|  | P2203 | 58 | 60.3 | 0.7 | 42.2 | 0.9 |
|  | P2204 | 59 | 60.6 | 0.7 | 42.7 | 0.9 |
| 20 | P2302 | 60 | 59.3 | 0.7 | 40.4 | 0.9 |
|  | P2306 | 61 | 59.3 | 0.7 | 40.3 | 0.9 |
|  | P2305 | 62 | 63.0 | 0.8 | 42.6 | 0.9 |
| 21 | P2405 | 63 | 59.3 | 0.7 | 42.3 | 0.9 |
|  | P2402 | 64 | 58.8 | 0.7 | 42.1 | 0.9 |
|  | P2403 | 65 | 59.5 | 0.7 | 42.7 | 0.9 |
| 22 | P2501 | 66 | 63.4 | 0.8 | 41.7 | 0.9 |
|  | P2502 | 67 | 62.4 | 0.8 | 42.3 | 0.9 |
| 23 | P2604 | 68 | 63.0 | 0.8 | 42.8 | 0.9 |
|  | P2601 | 69 | 64.3 | 0.8 | 41.0 | 0.9 |
| 24 | P3101 | 70 | 62.3 | 0.8 | 44.2 | 1.0 |
|  | P3102 | 71 | 60.5 | 0.7 | 41.7 | 0.9 |
| 25 | P3201 | 72 | 58.3 | 0.7 | 42.7 | 0.9 |
|  | P3202 | 73 | 58.8 | 0.7 | 42.2 | 0.9 |
| 26 | P3401 | 74 | 62.3 | 0.8 | 44.0 | 1.0 |
|  | P3402 | 75 | 62.5 | 0.8 | 43.7 | 1.0 |
| 27 | Ptricho1 | 76 | 62.6 | 0.8 | 42.8 | 0.9 |
| 28 | Pfila1 | 77 | 213.8 | 2.6 | 62.7 | 1.4 |
| 29 | Pfungi1 | 78 | 23970.6 | 296.0 | 10604.0 | 233.4 |
|  | Pfungi2 | 79 | 13462.3 | 166.2 | 6275.1 | 138.1 |
|  | Pfungi3 | 80 | 12130.3 | 149.8 | 6773.7 | 149.1 |

TABLE 29

Candida krusei

| Group | Probe Name | SEQ ID No: | 1st Intensity | 1st S/N | 2nd Intensity | 2nd S/N |
|---|---|---|---|---|---|---|
| 1 | P0101 | 1 | 133.4 | 0.8 | 44.4 | 0.9 |
|   | P0102 | 2 | 122.7 | 0.7 | 45.6 | 0.9 |
|   | P0103 | 3 | 103.2 | 0.6 | 47.6 | 1.0 |
|   | P0104 | 4 | 102.8 | 0.6 | 45.6 | 0.9 |
| 2 | P0201 | 5 | 133.4 | 0.8 | 44.4 | 0.9 |
|   | P0202 | 6 | 122.7 | 0.7 | 45.6 | 0.9 |
|   | P0204 | 7 | 103.2 | 0.6 | 47.6 | 1.0 |
|   | P0205 | 8 | 102.8 | 0.6 | 45.6 | 0.9 |
| 3 | P0302 | 9 | 104.5 | 0.6 | 43.8 | 0.9 |
|   | P0303 | 10 | 102.4 | 0.6 | 44.1 | 0.9 |
|   | P0304 | 11 | 107.3 | 0.6 | 44.2 | 0.9 |
|   | P0305 | 12 | 96.4 | 0.6 | 49.6 | 1.0 |
| 4 | P0401 | 13 | 135.0 | 0.8 | 60.9 | 1.2 |
|   | P0402 | 14 | 97.4 | 0.6 | 44.3 | 0.9 |
|   | P0403 | 15 | 110.4 | 0.7 | 43.4 | 0.9 |
|   | P0404 | 16 | 102.8 | 0.6 | 49.6 | 1.0 |
| 5 | P0503 | 17 | 110.8 | 0.7 | 44.8 | 0.9 |
|   | P0502 | 18 | 94.4 | 0.6 | 45.2 | 0.9 |
| 6 | P0601 | 19 | 109.1 | 0.6 | 44.7 | 0.9 |
|   | P0602 | 20 | 102.9 | 0.6 | 44.3 | 0.9 |
|   | P0603 | 21 | 113.3 | 0.7 | 45.9 | 0.9 |
|   | P0604 | 22 | 108.8 | 0.6 | 51.0 | 1.0 |
| 7 | P0701 | 23 | 16550.6 | 98.1 | 23242.4 | 55.8 |
|   | P0702 | 24 | 14238.0 | 84.4 | 15461.0 | 92.9 |
|   | P0703 | 25 | 14560.7 | 86.3 | 10592.3 | 65.0 |
|   | P0704 | 26 | 16313.7 | 96.7 | 9740.5 | 310.8 |
| 8 | P0801 | 27 | 151.2 | 0.9 | 52.7 | 1.1 |
|   | P0803 | 28 | 123.3 | 0.7 | 46.2 | 0.9 |

TABLE 30

Candida krusei

| Group | Probe Name | SEQ ID No: | 1st Intensity | 1st S/N | 2nd Intensity | 2nd S/N |
|---|---|---|---|---|---|---|
| 9 | P0901 | 29 | 117.1 | 0.7 | 46.9 | 0.9 |
|   | P0902 | 30 | 110.1 | 0.7 | 45.9 | 0.9 |
|   | P0903 | 31 | 113.7 | 0.7 | 44.1 | 0.9 |
| 10 | P1102 | 32 | 115.0 | 0.7 | 51.8 | 1.0 |
|   | P1103 | 33 | 114.2 | 0.7 | 42.6 | 0.9 |
|   | P1104 | 34 | 99.4 | 0.6 | 44.6 | 0.9 |
| 11 | P2701 | 35 | 108.0 | 0.6 | 45.1 | 0.9 |
|   | P2702 | 36 | 106.7 | 0.6 | 44.7 | 0.9 |
| 12 | P2801 | 37 | 98.5 | 0.6 | 44.3 | 0.9 |
|   | P2802 | 38 | 104.1 | 0.6 | 46.2 | 0.9 |
| 13 | P3301 | 39 | 143.9 | 0.9 | 50.6 | 1.0 |
|   | P3302 | 40 | 91.4 | 0.5 | 46.0 | 0.9 |
| 14 | P2901 | 41 | 139.8 | 0.8 | 44.2 | 0.9 |
|   | P2902 | 42 | 91.9 | 0.5 | 44.9 | 0.9 |
|   | P2903 | 43 | 92.5 | 0.5 | 45.1 | 0.9 |
| 15 | P3001 | 44 | 85.5 | 0.5 | 45.2 | 0.9 |
|   | P3002 | 45 | 98.6 | 0.6 | 43.1 | 0.9 |
|   | P3003 | 46 | 101.6 | 0.6 | 46.4 | 0.9 |
| 16 | P1901 | 47 | 119.2 | 0.7 | 45.7 | 0.9 |
|   | P1902 | 48 | 116.3 | 0.7 | 45.4 | 0.9 |
|   | P1903 | 49 | 104.6 | 0.6 | 45.5 | 0.9 |
|   | P1904 | 50 | 97.7 | 0.6 | 46.7 | 0.9 |
| 17 | P2001 | 51 | 115.3 | 0.7 | 47.5 | 1.0 |
|   | P2002 | 52 | 122.8 | 0.7 | 45.2 | 0.9 |
| 18 | P2105 | 53 | 116.8 | 0.7 | 45.9 | 0.9 |
|   | P2102 | 54 | 107.5 | 0.6 | 44.8 | 0.9 |
|   | P2103 | 55 | 104.8 | 0.6 | 44.6 | 0.9 |

TABLE 31

Candida krusei

| Group | Probe Name | SEQ ID No: | 1st Intensity | 1st S/N | 2nd Intensity | 2nd S/N |
|---|---|---|---|---|---|---|
| 19 | P2205 | 56 | 129.4 | 0.8 | 62.2 | 1.3 |
|   | P2202 | 57 | 116.6 | 0.7 | 44.0 | 0.9 |
|   | P2203 | 58 | 111.1 | 0.7 | 46.9 | 0.9 |
|   | P2204 | 59 | 98.8 | 0.6 | 43.6 | 0.9 |
| 20 | P2302 | 60 | 115.1 | 0.7 | 42.6 | 0.9 |
|   | P2306 | 61 | 98.4 | 0.6 | 44.5 | 0.9 |
|   | P2305 | 62 | 91.8 | 0.5 | 43.9 | 0.9 |
| 21 | P2405 | 63 | 110.9 | 0.7 | 45.1 | 0.9 |
|   | P2402 | 64 | 110.5 | 0.7 | 44.7 | 0.9 |
|   | P2403 | 65 | 94.2 | 0.6 | 45.4 | 0.9 |
| 22 | P2501 | 66 | 134.3 | 0.8 | 43.4 | 0.9 |
|   | P2502 | 67 | 112.3 | 0.7 | 45.5 | 0.9 |
| 23 | P2604 | 68 | 160.2 | 0.9 | 43.4 | 0.9 |
|   | P2601 | 69 | 117.2 | 0.7 | 44.3 | 0.9 |
| 24 | P3101 | 70 | 96.1 | 0.6 | 43.7 | 0.9 |
|   | P3102 | 71 | 100.4 | 0.6 | 43.9 | 0.9 |
| 25 | P3201 | 72 | 120.9 | 0.7 | 44.5 | 0.9 |
|   | P3202 | 73 | 104.7 | 0.6 | 45.3 | 0.9 |
| 26 | P3401 | 74 | 123.2 | 0.7 | 48.0 | 1.0 |
|   | P3402 | 75 | 114.6 | 0.7 | 48.2 | 1.0 |
| 27 | Ptricho1 | 76 | 119.0 | 0.7 | 43.5 | 0.9 |
| 28 | Pfila1 | 77 | 217.5 | 1.3 | 96.3 | 1.9 |
| 29 | Pfungi1 | 78 | 11741.5 | 69.6 | 16636.0 | 334.4 |
|   | Pfungi2 | 79 | 1007.7 | 6.0 | 1226.3 | 24.6 |
|   | Pfungi3 | 80 | 282.5 | 1.7 | 273.2 | 5.5 |

TABLE 32

Candida lusitaniae

| Group | Probe Name | SEQ ID No: | 1st Intensity | 1st S/N | 2nd Intensity | 2nd S/N |
|---|---|---|---|---|---|---|
| 1 | P0101 | 1 | 87.2 | 0.9 | 53.7 | 1.0 |
|   | P0102 | 2 | 86.6 | 0.9 | 49.3 | 0.9 |
|   | P0103 | 3 | 80.7 | 0.9 | 50.7 | 1.0 |
|   | P0104 | 4 | 86.6 | 0.9 | 50.3 | 1.0 |
| 2 | P0201 | 5 | 87.2 | 0.9 | 53.7 | 1.0 |
|   | P0202 | 6 | 86.6 | 0.9 | 49.3 | 0.9 |
|   | P0204 | 7 | 80.7 | 0.9 | 50.7 | 1.0 |
|   | P0205 | 8 | 86.6 | 0.9 | 50.3 | 1.0 |
| 3 | P0302 | 9 | 85.0 | 0.9 | 48.9 | 0.9 |
|   | P0303 | 10 | 80.0 | 0.9 | 50.0 | 1.0 |
|   | P0304 | 11 | 81.9 | 0.9 | 47.0 | 0.9 |
|   | P0305 | 12 | 74.1 | 0.8 | 48.0 | 0.9 |
| 4 | P0401 | 13 | 81.9 | 0.9 | 47.2 | 0.9 |
|   | P0402 | 14 | 84.0 | 0.9 | 48.1 | 0.9 |
|   | P0403 | 15 | 80.1 | 0.9 | 49.7 | 1.0 |
|   | P0404 | 16 | 82.5 | 0.9 | 51.5 | 1.0 |
| 5 | P0503 | 17 | 86.6 | 0.9 | 47.5 | 0.9 |
|   | P0502 | 18 | 84.2 | 0.9 | 48.6 | 3.3 |
| 6 | P0601 | 19 | 76.3 | 0.8 | 47.9 | 0.9 |
|   | P0602 | 20 | 83.5 | 0.9 | 46.3 | 0.9 |
|   | P0603 | 21 | 78.9 | 0.9 | 46.7 | 0.9 |
|   | P0604 | 22 | 86.3 | 0.9 | 47.5 | 0.9 |
| 7 | P0701 | 23 | 82.0 | 0.9 | 47.2 | 0.9 |
|   | P0702 | 24 | 105.6 | 1.1 | 49.7 | 1.0 |
|   | P0703 | 25 | 80.4 | 0.9 | 48.3 | 0.9 |
|   | P0704 | 26 | 77.6 | 0.8 | 51.3 | 1.0 |
| 8 | P0801 | 27 | 44085.0 | 477.4 | 31133.3 | 598.1 |
|   | P0803 | 28 | 20873.6 | 226.1 | 4959.9 | 95.3 |

TABLE 33

Candida lusitaniae

| Group | Probe Name | SEQ ID No: | 1st Intensity | S/N | 2nd Intensity | S/N |
|---|---|---|---|---|---|---|
| 9 | P0901 | 29 | 87.5 | 0.9 | 50.8 | 1.0 |
|  | P0902 | 30 | 86.5 | 0.9 | 47.4 | 0.9 |
|  | P0903 | 31 | 80.1 | 0.9 | 49.0 | 0.9 |
| 10 | P1102 | 32 | 84.5 | 0.9 | 53.7 | 1.0 |
|  | P1103 | 33 | 89.0 | 1.0 | 45.5 | 0.9 |
|  | P1104 | 34 | 79.0 | 0.9 | 46.7 | 0.9 |
| 11 | P2701 | 35 | 75.9 | 0.8 | 48.2 | 0.9 |
|  | P2702 | 36 | 74.7 | 0.8 | 48.4 | 0.9 |
| 12 | P2801 | 37 | 81.2 | 0.9 | 49.1 | 0.9 |
|  | P2802 | 38 | 79.1 | 0.9 | 47.9 | 0.9 |
| 13 | P3301 | 39 | 188.2 | 2.0 | 65.5 | 1.3 |
|  | P3302 | 40 | 78.3 | 0.8 | 47.7 | 0.9 |
| 14 | P2901 | 41 | 80.7 | 0.9 | 48.2 | 0.9 |
|  | P2902 | 42 | 75.5 | 0.8 | 48.6 | 0.9 |
|  | P2903 | 43 | 78.8 | 0.9 | 48.3 | 0.9 |
| 15 | P3001 | 44 | 84.4 | 0.9 | 48.7 | 0.9 |
|  | P3002 | 45 | 82.8 | 0.9 | 46.3 | 0.9 |
|  | P3003 | 46 | 75.6 | 0.8 | 48.9 | 0.9 |
| 16 | P1901 | 47 | 77.6 | 0.8 | 47.3 | 0.9 |
|  | P1902 | 48 | 81.9 | 0.9 | 47.5 | 0.9 |
|  | P1903 | 49 | 78.9 | 0.9 | 47.8 | 0.9 |
|  | P1904 | 50 | 78.9 | 0.9 | 50.1 | 1.0 |
| 17 | P2001 | 51 | 88.7 | 1.0 | 51.7 | 1.0 |
|  | P2002 | 52 | 85.1 | 0.9 | 48.0 | 0.9 |
| 18 | P2105 | 53 | 82.4 | 0.9 | 47.4 | 0.9 |
|  | P2102 | 54 | 77.7 | 0.8 | 48.9 | 0.9 |
|  | P2103 | 55 | 85.1 | 0.9 | 47.6 | 0.9 |

TABLE 34

Candida lusitaniae

| Group | Probe Name | SEQ ID No: | 1st Intensity | S/N | 2nd Intensity | S/N |
|---|---|---|---|---|---|---|
| 19 | P2205 | 56 | 79.9 | 0.9 | 62.7 | 1.2 |
|  | P2202 | 57 | 86.4 | 0.9 | 47.4 | 0.9 |
|  | P2203 | 58 | 74.8 | 0.8 | 51.2 | 1.0 |
|  | P2204 | 59 | 81.8 | 0.9 | 50.1 | 1.0 |
| 20 | P2302 | 60 | 74.8 | 0.8 | 45.8 | 0.9 |
|  | P2306 | 61 | 75.9 | 0.8 | 48.0 | 0.9 |
|  | P2305 | 62 | 73.4 | 0.8 | 48.4 | 0.9 |
| 21 | P2405 | 63 | 81.4 | 0.9 | 47.7 | 0.9 |
|  | P2402 | 64 | 75.8 | 0.8 | 47.7 | 0.9 |
|  | P2403 | 65 | 76.4 | 0.8 | 46.9 | 0.9 |
| 22 | P2501 | 66 | 79.3 | 0.9 | 45.9 | 0.9 |
|  | P2502 | 67 | 76.6 | 0.8 | 48.3 | 0.9 |
| 23 | P2604 | 68 | 85.3 | 0.9 | 47.1 | 0.9 |
|  | P2601 | 69 | 78.7 | 0.9 | 45.7 | 0.9 |
| 24 | P3101 | 70 | 78.0 | 0.8 | 47.8 | 0.9 |
|  | P3102 | 71 | 75.4 | 0.8 | 52.2 | 1.0 |
| 25 | P3201 | 72 | 81.2 | 0.9 | 46.4 | 0.9 |
|  | P3202 | 73 | 75.7 | 0.8 | 45.0 | 0.9 |
| 26 | P3401 | 74 | 81.6 | 0.9 | 51.7 | 1.0 |
|  | P3402 | 75 | 80.3 | 0.9 | 51.4 | 1.0 |
| 27 | Ptricho1 | 76 | 85.2 | 0.9 | 48.2 | 0.9 |
| 28 | Pfila1 | 77 | 153.9 | 1.7 | 54.5 | 1.0 |
| 29 | Pfungi1 | 78 | 45903.5 | 497.1 | 34330.3 | 659.6 |
|  | Pfungi2 | 79 | 31139.0 | 337.2 | 22431.9 | 431.0 |
|  | Pfungi3 | 80 | 39709.1 | 430.0 | 33279.2 | 639.4 |

TABLE 35

Candida parapsilosis

| Group | Probe Name | SEQ ID No: | 1st Intensity | S/N | 2nd Intensity | S/N |
|---|---|---|---|---|---|---|
| 1 | P0101 | 1 | 68.5 | 0.8 | 45.9 | 0.9 |
|  | P0102 | 2 | 124.1 | 1.5 | 60.5 | 1.2 |
|  | P0103 | 3 | 70.7 | 0.8 | 47.8 | 1.0 |
|  | P0104 | 4 | 67.6 | 0.8 | 44.3 | 0.9 |
| 2 | P0201 | 5 | 68.5 | 0.8 | 45.9 | 0.9 |
|  | P0202 | 6 | 124.1 | 1.5 | 60.5 | 1.2 |
|  | P0204 | 7 | 70.7 | 0.8 | 47.8 | 1.0 |
|  | P0205 | 8 | 67.6 | 0.8 | 44.3 | 0.9 |
| 3 | P0302 | 9 | 63.3 | 0.8 | 43.2 | 0.9 |
|  | P0303 | 10 | 67.5 | 0.8 | 42.6 | 0.9 |
|  | P0304 | 11 | 67.8 | 0.8 | 44.1 | 0.9 |
|  | P0305 | 12 | 60.5 | 0.7 | 42.7 | 0.9 |
| 4 | P0401 | 13 | 65.1 | 0.8 | 42.8 | 0.9 |
|  | P0402 | 14 | 67.4 | 0.8 | 43.9 | 0.9 |
|  | P0403 | 15 | 61.0 | 0.7 Group | 42.5 | 0.9 |
|  | P0404 | 16 | 61.4 | 0.7 | 48.1 | 1.0 |
| 5 | P0503 | 17 | 62.8 | 0.8 | 42.3 | 0.9 |
|  | P0502 | 18 | 67.7 | 0.8 | 41.4 | 0.9 |
| 6 | P0601 | 19 | 65.7 | 0.8 | 42.0 | 0.9 |
|  | P0602 | 20 | 64.9 | 0.8 | 43.0 | 0.9 |
|  | P0603 | 21 | 66.3 | 0.8 | 42.7 | 0.9 |
|  | P0604 | 22 | 60.1 | 0.7 | 45.8 | 0.9 |
| 7 | P0701 | 23 | 63.7 | 0.8 | 43.4 | 0.9 |
|  | P0702 | 24 | 106.2 | 1.3 | 46.9 | 1.0 |
|  | P0703 | 25 | 64.0 | 0.8 | 43.2 | 0.9 |
|  | P0704 | 26 | 61.9 | 0.7 | 42.0 | 0.9 |
| 8 | P0801 | 27 | 66.8 | 0.8 | 45.8 | 0.9 |
|  | P0803 | 28 | 62.9 | 0.8 | 43.7 | 0.9 |

TABLE 36

Candida parapsilosis

| Group | Probe Name | SEQ ID No: | 1st Intensity | S/N | 2nd Intensity | S/N |
|---|---|---|---|---|---|---|
| 9 | P0901 | 29 | 25295.1 | 304.2 | 19584.8 | 404.3 |
|  | P0902 | 30 | 35968.2 | 432.6 | 24796.2 | 511.9 |
|  | P0903 | 31 | 51887.8 | 624.0 | 39702.3 | 819.7 |
| 10 | P1102 | 32 | 141.5 | 1.7 | 52.9 | 1.1 |
|  | P1103 | 33 | 407.8 | 4.9 | 66.3 | 1.4 |
|  | P1104 | 34 | 63.8 | 0.8 | 169.7 | 3.5 |
| 11 | P2701 | 35 | 64.3 | 0.8 | 43.2 | 0.9 |
|  | P2702 | 36 | 60.7 | 0.7 | 43.4 | 0.9 |
| 12 | P2801 | 37 | 63.6 | 0.8 | 45.2 | 0.9 |
|  | P2802 | 38 | 63.2 | 0.8 | 43.4 | 0.9 |
| 13 | P3301 | 39 | 123.3 | 1.5 | 58.7 | 1.2 |
|  | P3302 | 40 | 62.7 | 0.8 | 43.9 | 0.9 |
| 14 | P2901 | 41 | 70.6 | 0.8 | 44.0 | 0.9 |
|  | P2902 | 42 | 62.7 | 0.8 | 43.2 | 0.9 |
|  | P2903 | 43 | 64.4 | 0.8 | 43.3 | 0.9 |
| 15 | P3001 | 44 | 59.8 | 0.7 | 43.5 | 0.9 |
|  | P3002 | 45 | 61.1 | 0.7 | 42.3 | 0.9 |
|  | P3003 | 46 | 60.2 | 0.7 | 42.9 | 0.9 |
| 16 | P1901 | 47 | 63.6 | 0.8 | 42.1 | 0.9 |
|  | P1902 | 48 | 62.8 | 0.8 | 43.2 | 0.9 |
|  | P1903 | 49 | 64.8 | 0.8 | 43.3 | 0.9 |
|  | P1904 | 50 | 68.6 | 0.8 | 44.4 | 0.9 |
| 17 | P2001 | 51 | 67.0 | 0.8 | 48.0 | 1.0 |
|  | P2002 | 52 | 66.3 | 0.8 | 41.8 | 0.9 |
| 18 | P2105 | 53 | 65.5 | 0.8 | 44.2 | 0.9 |
|  | P2102 | 54 | 61.1 | 0.7 | 42.5 | 0.9 |
|  | P2103 | 55 | 66.3 | 0.8 | 43.3 | 0.9 |

TABLE 37

*Candida parapsilosis*

| Group | Probe Name | SEQ ID No: | 1st Intensity | 1st S/N | 2nd Intensity | 2nd S/N |
|---|---|---|---|---|---|---|
| 19 | P2205 | 56 | 64.8 | 0.8 | 57.7 | 1.2 |
|  | P2202 | 57 | 64.4 | 0.8 | 43.0 | 0.9 |
|  | P2203 | 58 | 60.8 | 0.7 | 45.7 | 0.9 |
|  | P2204 | 59 | 63.9 | 0.8 | 43.9 | 0.9 |
| 20 | P2302 | 60 | 60.2 | 0.7 | 41.8 | 0.9 |
|  | P2306 | 61 | 61.9 | 0.7 | 42.2 | 0.9 |
|  | P2305 | 62 | 63.3 | 0.8 | 43.3 | 0.9 |
| 21 | P2405 | 63 | 60.1 | 0.7 | 43.3 | 0.9 |
|  | P2402 | 64 | 60.7 | 0.7 | 42.2 | 0.9 |
|  | P2403 | 65 | 60.5 | 0.7 | 43.5 | 0.9 |
| 22 | P2501 | 66 | 65.8 | 0.8 | 42.2 | 0.9 |
|  | P2502 | 67 | 62.2 | 0.7 | 43.1 | 0.9 |
| 23 | P2604 | 68 | 65.2 | 0.8 | 43.0 | 0.9 |
|  | P2601 | 69 | 63.7 | 0.8 | 43.4 | 0.9 |
| 24 | P3101 | 70 | 65.2 | 0.8 | 42.7 | 0.9 |
|  | P3102 | 71 | 67.0 | 0.8 | 42.1 | 0.9 |
| 25 | P3201 | 72 | 66.3 | 0.8 | 43.0 | 0.9 |
|  | P3202 | 73 | 63.0 | 0.8 | 43.4 | 0.9 |
| 26 | P3401 | 74 | 63.8 | 0.8 | 46.7 | 1.0 |
|  | P3402 | 75 | 63.5 | 0.8 | 46.7 | 1.0 |
| 27 | Ptricho1 | 76 | 83.7 | 1.0 | 49.8 | 1.0 |
| 28 | Pfila1 | 77 | 393.9 | 4.7 | 121.9 | 2.5 |
| 29 | Pfungi1 | 78 | 35575.1 | 427.9 | 25889.6 | 534.5 |
|  | Pfungi2 | 79 | 28593.9 | 343.9 | 19652.0 | 405.7 |
|  | Pfungi3 | 80 | 33345.1 | 401.0 | 24941.6 | 514.9 |

TABLE 38

*Candida tropicalis*

| Group | Probe Name | SEQ ID No: | 1st Intensity | 1st S/N | 2nd Intensity | 2nd S/N |
|---|---|---|---|---|---|---|
| 1 | P0101 | 1 | 71.0 | 0.9 | 46.2 | 1.0 |
|  | P0102 | 2 | 100.3 | 1.2 | 53.4 | 1.1 |
|  | P0103 | 3 | 68.3 | 0.8 | 47.4 | 1.0 |
|  | P0104 | 4 | 69.4 | 0.8 | 46.1 | 1.0 |
| 2 | P0201 | 5 | 71.0 | 0.9 | 46.2 | 1.0 |
|  | P0202 | 6 | 100.3 | 1.2 | 53.4 | 1.1 |
|  | P0204 | 7 | 68.3 | 0.8 | 47.4 | 1.0 |
|  | P0205 | 8 | 69.4 | 0.8 | 46.1 | 1.0 |
| 3 | P0302 | 9 | 60.8 | 0.7 | 43.1 | 0.9 |
|  | P0303 | 10 | 59.8 | 0.7 | 43.0 | 0.9 |
|  | P0304 | 11 | 63.5 | 0.8 | 42.5 | 0.9 |
|  | P0305 | 12 | 58.7 | 0.7 | 42.4 | 0.9 |
| 4 | P0401 | 13 | 57.9 | 0.7 | 43.4 | 0.9 |
|  | P0402 | 14 | 64.9 | 0.8 | 44.3 | 0.9 |
|  | P0403 | 15 | 60.1 | 0.7 | 44.3 | 0.9 |
|  | P0404 | 16 | 62.3 | 0.8 | 46.3 | 1.0 |
| 5 | P0503 | 17 | 57.7 | 0.7 | 42.8 | 0.9 |
|  | P0502 | 18 | 61.5 | 0.8 | 42.7 | 0.9 |
| 6 | P0601 | 19 | 58.9 | 0.7 | 42.4 | 0.9 |
|  | P0602 | 20 | 60.5 | 0.7 | 41.9 | 0.9 |
|  | P0603 | 21 | 62.9 | 0.8 | 42.0 | 0.9 |
|  | P0604 | 22 | 59.0 | 0.7 | 44.5 | 0.9 |
| 7 | P0701 | 23 | 57.6 | 0.7 | 43.2 | 0.9 |
|  | P0702 | 24 | 99.3 | 1.2 | 50.4 | 1.1 |
|  | P0703 | 25 | 53.8 | 0.7 | 42.3 | 0.9 |
|  | P0704 | 26 | 62.1 | 0.8 | 42.6 | 0.9 |
| 8 | P0801 | 27 | 132.8 | 1.6 | 58.0 | 1.2 |
|  | P0803 | 28 | 56.3 | 0.7 | 43.2 | 0.9 |

TABLE 39

*Candida tropicalis*

| Group | Probe Name | SEQ ID No: | 1st Intensity | 1st S/N | 2nd Intensity | 2nd S/N |
|---|---|---|---|---|---|---|
| 9 | P0901 | 29 | 62.8 | 0.8 | 45.8 | 1.0 |
|  | P0902 | 30 | 1195.8 | 14.6 | 219.8 | 4.6 |
|  | P0903 | 31 | 61.0 | 0.7 | 44.9 | 0.9 |
| 10 | P1102 | 32 | 30743.2 | 375.6 | 1168.0 | 24.5 |
|  | P1103 | 33 | 63469.2 | 775.5 | 18432.0 | 387.4 |
|  | P1104 | 34 | 62305.1 | 761.3 | 29945.7 | 629.4 |
| 11 | P2701 | 35 | 61.9 | 0.8 | 42.2 | 0.9 |
|  | P2702 | 36 | 62.1 | 0.8 | 41.0 | 0.9 |
| 12 | P2801 | 37 | 62.8 | 0.8 | 42.0 | 0.9 |
|  | P2802 | 38 | 67.6 | 0.8 | 42.2 | 0.9 |
| 13 | P3301 | 39 | 154.6 | 1.9 | 56.3 | 1.2 |
|  | P3302 | 40 | 57.7 | 0.7 | 41.8 | 0.9 |
| 14 | P2901 | 41 | 65.3 | 0.8 | 42.5 | 0.9 |
|  | P2902 | 42 | 57.5 | 0.7 | 42.6 | 0.9 |
|  | P2903 | 43 | 58.0 | 0.7 | 40.9 | 0.9 |
| 15 | P3001 | 44 | 58.8 | 0.7 | 42.4 | 0.9 |
|  | P3002 | 45 | 60.5 | 0.7 | 42.1 | 0.9 |
|  | P3003 | 46 | 58.3 | 0.7 | 42.9 | 0.9 |
| 16 | P1901 | 47 | 55.9 | 0.7 | 43.4 | 0.9 |
|  | P1902 | 48 | 62.0 | 0.8 | 43.2 | 0.9 |
|  | P1903 | 49 | 63.2 | 0.8 | 43.8 | 0.9 |
|  | P1904 | 50 | 61.3 | 0.7 | 44.7 | 0.9 |
| 17 | P2001 | 51 | 59.3 | 0.7 | 47.8 | 1.0 |
|  | P2002 | 52 | 63.1 | 0.8 | 42.2 | 0.9 |
| 18 | P2105 | 53 | 60.6 | 0.7 | 42.6 | 0.9 |
|  | P2102 | 54 | 57.5 | 0.7 | 43.0 | 0.9 |
|  | P2103 | 55 | 58.6 | 0.7 | 43.0 | 0.9 |

TABLE 40

*Candida tropicalis*

| Group | Probe Name | SEQ ID No: | 1st Intensity | 1st S/N | 2nd Intensity | 2nd S/N |
|---|---|---|---|---|---|---|
| 19 | P2205 | 56 | 61.5 | 0.8 | 55.3 | 1.2 |
|  | P2202 | 57 | 56.9 | 0.7 | 42.0 | 0.9 |
|  | P2203 | 58 | 59.5 | 0.7 | 45.6 | 1.0 |
|  | P2204 | 59 | 60.0 | 0.7 | 43.3 | 0.9 |
| 20 | P2302 | 60 | 57.5 | 0.7 | 42.9 | 0.9 |
|  | P2306 | 61 | 58.8 | 0.7 | 41.6 | 0.9 |
|  | P2305 | 62 | 57.8 | 0.7 | 43.2 | 0.9 |
| 21 | P2405 | 63 | 61.6 | 0.8 | 42.6 | 0.9 |
|  | P2402 | 64 | 60.5 | 0.7 | 42.0 | 0.9 |
|  | P2403 | 65 | 59.4 | 0.7 | 42.9 | 0.9 |
| 22 | P2501 | 66 | 60.1 | 0.7 | 43.0 | 0.9 |
|  | P2502 | 67 | 62.1 | 0.8 | 41.5 | 0.9 |
| 23 | P2604 | 68 | 61.5 | 0.8 | 41.8 | 0.9 |
|  | P2601 | 69 | 57.3 | 0.7 | 41.1 | 0.9 |
| 24 | P3101 | 70 | 58.0 | 0.7 | 42.6 | 0.9 |
|  | P3102 | 71 | 58.9 | 0.7 | 43.1 | 0.9 |
| 25 | P3201 | 72 | 60.7 | 0.7 | 42.1 | 0.9 |
|  | P3202 | 73 | 65.8 | 0.8 | 43.1 | 0.9 |
| 26 | P3401 | 74 | 59.9 | 0.7 | 45.6 | 1.0 |
|  | P3402 | 75 | 59.0 | 0.7 | 45.5 | 1.0 |
| 27 | Ptricho1 | 76 | 70.7 | 0.9 | 43.1 | 0.9 |
| 28 | Pfila1 | 77 | 996.6 | 12.2 | 102.4 | 2.2 |
| 29 | Pfungi1 | 78 | 45728.1 | 558.7 | 21921.2 | 460.8 |
|  | Pfungi2 | 79 | 29767.8 | 363.7 | 14167.7 | 297.8 |
|  | Pfungi3 | 80 | 47139.8 | 576.0 | 22128.7 | 465.1 |

TABLE 41

Trichosporon cutaneum

| Group | Probe Name | SEQ ID No: | 1st Intensity | 1st S/N | 2nd Intensity | 2nd S/N |
|---|---|---|---|---|---|---|
| 1 | P0101 | 1 | 69.1 | 0.8 | 49.1 | 1.0 |
|  | P0102 | 2 | 69.1 | 0.8 | 46.6 | 0.9 |
|  | P0103 | 3 | 82.5 | 0.9 | 51.6 | 1.0 |
|  | P0104 | 4 | 73.9 | 0.8 | 45.4 | 0.9 |
| 2 | P0201 | 5 | 69.1 | 0.8 | 49.1 | 1.0 |
|  | P0202 | 6 | 69.1 | 0.8 | 46.6 | 0.9 |
|  | P0204 | 7 | 82.5 | 0.9 | 51.6 | 1.0 |
|  | P0205 | 8 | 73.9 | 0.8 | 45.4 | 0.9 |
| 3 | P0302 | 9 | 74.4 | 0.8 | 45.8 | 0.9 |
|  | P0303 | 10 | 67.1 | 0.8 | 46.4 | 0.9 |
|  | P0304 | 11 | 71.0 | 0.8 | 47.7 | 0.9 |
|  | P0305 | 12 | 73.2 | 0.8 | 46.6 | 0.9 |
| 4 | P0401 | 13 | 76.8 | 0.9 | 46.2 | 0.9 |
|  | P0402 | 14 | 71.9 | 0.8 | 46.3 | 0.9 |
|  | P0403 | 15 | 65.1 | 0.7 | 45.8 | 0.9 |
|  | P0404 | 16 | 76.0 | 0.9 | 62.2 | 1.2 |
| 5 | P0503 | 17 | 67.4 | 0.8 | 46.4 | 0.9 |
|  | P0502 | 18 | 66.8 | 0.8 | 45.6 | 0.9 |
| 6 | P0601 | 19 | 73.1 | 0.8 | 49.1 | 1.0 |
|  | P0602 | 20 | 66.8 | 0.8 | 45.8 | 0.9 |
|  | P0603 | 21 | 68.6 | 0.8 | 45.2 | 0.9 |
|  | P0604 | 22 | 67.0 | 0.8 | 51.1 | 1.0 |
| 7 | P0701 | 23 | 68.8 | 0.8 | 45.7 | 0.9 |
|  | P0702 | 24 | 322.2 | 3.7 | 74.4 | 1.5 |
|  | P0703 | 25 | 69.2 | 0.8 | 45.2 | 0.9 |
|  | P0704 | 26 | 73.6 | 0.8 | 45.8 | 0.9 |
| 8 | P0801 | 27 | 70.3 | 0.8 | 44.9 | 0.9 |
|  | P0803 | 28 | 65.6 | 0.7 | 46.2 | 0.9 |

TABLE 42

Trichosporon cutaneum

| Group | Probe Name | SEQ ID No: | 1st Intensity | 1st S/N | 2nd Intensity | 2nd S/N |
|---|---|---|---|---|---|---|
| 9 | P0901 | 29 | 74.4 | 0.8 | 49.7 | 1.0 |
|  | P0902 | 30 | 67.8 | 0.8 | 47.4 | 0.9 |
|  | P0903 | 31 | 68.0 | 0.8 | 47.5 | 0.9 |
| 10 | P1102 | 32 | 70.8 | 0.8 | 51.2 | 1.0 |
|  | P1103 | 33 | 67.6 | 0.8 | 45.0 | 0.9 |
|  | P1104 | 34 | 65.9 | 0.8 | 45.1 | 0.9 |
| 11 | P2701 | 35 | 22254.1 | 253.2 | 6292.9 | 124.0 |
|  | P2702 | 36 | 41752.3 | 475.0 | 21600.6 | 425.5 |
| 12 | P2801 | 37 | 484.9 | 5.5 | 172.1 | 3.4 |
|  | P2802 | 38 | 93.0 | 1.1 | 53.8 | 1.1 |
| 13 | P3301 | 39 | 657.1 | 7.5 | 80.2 | 1.6 |
|  | P3302 | 40 | 73.8 | 0.8 | 46.3 | 0.9 |
| 14 | P2901 | 41 | 79.4 | 0.9 | 47.3 | 0.9 |
|  | P2902 | 42 | 75.2 | 0.9 | 46.3 | 0.9 |
|  | P2903 | 43 | 70.1 | 0.8 | 46.8 | 0.9 |
| 15 | P3001 | 44 | 70.6 | 0.8 | 47.8 | 0.9 |
|  | P3002 | 45 | 73.9 | 0.8 | 47.3 | 0.9 |
|  | P3003 | 46 | 65.1 | 0.7 | 46.4 | 0.9 |
| 16 | P1901 | 47 | 70.1 | 0.8 | 45.3 | 0.9 |
|  | P1902 | 48 | 68.3 | 0.8 | 46.2 | 0.9 |
|  | P1903 | 49 | 73.6 | 0.8 | 45.7 | 0.9 |
|  | P1904 | 50 | 68.2 | 0.8 | 50.4 | 1.0 |
| 17 | P2001 | 51 | 75.4 | 0.9 | 49.6 | 1.0 |
|  | P2002 | 52 | 71.3 | 0.8 | 45.2 | 0.9 |
| 18 | P2105 | 53 | 71.0 | 0.8 | 48.5 | 1.0 |
|  | P2102 | 54 | 69.6 | 0.8 | 47.1 | 0.9 |
|  | P2103 | 55 | 73.1 | 0.8 | 46.7 | 0.9 |

TABLE 43

Trichosporon cutaneum

| Group | Probe Name | SEQ ID No: | 1st Intensity | 1st S/N | 2nd Intensity | 2nd S/N |
|---|---|---|---|---|---|---|
| 19 | P2205 | 56 | 72.6 | 0.8 | 63.1 | 1.2 |
|  | P2202 | 57 | 71.1 | 0.8 | 45.5 | 0.9 |
|  | P2203 | 58 | 66.5 | 0.8 | 49.7 | 1.0 |
|  | P2204 | 59 | 71.4 | 0.8 | 49.1 | 1.0 |
| 20 | P2302 | 60 | 70.0 | 0.8 | 46.3 | 0.9 |
|  | P2306 | 61 | 70.1 | 0.8 | 46.6 | 0.9 |
|  | P2305 | 62 | 76.2 | 0.9 | 48.2 | 0.9 |
| 21 | P2405 | 63 | 77.1 | 0.9 | 48.2 | 0.9 |
|  | P2402 | 64 | 71.3 | 0.8 | 44.7 | 0.9 |
|  | P2403 | 65 | 67.7 | 0.8 | 47.4 | 0.9 |
| 22 | P2501 | 66 | 67.4 | 0.8 | 46.1 | 0.9 |
|  | P2502 | 67 | 69.8 | 0.8 | 45.0 | 0.9 |
| 23 | P2604 | 68 | 74.7 | 0.8 | 46.0 | 0.9 |
|  | P2601 | 69 | 66.7 | 0.8 | 47.8 | 0.9 |
| 24 | P3101 | 70 | 74.6 | 0.8 | 46.8 | 0.9 |
|  | P3102 | 71 | 66.1 | 0.8 | 46.8 | 0.9 |
| 25 | P3201 | 72 | 69.7 | 0.8 | 45.4 | 0.9 |
|  | P3202 | 73 | 71.3 | 0.8 | 47.4 | 0.9 |
| 26 | P3401 | 74 | 69.7 | 0.8 | 45.4 | 0.9 |
|  | P3402 | 75 | 71.3 | 0.8 | 47.4 | 0.9 |
| 27 | Ptricho1 | 76 | 71.4 | 0.8 | 45.3 | 0.9 |
| 28 | Pfila1 | 77 | 357.2 | 4.1 | 55.7 | 1.1 |
| 29 | Pfungi1 | 78 | 31168.9 | 354.6 | 11415.2 | 224.9 |
|  | Pfungi2 | 79 | 29610.3 | 336.9 | 11570.7 | 227.9 |
|  | Pfungi3 | 80 | 36895.5 | 419.8 | 14828.1 | 292.1 |

TABLE 44

Trichosporon asahii

| Group | Probe Name | SEQ ID No: | 1st Intensity | 1st S/N | 2nd Intensity | 2nd S/N |
|---|---|---|---|---|---|---|
| 1 | P0101 | 1 | 99.2 | 1.1 | 48.8 | 0.9 |
|  | P0102 | 2 | 117.1 | 1.3 | 49.3 | 0.9 |
|  | P0103 | 3 | 92.4 | 1.0 | 51.3 | 1.0 |
|  | P0104 | 4 | 78.4 | 0.9 | 49.0 | 0.9 |
| 2 | P0201 | 5 | 99.2 | 1.1 | 48.8 | 0.9 |
|  | P0202 | 6 | 117.1 | 1.3 | 49.3 | 0.9 |
|  | P0204 | 7 | 92.4 | 1.0 | 51.3 | 1.0 |
|  | P0205 | 8 | 78.4 | 0.9 | 49.0 | 0.9 |
| 3 | P0302 | 9 | 84.3 | 0.9 | 47.3 | 0.9 |
|  | P0303 | 10 | 84.8 | 0.9 | 45.9 | 0.9 |
|  | P0304 | 11 | 78.2 | 0.9 | 48.6 | 0.9 |
|  | P0305 | 12 | 65.1 | 0.7 | 46.2 | 0.9 |
| 4 | P0401 | 13 | 89.4 | 1.0 | 48.0 | 0.9 |
|  | P0402 | 14 | 79.3 | 0.9 | 47.7 | 0.9 |
|  | P0403 | 15 | 65.8 | 0.7 | 46.7 | 0.9 |
|  | P0404 | 16 | 65.9 | 0.7 | 51.0 | 0.9 |
| 5 | P0503 | 17 | 69.4 | 0.8 | 47.8 | 0.9 |
|  | P0502 | 18 | 75.2 | 0.8 | 47.4 | 0.9 |
| 6 | P0601 | 19 | 73.8 | 0.8 | 48.8 | 0.9 |
|  | P0602 | 20 | 84.3 | 0.9 | 46.5 | 0.9 |
|  | P0603 | 21 | 77.1 | 0.9 | 46.9 | 0.9 |
|  | P0604 | 22 | 67.4 | 0.7 | 47.9 | 0.9 |
| 7 | P0701 | 23 | 73.4 | 0.8 | 46.7 | 0.9 |
|  | P0702 | 24 | 127.4 | 1.4 | 56.2 | 1.0 |
|  | P0703 | 25 | 72.9 | 0.8 | 47.6 | 0.9 |
|  | P0704 | 26 | 71.2 | 0.8 | 48.2 | 0.9 |
| 8 | P0801 | 27 | 69.8 | 0.8 | 46.7 | 0.9 |
|  | P0803 | 28 | 81.4 | 0.9 | 47.8 | 0.9 |

TABLE 45

Trichosporon asahii

| Group | Probe Name | SEQ ID No: | 1st Intensity | S/N | 2nd Intensity | S/N |
|---|---|---|---|---|---|---|
| 9 | P0901 | 29 | 86.2 | 1.0 | 49.7 | 0.9 |
|  | P0902 | 30 | 73.7 | 0.8 | 48.4 | 0.9 |
|  | P0903 | 31 | 69.7 | 0.8 | 47.8 | 0.9 |
| 10 | P1102 | 32 | 75.7 | 0.8 | 52.6 | 1.0 |
|  | P1103 | 33 | 73.7 | 0.8 | 46.9 | 0.9 |
|  | P1104 | 34 | 75.2 | 0.8 | 48.2 | 0.9 |
| 11 | P2701 | 35 | 78.3 | 0.9 | 46.8 | 0.9 |
|  | P2702 | 36 | 78.1 | 0.9 | 47.5 | 0.9 |
| 12 | P2801 | 37 | 7892.4 | 87.7 | 3663.9 | 68.1 |
|  | P2802 | 38 | 3836.0 | 42.6 | 1581.4 | 29.4 |
| 13 | P3301 | 39 | 234.6 | 2.6 | 67.2 | 1.2 |
|  | P3302 | 40 | 71.8 | 0.8 | 46.9 | 0.9 |
| 14 | P2901 | 41 | 104.8 | 1.2 | 51.2 | 1.0 |
|  | P2902 | 42 | 68.9 | 0.8 | 46.7 | 0.9 |
|  | P2903 | 43 | 60.7 | 0.7 | 46.9 | 0.9 |
| 15 | P3001 | 44 | 66.9 | 0.7 | 46.4 | 0.9 |
|  | P3002 | 45 | 67.4 | 0.7 | 47.1 | 0.9 |
|  | P3003 | 46 | 63.2 | 0.7 | 48.6 | 0.9 |
| 16 | P1901 | 47 | 70.9 | 0.8 | 47.8 | 0.9 |
|  | P1902 | 48 | 75.7 | 0.8 | 47.2 | 0.9 |
|  | P1903 | 49 | 71.3 | 0.8 | 46.7 | 0.9 |
|  | P1904 | 50 | 77.4 | 0.9 | 52.3 | 1.0 |
| 17 | P2001 | 51 | 77.4 | 0.9 | 52.5 | 1.0 |
|  | P2002 | 52 | 69.9 | 0.8 | 47.2 | 0.9 |
| 18 | P2105 | 53 | 72.1 | 0.8 | 46.9 | 0.9 |
|  | P2102 | 54 | 65.9 | 0.7 | 47.3 | 0.9 |
|  | P2103 | 55 | 75.9 | 0.8 | 49.8 | 0.9 |

TABLE 46

Trichosporon asahii

| Group | Probe Name | SEQ ID No: | 1st Intensity | S/N | 2nd Intensity | S/N |
|---|---|---|---|---|---|---|
| 19 | P2205 | 56 | 76.7 | 0.9 | 63.2 | 1.2 |
|  | P2202 | 57 | 69.3 | 0.8 | 48.0 | 0.9 |
|  | P2203 | 58 | 70.9 | 0.8 | 48.8 | 0.9 |
|  | P2204 | 59 | 71.1 | 0.8 | 47.9 | 0.9 |
| 20 | P2302 | 60 | 69.4 | 0.8 | 48.3 | 0.9 |
|  | P2306 | 61 | 66.4 | 0.7 | 47.2 | 0.9 |
|  | P2305 | 62 | 73.3 | 0.8 | 48.0 | 0.9 |
| 21 | P2405 | 63 | 68.6 | 0.8 | 46.9 | 0.9 |
|  | P2402 | 64 | 67.7 | 0.8 | 48.3 | 0.9 |
|  | P2403 | 65 | 64.6 | 0.7 | 47.3 | 0.9 |
| 22 | P2501 | 66 | 64.3 | 0.7 | 47.1 | 0.9 |
|  | P2502 | 67 | 69.3 | 0.8 | 49.5 | 0.9 |
| 23 | P2604 | 68 | 66.9 | 0.7 | 46.6 | 0.9 |
|  | P2601 | 69 | 65.1 | 0.7 | 47.1 | 0.9 |
| 24 | P3101 | 70 | 69.6 | 0.8 | 48.8 | 0.9 |
|  | P3102 | 71 | 66.2 | 0.7 | 47.3 | 0.9 |
| 25 | P3201 | 72 | 74.3 | 0.8 | 47.1 | 0.9 |
|  | P3202 | 73 | 70.7 | 0.8 | 46.3 | 0.9 |
| 26 | P3401 | 74 | 71.0 | 0.8 | 50.9 | 0.9 |
|  | P3402 | 75 | 70.6 | 0.8 | 51.0 | 0.9 |
| 27 | Ptricho1 | 76 | 78.8 | 0.9 | 46.9 | 0.9 |
| 28 | Pfila1 | 77 | 97.9 | 1.1 | 47.4 | 0.9 |
| 29 | Pfungi1 | 78 | 10838.1 | 120.4 | 7941.0 | 147.6 |
|  | Pfungi2 | 79 | 13033.1 | 144.8 | 11998.0 | 223.0 |
|  | Pfungi3 | 80 | 13213.0 | 146.8 | 10747.4 | 199.7 |

TABLE 47

Cryptococcus neoformans

| Group | Probe Name | SEQ ID No: | 1st Intensity | S/N | 2nd Intensity | S/N |
|---|---|---|---|---|---|---|
| 1 | P0101 | 1 | 93.3 | 0.8 | 42.4 | 0.9 |
|  | P0102 | 2 | 99.7 | 0.9 | 43.0 | 1.0 |
|  | P0103 | 3 | 99.4 | 0.8 | 49.1 | 1.1 |
|  | P0104 | 4 | 96.0 | 0.8 | 44.8 | 1.0 |
| 2 | P0201 | 5 | 93.3 | 0.8 | 42.4 | 0.9 |
|  | P0202 | 6 | 99.7 | 0.9 | 43.0 | 1.0 |
|  | P0204 | 7 | 99.4 | 0.8 | 49.1 | 1.1 |
|  | P0205 | 8 | 96.0 | 0.8 | 44.8 | 1.0 |
| 3 | P0302 | 9 | 93.6 | 0.8 | 44.0 | 1.0 |
|  | P0303 | 10 | 89.2 | 0.8 | 43.1 | 1.0 |
|  | P0304 | 11 | 89.7 | 0.8 | 44.3 | 1.0 |
|  | P0305 | 12 | 86.5 | 0.7 | 42.8 | 0.9 |
| 4 | P0401 | 13 | 95.8 | 0.8 | 43.2 | 1.0 |
|  | P0402 | 14 | 99.7 | 0.9 | 43.8 | 1.0 |
|  | P0403 | 15 | 86.8 | 0.7 | 43.4 | 1.0 |
|  | P0404 | 16 | 99.9 | 0.9 | 59.8 | 1.3 |
| 5 | P0503 | 17 | 90.7 | 0.8 | 42.6 | 0.9 |
|  | P0502 | 18 | 89.0 | 0.8 | 42.8 | 0.9 |
| 6 | P0601 | 19 | 92.8 | 0.8 | 43.6 | 1.0 |
|  | P0602 | 20 | 93.0 | 0.8 | 44.3 | 1.0 |
|  | P0603 | 21 | 94.3 | 0.8 | 44.7 | 1.0 |
|  | P0604 | 22 | 91.7 | 0.8 | 56.0 | 1.2 |
| 7 | P0701 | 23 | 90.9 | 0.8 | 43.3 | 1.0 |
|  | P0702 | 24 | 147.5 | 1.3 | 45.3 | 1.0 |
|  | P0703 | 25 | 94.6 | 0.8 | 44.0 | 1.0 |
|  | P0704 | 26 | 93.0 | 0.8 | 44.1 | 1.0 |
| 8 | P0801 | 27 | 83.1 | 0.7 | 44.2 | 1.0 |
|  | P0803 | 28 | 88.5 | 0.8 | 42.1 | 0.9 |

TABLE 48

Cryptococcus neoformans

| Group | Probe Name | SEQ ID No: | 1st Intensity | S/N | 2nd Intensity | S/N |
|---|---|---|---|---|---|---|
| 9 | P0901 | 29 | 96.8 | 0.8 | 45.3 | 1.0 |
|  | P0902 | 30 | 94.3 | 0.8 | 45.9 | 1.0 |
|  | P0903 | 31 | 94.6 | 0.8 | 43.3 | 1.0 |
| 10 | P1102 | 32 | 91.8 | 0.8 | 49.0 | 1.1 |
|  | P1103 | 33 | 103.3 | 0.9 | 44.5 | 1.0 |
|  | P1104 | 34 | 92.4 | 0.8 | 43.8 | 1.0 |
| 11 | P2701 | 35 | 96.9 | 0.8 | 43.6 | 1.0 |
|  | P2702 | 36 | 101.8 | 0.9 | 43.3 | 1.0 |
| 12 | P2801 | 37 | 98.3 | 0.8 | 42.4 | 0.9 |
|  | P2802 | 38 | 96.2 | 0.8 | 44.2 | 1.0 |
| 13 | P3301 | 39 | 17041.1 | 145.4 | 2303.8 | 50.9 |
|  | P3302 | 40 | 27959.3 | 238.6 | 3647.3 | 80.6 |
| 14 | P2901 | 41 | 106.0 | 0.9 | 42.3 | 0.9 |
|  | P2902 | 42 | 97.7 | 0.8 | 44.7 | 1.0 |
|  | P2903 | 43 | 98.1 | 0.8 | 43.0 | 1.0 |
| 15 | P3001 | 44 | 97.3 | 0.8 | 43.4 | 1.0 |
|  | P3002 | 45 | 94.4 | 0.8 | 42.1 | 0.9 |
|  | P3003 | 46 | 100.8 | 0.9 | 42.9 | 0.9 |
| 16 | P1901 | 47 | 86.3 | 0.7 | 42.9 | 0.9 |
|  | P1902 | 48 | 94.2 | 0.8 | 43.5 | 1.0 |
|  | P1903 | 49 | 92.7 | 0.8 | 44.2 | 1.0 |
|  | P1904 | 50 | 94.8 | 0.8 | 48.1 | 1.1 |
| 17 | P2001 | 51 | 94.4 | 0.8 | 47.5 | 1.1 |
|  | P2002 | 52 | 90.5 | 0.8 | 43.7 | 1.0 |
| 18 | P2105 | 53 | 90.0 | 0.8 | 43.3 | 1.0 |
|  | P2102 | 54 | 95.4 | 0.8 | 42.4 | 0.9 |
|  | P2103 | 55 | 99.6 | 0.8 | 44.0 | 1.0 |

TABLE 49

*Cryptococcus neoformans*

| Group | Probe Name | SEQ ID No: | 1st Intensity | 1st S/N | 2nd Intensity | 2nd S/N |
|---|---|---|---|---|---|---|
|  | P2103 | 55 | 99.6 | 0.8 | 44.0 | 1.0 |
| 19 | P2205 | 56 | 95.9 | 0.8 | 56.5 | 1.2 |
|  | P2202 | 57 | 93.8 | 0.8 | 43.1 | 1.0 |
|  | P2203 | 58 | 91.6 | 0.8 | 48.0 | 1.1 |
|  | P2204 | 59 | 101.2 | 0.9 | 43.5 | 1.0 |
| 20 | P2302 | 60 | 96.0 | 0.8 | 41.8 | 0.9 |
|  | P2306 | 61 | 98.3 | 0.8 | 44.0 | 1.0 |
|  | P2305 | 62 | 93.0 | 0.8 | 44.0 | 1.0 |
| 21 | P2405 | 63 | 94.4 | 0.8 | 43.8 | 1.0 |
|  | P2402 | 64 | 100.5 | 0.9 | 43.5 | 1.0 |
|  | P2403 | 65 | 100.4 | 0.9 | 43.6 | 1.0 |
| 22 | P2501 | 66 | 94.7 | 0.8 | 42.6 | 0.9 |
|  | P2502 | 67 | 113.4 | 1.0 | 46.3 | 1.0 |
| 23 | P2604 | 68 | 89.8 | 0.8 | 42.9 | 0.9 |
|  | P2601 | 69 | 96.7 | 0.8 | 43.0 | 1.0 |
| 24 | P3101 | 70 | 94.4 | 0.8 | 43.8 | 1.0 |
|  | P3102 | 71 | 97.6 | 0.8 | 43.8 | 1.0 |
| 25 | P3201 | 72 | 95.3 | 0.8 | 43.6 | 1.0 |
|  | P3202 | 73 | 95.8 | 0.8 | 42.6 | 0.9 |
| 26 | P3401 | 74 | 94.5 | 0.8 | 46.8 | 1.0 |
|  | P3402 | 75 | 95.8 | 0.8 | 46.8 | 1.0 |
| 27 | Ptricho1 | 76 | 100.0 | 0.9 | 42.8 | 0.9 |
| 28 | Pfila1 | 77 | 466.3 | 4.0 | 54.6 | 1.2 |
| 29 | Pfungi1 | 78 | 16278.7 | 138.9 | 2023.5 | 44.7 |
|  | Pfungi2 | 79 | 11111.6 | 94.8 | 1295.3 | 28.6 |
|  | Pfungi3 | 80 | 4779.6 | 40.8 | 309.8 | 6.8 |

TABLE 50

*Aspergillus fumigatus*

| Group | Probe Name | SEQ ID No: | 1st Intensity | 1st S/N | 2nd Intensity | 2nd S/N |
|---|---|---|---|---|---|---|
| 1 | P0101 | 1 | 78.4 | 0.7 | 52.5 | 0.7 |
|  | P0102 | 2 | 82.8 | 0.8 | 51.8 | 0.7 |
|  | P0103 | 3 | 80.7 | 0.8 | 60.0 | 0.8 |
|  | P0104 | 4 | 80.2 | 0.8 | 56.3 | 0.8 |
| 2 | P0201 | 5 | 74.4 | 0.7 | 53.6 | 0.7 |
|  | P0202 | 6 | 73.9 | 0.7 | 66.1 | 0.9 |
|  | P0204 | 7 | 78.4 | 0.7 | 98.0 | 1.3 |
|  | P0205 | 8 | 74.2 | 0.7 | 58.1 | 0.8 |
| 3 | P0302 | 9 | 76.4 | 0.7 | 56.1 | 0.8 |
|  | P0303 | 10 | 75.9 | 0.7 | 56.5 | 0.8 |
|  | P0304 | 11 | 79.1 | 0.7 | 62.1 | 0.8 |
|  | P0305 | 12 | 78.4 | 0.7 | 53.1 | 0.7 |
| 4 | P0401 | 13 | 83.8 | 0.8 | 60.0 | 0.8 |
|  | P0402 | 14 | 77.2 | 0.7 | 64.0 | 0.9 |
|  | P0403 | 15 | 77.9 | 0.7 | 53.4 | 0.7 |
|  | P0404 | 16 | 79.0 | 0.7 | 66.7 | 0.9 |
| 5 | P0503 | 17 | 76.0 | 0.7 | 60.5 | 0.8 |
|  | P0502 | 18 | 71.4 | 0.7 | 56.8 | 0.7 |
| 6 | P0601 | 19 | 76.4 | 0.7 | 55.1 | 0.8 |
|  | P0602 | 20 | 81.8 | 0.8 | 55.5 | 0.8 |
|  | P0603 | 21 | 75.2 | 0.7 | 55.4 | 0.8 |
|  | P0604 | 22 | 76.4 | 0.7 | 54.7 | 0.7 |
| 7 | P0701 | 23 | 75.0 | 0.7 | 54.1 | 0.7 |
|  | P0702 | 24 | 194.0 | 1.8 | 193.9 | 2.6 |
|  | P0703 | 25 | 77.4 | 0.7 | 55.3 | 0.8 |
|  | P0704 | 26 | 79.9 | 0.7 | 61.4 | 0.8 |
| 8 | P0801 | 27 | 78.7 | 0.7 | 54.2 | 0.7 |
|  | P0803 | 28 | 74.7 | 0.7 | 63.3 | 0.9 |

TABLE 51

*Aspergillus fumigatus*

| Group | Probe Name | SEQ ID No: | 1st Intensity | 1st S/N | 2nd Intensity | 2nd S/N |
|---|---|---|---|---|---|---|
| 9 | P0901 | 29 | 77.7 | 0.7 | 55.8 | 0.8 |
|  | P0902 | 30 | 77.5 | 0.7 | 55.3 | 0.8 |
|  | P0903 | 31 | 75.3 | 0.7 | 52.7 | 0.7 |
| 10 | P1102 | 32 | 71.7 | 0.7 | 59.9 | 0.8 |
|  | P1103 | 33 | 79.5 | 0.7 | 52.2 | 0.7 |
|  | P1104 | 34 | 79.8 | 0.7 | 53.2 | 0.7 |
| 11 | P2701 | 35 | 79.0 | 0.7 | 52.4 | 0.7 |
|  | P2702 | 36 | 77.3 | 0.7 | 58.2 | 0.8 |
| 12 | P2801 | 37 | 77.5 | 0.7 | 55.0 | 0.7 |
|  | P2802 | 38 | 77.1 | 0.7 | 85.2 | 1.2 |
| 13 | P3301 | 39 | 125.0 | 1.2 | 160.6 | 2.2 |
|  | P3302 | 40 | 73.6 | 0.7 | 52.1 | 0.7 |
| 14 | P2901 | 41 | 7819.0 | 73.2 | 4982.6 | 67.8 |
|  | P2902 | 42 | 18393.0 | 172.2 | 7355.3 | 100.1 |
|  | P2903 | 43 | 15018.0 | 140.6 | 25513.5 | 347.4 |
| 15 | P3001 | 44 | 265.3 | 2.5 | 332.0 | 4.5 |
|  | P3002 | 45 | 85.9 | 0.8 | 69.0 | 0.9 |
|  | P3003 | 46 | 77.2 | 0.7 | 58.0 | 0.8 |
| 16 | P1901 | 47 | 75.6 | 0.7 | 57.8 | 0.8 |
|  | P1902 | 48 | 77.3 | 0.7 | 58.0 | 0.8 |
|  | P1903 | 49 | 78.4 | 0.7 | 56.7 | 0.8 |
|  | P1904 | 50 | 78.1 | 0.7 | 84.7 | 1.2 |
| 17 | P2001 | 51 | 84.2 | 0.8 | 62.6 | 0.9 |
|  | P2002 | 52 | 79.1 | 0.7 | 57.8 | 0.8 |
| 18 | P2105 | 53 | 74.3 | 0.7 | 61.4 | 0.8 |
|  | P2102 | 54 | 73.6 | 0.7 | 55.2 | 0.8 |
|  | P2103 | 55 | 74.8 | 0.7 | 57.3 | 0.8 |

TABLE 52

*Aspergillus fumigatus*

| Group | Probe Name | SEQ ID No: | 1st Intensity | 1st S/N | 2nd Intensity | 2nd S/N |
|---|---|---|---|---|---|---|
| 19 | P2205 | 56 | 82.7 | 0.8 | 68.7 | 0.9 |
|  | P2202 | 57 | 72.6 | 0.7 | 53.4 | 0.7 |
|  | P2203 | 58 | 74.2 | 0.7 | 54.7 | 0.7 |
|  | P2204 | 59 | 72.6 | 0.7 | 59.6 | 0.8 |
| 20 | P2302 | 60 | 74.6 | 0.7 | 52.3 | 0.7 |
|  | P2306 | 61 | 78.7 | 0.7 | 56.3 | 0.8 |
|  | P2305 | 62 | 74.3 | 0.7 | 58.7 | 0.8 |
| 21 | P2405 | 63 | 77.3 | 0.7 | 54.7 | 0.7 |
|  | P2402 | 64 | 75.3 | 0.7 | 52.6 | 0.7 |
|  | P2403 | 65 | 76.4 | 0.7 | 56.8 | 0.8 |
| 22 | P2501 | 66 | 76.5 | 0.7 | 50.6 | 0.7 |
|  | P2502 | 67 | 88.7 | 0.8 | 238.1 | 3.2 |
| 23 | P2604 | 68 | 76.8 | 0.7 | 55.8 | 0.8 |
|  | P2601 | 69 | 81.3 | 0.8 | 51.2 | 0.7 |
| 24 | P3101 | 70 | 79.1 | 0.7 | 52.7 | 0.7 |
|  | P3102 | 71 | 77.4 | 0.7 | 52.4 | 0.7 |
| 25 | P3201 | 72 | 74.7 | 0.7 | 56.4 | 0.8 |
|  | P3202 | 73 | 75.3 | 0.7 | 55.4 | 0.7 |
| 26 | P3401 | 74 | 75.8 | 0.7 | 58.5 | 0.8 |
|  | P3402 | 75 | 76.7 | 0.7 | 57.5 | 0.8 |
| 27 | Ptricho1 | 76 | 83.0 | 0.8 | 73.7 | 1.0 |
| 28 | Pfila1 | 77 | 35921.3 | 336.3 | 21171.4 | 288.2 |
| 29 | Pfungi1 | 78 | 20169.0 | 188.9 | 5202.9 | 70.8 |
|  | Pfungi2 | 79 | 14529.7 | 136.0 | 4730.4 | 64.4 |
|  | Pfungi3 | 80 | 9107.6 | 85.3 | 4169.4 | 56.8 |

TABLE 53

Aspergillus niger

| Group | Probe Name | SEQ ID No: | 1st Intensity | 1st S/N | 2nd Intensity | 2nd S/N |
|---|---|---|---|---|---|---|
| 1 | P0101 | 1 | 95.4 | 0.8 | 47.9 | 0.9 |
|  | P0102 | 2 | 101.8 | 0.9 | 48.8 | 1.0 |
|  | P0103 | 3 | 101.5 | 0.9 | 50.6 | 1.0 |
|  | P0104 | 4 | 94.6 | 0.8 | 48.0 | 0.9 |
| 2 | P0201 | 5 | 95.4 | 0.8 | 47.9 | 0.9 |
|  | P0202 | 6 | 101.8 | 0.9 | 48.8 | 1.0 |
|  | P0204 | 7 | 101.5 | 0.9 | 50.6 | 1.0 |
|  | P0205 | 8 | 94.6 | 0.8 | 48.0 | 0.9 |
| 3 | P0302 | 9 | 101.9 | 0.9 | 48.2 | 0.9 |
|  | P0303 | 10 | 91.9 | 0.8 | 46.9 | 0.9 |
|  | P0304 | 11 | 91.8 | 0.8 | 47.7 | 0.9 |
|  | P0305 | 12 | 87.3 | 0.7 | 45.8 | 0.9 |
| 4 | P0401 | 13 | 100.1 | 0.8 | 46.8 | 0.9 |
|  | P0402 | 14 | 90.5 | 0.8 | 48.9 | 1.0 |
|  | P0403 | 15 | 96.5 | 0.8 | 47.1 | 0.9 |
|  | P0404 | 16 | 108.7 | 0.9 | 56.8 | 1.1 |
| 5 | P0503 | 17 | 87.3 | 0.7 | 47.5 | 0.9 |
|  | P0502 | 18 | 90.5 | 0.8 | 47.4 | 0.9 |
| 6 | P0601 | 19 | 89.4 | 0.8 | 48.8 | 1.0 |
|  | P0602 | 20 | 102.3 | 0.9 | 46.2 | 0.9 |
|  | P0603 | 21 | 83.9 | 0.7 | 46.0 | 0.9 |
|  | P0604 | 22 | 91.7 | 0.8 | 51.0 | 1.0 |
| 7 | P0701 | 23 | 102.4 | 0.9 | 46.0 | 0.9 |
|  | P0702 | 24 | 156.2 | 1.3 | 73.9 | 1.5 |
|  | P0703 | 25 | 86.0 | 0.7 | 47.6 | 0.9 |
|  | P0704 | 26 | 96.2 | 0.8 | 48.2 | 1.0 |
| 8 | P0801 | 27 | 91.2 | 0.8 | 47.2 | 0.9 |
|  | P0803 | 28 | 89.0 | 0.7 | 48.2 | 0.9 |

TABLE 54

Aspergillus niger

| Group | Probe Name | SEQ ID No: | 1st Intensity | 1st S/N | 2nd Intensity | 2nd S/N |
|---|---|---|---|---|---|---|
| 9 | P0901 | 29 | 99.8 | 0.8 | 51.3 | 1.0 |
|  | P0902 | 30 | 93.3 | 0.8 | 48.8 | 1.0 |
|  | P0903 | 31 | 85.4 | 0.7 | 47.6 | 0.9 |
| 10 | P1102 | 32 | 97.0 | 0.8 | 54.7 | 1.1 |
|  | P1103 | 33 | 99.4 | 0.8 | 48.0 | 0.9 |
|  | P1104 | 34 | 92.7 | 0.8 | 47.7 | 0.9 |
| 11 | P2701 | 35 | 104.7 | 0.9 | 47.2 | 0.9 |
|  | P2702 | 36 | 91.7 | 0.8 | 47.0 | 0.9 |
| 12 | P2801 | 37 | 101.3 | 0.9 | 3927.8 | 77.5 |
|  | P2802 | 38 | 105.0 | 0.9 | 2177.0 | 42.9 |
| 13 | P3301 | 39 | 111.8 | 0.9 | 80.1 | 1.6 |
|  | P3302 | 40 | 94.8 | 0.8 | 48.4 | 1.0 |
| 14 | P2901 | 41 | 135.6 | 1.1 | 59.2 | 1.2 |
|  | P2902 | 42 | 109.4 | 0.9 | 48.5 | 1.0 |
|  | P2903 | 43 | 103.6 | 0.9 | 48.6 | 1.0 |
| 15 | P3001 | 44 | 15092.9 | 126.7 | 3512.2 | 69.3 |
|  | P3002 | 45 | 13733.8 | 115.3 | 586.9 | 11.6 |
|  | P3003 | 46 | 5765.8 | 48.4 | 1566.4 | 30.9 |
| 16 | P1901 | 47 | 105.6 | 0.9 | 50.9 | 1.0 |
|  | P1902 | 48 | 104.1 | 0.9 | 47.6 | 0.9 |
|  | P1903 | 49 | 94.2 | 0.8 | 47.0 | 0.9 |
|  | P1904 | 50 | 109.4 | 0.9 | 48.0 | 0.9 |
| 17 | P2001 | 51 | 100.3 | 0.8 | 53.4 | 1.1 |
|  | P2002 | 52 | 107.4 | 0.9 | 47.1 | 0.9 |
| 18 | P2105 | 53 | 107.5 | 0.9 | 49.6 | 1.0 |
|  | P2102 | 54 | 94.0 | 0.8 | 45.6 | 0.9 |
|  | P2103 | 55 | 102.7 | 0.9 | 46.2 | 0.9 |

TABLE 55

Aspergillus niger

| Group | Probe Name | SEQ ID No: | 1st Intensity | 1st S/N | 2nd Intensity | 2nd S/N |
|---|---|---|---|---|---|---|
| 19 | P2205 | 56 | 106.6 | 0.9 | 63.0 | 1.2 |
|  | P2202 | 57 | 105.3 | 0.9 | 47.0 | 0.9 |
|  | P2203 | 58 | 86.2 | 0.7 | 49.2 | 1.0 |
|  | P2204 | 59 | 110.1 | 0.9 | 47.5 | 0.9 |
| 20 | P2302 | 60 | 95.0 | 0.8 | 47.5 | 0.9 |
|  | P2306 | 61 | 105.1 | 0.9 | 46.6 | 0.9 |
|  | P2305 | 62 | 97.7 | 0.8 | 48.3 | 1.0 |
| 21 | P2405 | 63 | 104.4 | 0.9 | 47.4 | 0.9 |
|  | P2402 | 64 | 96.9 | 0.8 | 47.5 | 0.9 |
|  | P2403 | 65 | 95.1 | 0.8 | 49.1 | 1.0 |
| 22 | P2501 | 66 | 104.1 | 0.9 | 46.7 | 0.9 |
|  | P2502 | 67 | 103.8 | 0.9 | 50.2 | 1.0 |
| 23 | P2604 | 68 | 84.3 | 0.7 | 46.0 | 0.9 |
|  | P2601 | 69 | 103.4 | 0.9 | 46.6 | 0.9 |
| 24 | P3101 | 70 | 107.2 | 0.9 | 47.9 | 0.9 |
|  | P3102 | 71 | 96.6 | 0.8 | 49.3 | 1.0 |
| 25 | P3201 | 72 | 97.6 | 0.8 | 48.5 | 1.0 |
|  | P3202 | 73 | 87.5 | 0.7 | 46.3 | 0.9 |
| 26 | P3401 | 74 | 98.5 | 0.8 | 50.5 | 1.0 |
|  | P3402 | 75 | 102.3 | 0.9 | 50.7 | 1.0 |
| 27 | Ptricho1 | 76 | 102.8 | 0.9 | 48.3 | 1.0 |
| 28 | Pfila1 | 77 | 29035.8 | 243.8 | 8430.3 | 166.3 |
| 29 | Pfungi1 | 78 | 2645.2 | 22.2 | 8603.9 | 169.7 |
|  | Pfungi2 | 79 | 16245.0 | 136.4 | 13774.8 | 271.7 |
|  | Pfungi3 | 80 | 8712.2 | 73.2 | 13746.0 | 271.1 |

TABLE 56

Epidermophyton floccosum

| Group | Probe Name | SEQ ID No: | 1st Intensity | 1st S/N | 2nd Intensity | 2nd S/N |
|---|---|---|---|---|---|---|
| 1 | P0101 | 1 | 98.3 | 1.1 | 48.6 | 0.9 |
|  | P0102 | 2 | 93.5 | 1.0 | 48.4 | 0.9 |
|  | P0103 | 3 | 93.9 | 1.0 | 50.8 | 1.0 |
|  | P0104 | 4 | 87.7 | 1.0 | 49.1 | 0.9 |
| 2 | P0201 | 5 | 98.3 | 1.1 | 48.6 | 0.9 |
|  | P0202 | 6 | 93.5 | 1.0 | 48.4 | 0.9 |
|  | P0204 | 7 | 93.9 | 1.0 | 50.8 | 1.0 |
|  | P0205 | 8 | 87.7 | 1.0 | 49.1 | 0.9 |
| 3 | P0302 | 9 | 81.6 | 0.9 | 48.8 | 0.9 |
|  | P0303 | 10 | 92.3 | 1.0 | 46.5 | 0.9 |
|  | P0304 | 11 | 76.6 | 0.9 | 47.8 | 0.9 |
|  | P0305 | 12 | 79.7 | 0.9 | 47.3 | 0.9 |
| 4 | P0401 | 13 | 108.1 | 1.2 | 48.3 | 0.9 |
|  | P0402 | 14 | 83.3 | 0.9 | 48.5 | 0.9 |
|  | P0403 | 15 | 81.0 | 0.9 | 47.9 | 0.9 |
|  | P0404 | 16 | 80.1 | 0.9 | 54.4 | 1.0 |
| 5 | P0503 | 17 | 83.0 | 0.9 | 47.3 | 0.9 |
|  | P0502 | 18 | 87.1 | 1.0 | 48.7 | 0.9 |
| 6 | P0601 | 19 | 86.4 | 1.0 | 47.5 | 0.9 |
|  | P0602 | 20 | 85.1 | 0.9 | 46.8 | 0.9 |
|  | P0603 | 21 | 83.5 | 0.9 | 48.3 | 0.9 |
|  | P0604 | 22 | 81.5 | 0.9 | 47.4 | 0.9 |
| 7 | P0701 | 23 | 80.8 | 0.9 | 47.4 | 0.9 |
|  | P0702 | 24 | 86.9 | 1.0 | 49.9 | 0.9 |
|  | P0703 | 25 | 82.1 | 0.9 | 48.2 | 0.9 |
|  | P0704 | 26 | 83.9 | 0.9 | 47.9 | 0.9 |
| 8 | P0801 | 27 | 87.8 | 1.0 | 48.3 | 0.9 |
|  | P0803 | 28 | 87.7 | 1.0 | 48.6 | 0.9 |

TABLE 57

*Epidermophyton floccosum*

| Group | Probe Name | SEQ ID No: | 1st Intensity | 1st S/N | 2nd Intensity | 2nd S/N |
|---|---|---|---|---|---|---|
| 9 | P0901 | 29 | 86.9 | 1.0 | 50.3 | 0.9 |
|   | P0902 | 30 | 80.4 | 0.9 | 48.9 | 0.9 |
|   | P0903 | 31 | 75.9 | 0.8 | 47.6 | 0.9 |
| 10 | P1102 | 32 | 82.2 | 0.9 | 53.1 | 1.0 |
|   | P1103 | 33 | 83.0 | 0.9 | 49.0 | 0.9 |
|   | P1104 | 34 | 80.4 | 0.9 | 48.8 | 0.9 |
| 11 | P2701 | 35 | 81.3 | 0.9 | 47.7 | 0.9 |
|   | P2702 | 36 | 78.6 | 0.9 | 47.6 | 0.9 |
| 12 | P2801 | 37 | 80.8 | 0.9 | 48.4 | 0.9 |
|   | P2802 | 38 | 79.9 | 0.9 | 48.0 | 0.9 |
| 13 | P3301 | 39 | 121.5 | 1.4 | 53.3 | 1.0 |
|   | P3302 | 40 | 77.8 | 0.9 | 48.1 | 0.9 |
| 14 | P2901 | 41 | 83.5 | 0.9 | 50.3 | 1.0 |
|   | P2902 | 42 | 80.3 | 0.9 | 48.7 | 0.9 |
|   | P2903 | 43 | 78.2 | 0.9 | 48.4 | 0.9 |
| 15 | P3001 | 44 | 80.8 | 0.9 | 48.1 | 0.9 |
|   | P3002 | 45 | 78.4 | 0.9 | 48.7 | 0.9 |
|   | P3003 | 46 | 75.4 | 0.8 | 49.4 | 0.9 |
| 16 | P1901 | 47 | 1859.9 | 20.7 | 386.0 | 7.3 |
|   | P1902 | 48 | 6406.3 | 71.4 | 3197.0 | 60.4 |
|   | P1903 | 49 | 3279.5 | 36.6 | 1198.2 | 22.6 |
|   | P1904 | 50 | 1823.1 | 20.3 | 310.2 | 5.9 |
| 17 | P2001 | 51 | 84.1 | 0.9 | 52.2 | 1.0 |
|   | P2002 | 52 | 84.2 | 0.9 | 47.1 | 0.9 |
| 18 | P2105 | 53 | 86.2 | 1.0 | 48.4 | 0.9 |
|   | P2102 | 54 | 80.2 | 0.9 | 50.1 | 0.9 |
|   | P2103 | 55 | 86.1 | 1.0 | 48.8 | 0.9 |

TABLE 58

*Epidermophyton floccosum*

| Group | Probe Name | SEQ ID No: | 1st Intensity | 1st S/N | 2nd Intensity | 2nd S/N |
|---|---|---|---|---|---|---|
| 19 | P2205 | 56 | 88.6 | 1.0 | 70.2 | 1.3 |
|   | P2202 | 57 | 83.4 | 0.9 | 49.5 | 0.9 |
|   | P2203 | 58 | 121.5 | 1.4 | 57.8 | 1.1 |
|   | P2204 | 69 | 79.4 | 0.9 | 50.2 | 0.9 |
| 20 | P2302 | 60 | 84.8 | 0.9 | 48.6 | 0.9 |
|   | P2306 | 61 | 76.9 | 0.9 | 49.5 | 0.9 |
|   | P2305 | 62 | 76.8 | 0.9 | 50.6 | 1.0 |
| 21 | P2405 | 63 | 81.9 | 0.9 | 50.5 | 1.0 |
|   | P2402 | 64 | 121.0 | 1.3 | 47.4 | 0.9 |
|   | P2403 | 65 | 76.6 | 0.9 | 52.4 | 1.0 |
| 22 | P2501 | 66 | 80.1 | 0.9 | 48.3 | 0.9 |
|   | P2502 | 67 | 1170.6 | 13.0 | 227.5 | 4.3 |
| 23 | P2604 | 68 | 85.3 | 1.0 | 50.6 | 1.0 |
|   | P2601 | 69 | 80.4 | 0.9 | 47.9 | 0.9 |
| 24 | P3101 | 70 | 88.9 | 1.0 | 48.3 | 0.9 |
|   | P3102 | 71 | 75.7 | 0.8 | 48.2 | 0.9 |
| 25 | P3201 | 72 | 90.7 | 1.0 | 48.7 | 0.9 |
|   | P3202 | 73 | 83.9 | 0.9 | 48.8 | 0.9 |
| 26 | P3401 | 74 | 91.7 | 1.0 | 55.6 | 1.1 |
|   | P3402 | 75 | 90.7 | 1.0 | 55.1 | 1.0 |
| 27 | Ptricho1 | 76 | 9503.6 | 105.9 | 4211.0 | 79.5 |
| 28 | Pfila1 | 77 | 19084.0 | 212.7 | 12919.4 | 243.9 |
| 29 | Pfungi1 | 78 | 11251.2 | 125.4 | 8036.9 | 151.7 |
|   | Pfungi2 | 79 | 9250.2 | 103.1 | 5466.3 | 103.2 |
|   | Pfungi3 | 80 | 10051.0 | 112.0 | 7476.1 | 141.1 |

TABLE 59

*Arthroderma otae*

| Group | Probe Name | SEQ ID No: | 1st Intensity | 1st S/N | 2nd Intensity | 2nd S/N |
|---|---|---|---|---|---|---|
| 1 | P0101 | 1 | 86.8 | 0.9 | 45.8 | 0.9 |
|   | P0102 | 2 | 79.9 | 0.8 | 46.9 | 0.9 |
|   | P0103 | 3 | 89.5 | 0.9 | 49.5 | 1.0 |
|   | P0104 | 4 | 81.0 | 0.9 | 46.5 | 0.9 |
| 2 | P0201 | 5 | 86.8 | 0.9 | 45.8 | 0.9 |
|   | P0202 | 6 | 79.9 | 0.8 | 46.9 | 0.9 |
|   | P0204 | 7 | 89.5 | 0.9 | 49.5 | 1.0 |
|   | P0205 | 8 | 81.0 | 0.9 | 46.5 | 0.9 |
| 3 | P0302 | 9 | 80.4 | 0.9 | 45.4 | 0.9 |
|   | P0303 | 10 | 72.2 | 0.8 | 46.5 | 0.9 |
|   | P0304 | 11 | 69.4 | 0.7 | 46.3 | 0.9 |
|   | P0305 | 12 | 73.9 | 0.8 | 46.6 | 0.9 |
| 4 | P0401 | 13 | 85.0 | 0.9 | 46.7 | 0.9 |
|   | P0402 | 14 | 72.3 | 0.8 | 46.3 | 0.9 |
|   | P0403 | 15 | 72.7 | 0.8 | 47.5 | 1.0 |
|   | P0404 | 16 | 75.5 | 0.8 | 50.7 | 1.0 |
| 5 | P0503 | 17 | 77.6 | 0.8 | 45.9 | 0.9 |
|   | P0502 | 18 | 75.2 | 0.8 | 45.8 | 0.9 |
| 6 | P0601 | 19 | 78.3 | 0.8 | 46.1 | 0.9 |
|   | P0602 | 20 | 75.6 | 0.8 | 45.3 | 0.9 |
|   | P0603 | 21 | 76.1 | 0.8 | 46.8 | 0.9 |
|   | P0604 | 22 | 75.2 | 0.8 | 48.9 | 1.0 |
| 7 | P0701 | 23 | 76.1 | 0.8 | 45.5 | 0.9 |
|   | P0702 | 24 | 130.5 | 1.4 | 48.5 | 1.0 |
|   | P0703 | 25 | 75.4 | 0.8 | 45.9 | 0.9 |
|   | P0704 | 26 | 73.4 | 0.8 | 47.4 | 1.0 |
| 8 | P0801 | 27 | 77.8 | 0.8 | 47.7 | 1.0 |
|   | P0803 | 28 | 80.6 | 0.9 | 46.3 | 0.9 |

TABLE 60

*Arthroderma otae*

| Group | Probe Name | SEQ ID No: | 1st Intensity | 1st S/N | 2nd Intensity | 2nd S/N |
|---|---|---|---|---|---|---|
| 9 | P0901 | 29 | 83.0 | 0.9 | 48.1 | 1.0 |
|   | P0902 | 30 | 72.9 | 0.8 | 47.5 | 1.0 |
|   | P0903 | 31 | 69.2 | 0.7 | 46.2 | 0.9 |
| 10 | P1102 | 32 | 78.3 | 0.8 | 52.7 | 1.1 |
|   | P1103 | 33 | 82.4 | 0.9 | 46.0 | 0.9 |
|   | P1104 | 34 | 74.4 | 0.8 | 46.8 | 0.9 |
| 11 | P2701 | 35 | 71.4 | 0.8 | 47.4 | 1.0 |
|   | P2702 | 36 | 70.8 | 0.8 | 46.1 | 0.9 |
| 12 | P2801 | 37 | 76.3 | 0.8 | 47.0 | 0.9 |
|   | P2802 | 38 | 73.4 | 0.8 | 48.3 | 1.0 |
| 13 | P3301 | 39 | 100.1 | 1.1 | 49.8 | 1.0 |
|   | P3302 | 40 | 76.1 | 0.8 | 46.2 | 0.9 |
| 14 | P2901 | 41 | 96.3 | 1.0 | 47.2 | 1.0 |
|   | P2902 | 42 | 77.3 | 0.8 | 47.6 | 1.0 |
|   | P2903 | 43 | 73.5 | 0.8 | 46.6 | 0.9 |
| 15 | P3001 | 44 | 75.8 | 0.8 | 46.6 | 0.9 |
|   | P3002 | 45 | 77.3 | 0.8 | 46.8 | 0.9 |
|   | P3003 | 46 | 79.4 | 0.8 | 47.9 | 1.0 |
| 16 | P1901 | 47 | 87.5 | 0.9 | 46.8 | 0.9 |
|   | P1902 | 48 | 83.8 | 0.9 | 48.0 | 1.0 |
|   | P1903 | 49 | 81.3 | 0.9 | 46.4 | 0.9 |
|   | P1904 | 50 | 80.7 | 0.9 | 48.7 | 1.0 |
| 17 | P2001 | 51 | 3221.5 | 34.2 | 700.8 | 14.2 |
|   | P2002 | 52 | 6052.5 | 64.3 | 2092.1 | 42.3 |
| 18 | P2105 | 53 | 82.0 | 0.9 | 49.6 | 1.0 |
|   | P2102 | 54 | 78.9 | 0.8 | 46.0 | 0.9 |
|   | P2103 | 55 | 81.6 | 0.9 | 46.4 | 0.9 |

TABLE 61

*Arthroderma otae*

| Group | Probe Name | SEQ ID No: | 1st Intensity | 1st S/N | 2nd Intensity | 2nd S/N |
|---|---|---|---|---|---|---|
| 19 | P2205 | 56 | 82.3 | 0.9 | 67.9 | 1.4 |
|  | P2202 | 57 | 79.7 | 0.8 | 48.3 | 1.0 |
|  | P2203 | 58 | 78.3 | 0.8 | 53.5 | 1.1 |
|  | P2204 | 59 | 76.0 | 0.8 | 47.9 | 1.0 |
| 20 | P2302 | 60 | 81.4 | 0.9 | 47.0 | 0.9 |
|  | P2306 | 61 | 78.5 | 0.8 | 48.0 | 1.0 |
|  | P2305 | 62 | 75.3 | 0.8 | 49.2 | 1.0 |
| 21 | P2405 | 63 | 79.4 | 0.8 | 47.0 | 0.9 |
|  | P2402 | 64 | 80.6 | 0.9 | 45.8 | 0.9 |
|  | P2403 | 65 | 76.8 | 0.8 | 48.3 | 1.0 |
| 22 | P2501 | 66 | 77.9 | 0.8 | 48.3 | 1.0 |
|  | P2502 | 67 | 1635.1 | 17.4 | 367.7 | 7.4 |
| 23 | P2604 | 68 | 80.9 | 0.9 | 47.9 | 1.0 |
|  | P2601 | 69 | 78.3 | 0.8 | 47.9 | 1.0 |
| 24 | P3101 | 70 | 86.6 | 0.9 | 48.7 | 1.0 |
|  | P3102 | 71 | 78.0 | 0.8 | 47.3 | 1.0 |
| 25 | P3201 | 72 | 82.8 | 0.9 | 46.5 | 0.9 |
|  | P3202 | 73 | 78.9 | 0.8 | 46.1 | 0.9 |
| 26 | P3401 | 74 | 79.4 | 0.8 | 53.1 | 1.1 |
|  | P3402 | 75 | 78.9 | 0.8 | 53.1 | 1.1 |
| 27 | Ptricho1 | 76 | 9920.5 | 105.3 | 2931.1 | 59.2 |
| 28 | Pfila1 | 77 | 24581.8 | 261.0 | 12898.8 | 260.5 |
| 29 | Pfungi1 | 78 | 13637.9 | 144.8 | 4495.7 | 90.8 |
|  | Pfungi2 | 79 | 9514.5 | 101.0 | 2872.3 | 58.0 |
|  | Pfungi3 | 80 | 11197.0 | 118.9 | 5684.7 | 114.8 |

TABLE 62

*Arthroderma gypseum*

| Group | Probe Name | SEQ ID No: | 1st Intensity | 1st S/N | 2nd Intensity | 2nd S/N |
|---|---|---|---|---|---|---|
| 1 | P0101 | 1 | 98.3 | 1.1 | 50.1 | 0.9 |
|  | P0102 | 2 | 117.2 | 1.3 | 49.0 | 0.9 |
|  | P0103 | 3 | 95.5 | 1.1 | 51.1 | 1.0 |
|  | P0104 | 4 | 88.3 | 1.0 | 50.6 | 1.0 |
| 2 | P0201 | 5 | 98.3 | 1.1 | 50.1 | 0.9 |
|  | P0202 | 6 | 117.2 | 1.3 | 49.0 | 0.9 |
|  | P0204 | 7 | 95.5 | 1.1 | 51.1 | 1.0 |
|  | P0205 | 8 | 88.3 | 1.0 | 50.6 | 1.0 |
| 3 | P0302 | 9 | 75.9 | 0.8 | 49.2 | 0.9 |
|  | P0303 | 10 | 85.5 | 0.9 | 48.8 | 0.9 |
|  | P0304 | 11 | 80.7 | 0.9 | 48.5 | 0.9 |
|  | P0305 | 12 | 76.7 | 0.8 | 48.4 | 0.9 |
| 4 | P0401 | 13 | 83.3 | 0.9 | 49.4 | 0.9 |
|  | P0402 | 14 | 78.9 | 0.9 | 49.5 | 0.9 |
|  | P0403 | 15 | 75.9 | 0.8 | 49.3 | 0.9 |
|  | P0404 | 16 | 78.3 | 0.9 | 53.1 | 1.0 |
| 5 | P0503 | 17 | 76.1 | 0.8 | 49.0 | 0.9 |
|  | P0502 | 18 | 82.1 | 0.9 | 48.1 | 0.9 |
| 6 | P0601 | 19 | 76.7 | 0.8 | 48.4 | 0.9 |
|  | P0602 | 20 | 79.4 | 0.9 | 47.7 | 0.9 |
|  | P0603 | 21 | 79.5 | 0.9 | 49.2 | 0.9 |
|  | P0604 | 22 | 78.3 | 0.9 | 49.6 | 0.9 |
| 7 | P0701 | 23 | 83.2 | 0.9 | 49.2 | 0.9 |
|  | P0702 | 24 | 132.5 | 1.5 | 51.9 | 1.0 |
|  | P0703 | 25 | 80.3 | 0.9 | 49.1 | 0.9 |
|  | P0704 | 26 | 78.3 | 0.9 | 49.9 | 0.9 |
| 8 | P0801 | 27 | 81.3 | 0.9 | 47.9 | 0.9 |
|  | P0803 | 28 | 78.5 | 0.9 | 48.2 | 0.9 |

TABLE 63

*Arthroderma gypseum*

| Group | Probe Name | SEQ ID No: | 1st Intensity | 1st S/N | 2nd Intensity | 2nd S/N |
|---|---|---|---|---|---|---|
| 9 | P0901 | 29 | 86.2 | 1.0 | 50.2 | 0.9 |
|  | P0902 | 30 | 77.3 | 0.9 | 49.1 | 0.9 |
|  | P0903 | 31 | 79.8 | 0.9 | 50.1 | 0.9 |
| 10 | P1102 | 32 | 81.3 | 0.9 | 54.9 | 1.0 |
|  | P1103 | 33 | 78.1 | 0.9 | 48.8 | 0.9 |
|  | P1104 | 34 | 73.4 | 0.8 | 49.0 | 0.9 |
| 11 | P2701 | 35 | 82.2 | 0.9 | 49.3 | 0.9 |
|  | P2702 | 36 | 74.3 | 0.8 | 49.7 | 0.9 |
| 12 | P2801 | 37 | 78.4 | 0.9 | 51.6 | 1.0 |
|  | P2802 | 38 | 75.4 | 0.8 | 50.8 | 1.0 |
| 13 | P3301 | 39 | 124.6 | 1.4 | 55.1 | 1.0 |
|  | P3302 | 40 | 74.3 | 0.8 | 49.9 | 0.9 |
| 14 | P2901 | 41 | 76.9 | 0.9 | 50.0 | 0.9 |
|  | P2902 | 42 | 76.2 | 0.8 | 49.7 | 0.9 |
|  | P2903 | 43 | 73.8 | 0.8 | 51.9 | 1.0 |
| 15 | P3001 | 44 | 78.3 | 0.9 | 48.8 | 0.9 |
|  | P3002 | 45 | 79.3 | 0.9 | 50.1 | 0.9 |
|  | P3003 | 46 | 76.2 | 0.8 | 49.4 | 0.9 |
| 16 | P1901 | 47 | 88.7 | 1.0 | 49.5 | 0.9 |
|  | P1902 | 48 | 83.4 | 0.9 | 49.8 | 0.9 |
|  | P1903 | 49 | 84.0 | 0.9 | 48.8 | 0.9 |
|  | P1904 | 50 | 75.9 | 0.8 | 50.4 | 1.0 |
| 17 | P2001 | 51 | 81.9 | 0.9 | 54.0 | 1.0 |
|  | P2002 | 52 | 87.8 | 1.0 | 48.5 | 0.9 |
| 18 | P2105 | 53 | 4786.9 | 53.0 | 633.3 | 12.0 |
|  | P2102 | 54 | 17762.9 | 196.6 | 5430.4 | 102.5 |
|  | P2103 | 55 | 12491.6 | 138.2 | 1721.6 | 32.5 |

TABLE 64

*Arthroderma gypseum*

| Group | Probe Name | SEQ ID No: | 1st Intensity | 1st S/N | 2nd Intensity | 2nd S/N |
|---|---|---|---|---|---|---|
| 19 | P2205 | 56 | 91.6 | 1.0 | 69.8 | 1.3 |
|  | P2202 | 57 | 148.3 | 1.6 | 55.1 | 1.0 |
|  | P2203 | 58 | 239.8 | 2.7 | 71.4 | 1.3 |
|  | P2204 | 59 | 114.0 | 1.3 | 50.7 | 1.0 |
| 20 | P2302 | 60 | 76.9 | 0.9 | 49.1 | 0.9 |
|  | P2306 | 61 | 82.9 | 0.9 | 49.2 | 0.9 |
|  | P2305 | 62 | 78.0 | 0.9 | 50.5 | 1.0 |
| 21 | P2405 | 63 | 79.3 | 0.9 | 49.9 | 0.9 |
|  | P2402 | 64 | 149.7 | 1.7 | 50.4 | 1.0 |
|  | P2403 | 65 | 80.6 | 0.9 | 55.8 | 1.1 |
| 22 | P2501 | 66 | 95.0 | 1.1 | 51.9 | 1.0 |
|  | P2502 | 67 | 3005.0 | 33.3 | 368.1 | 6.9 |
| 23 | P2604 | 68 | 83.9 | 0.9 | 50.2 | 0.9 |
|  | P2601 | 69 | 87.3 | 1.0 | 48.3 | 0.9 |
| 24 | P3101 | 70 | 85.3 | 0.9 | 49.1 | 0.9 |
|  | P3102 | 71 | 78.9 | 0.9 | 49.5 | 0.9 |
| 25 | P3201 | 72 | 99.6 | 1.1 | 50.9 | 1.0 |
|  | P3202 | 73 | 94.1 | 1.0 | 50.9 | 1.0 |
| 26 | P3401 | 74 | 80.5 | 0.9 | 49.7 | 0.9 |
|  | P3402 | 75 | 81.9 | 0.9 | 49.5 | 0.9 |
| 27 | Ptricho1 | 76 | 16606.9 | 183.8 | 4346.9 | 82.0 |
| 28 | Pfila1 | 77 | 30165.7 | 333.8 | 10619.3 | 200.4 |
| 29 | Pfungi1 | 78 | 16791.0 | 185.8 | 4954.9 | 93.5 |
|  | Pfungi2 | 79 | 10322.5 | 114.2 | 3738.4 | 70.6 |
|  | Pfungi3 | 80 | 12989.8 | 143.8 | 4920.4 | 92.9 |

TABLE 65

*Arthroderma benhamiae*

| Group | Probe Name | SEQ ID No: | 1st Intensity | 1st S/N | 2nd Intensity | 2nd S/N |
|---|---|---|---|---|---|---|
| 1 | P0101 | 1 | 93.9 | 0.9 | 56.1 | 0.9 |
|  | P0102 | 2 | 94.7 | 0.9 | 55.8 | 0.9 |
|  | P0103 | 3 | 97.8 | 0.9 | 64.3 | 1.0 |
|  | P0104 | 4 | 102.5 | 1.0 | 55.9 | 0.9 |
| 2 | P0201 | 5 | 93.9 | 0.9 | 56.1 | 0.9 |
|  | P0202 | 6 | 94.7 | 0.9 | 55.8 | 0.9 |
|  | P0204 | 7 | 97.8 | 0.9 | 64.3 | 1.0 |
|  | P0205 | 8 | 102.5 | 1.0 | 55.9 | 0.9 |
| 3 | P0302 | 9 | 87.0 | 0.8 | 56.3 | 0.9 |
|  | P0303 | 10 | 84.6 | 0.8 | 57.0 | 0.9 |
|  | P0304 | 11 | 90.5 | 0.8 | 277.8 | 4.3 |
|  | P0305 | 12 | 84.7 | 0.8 | 58.1 | 0.9 |
| 4 | P0401 | 13 | 87.5 | 0.8 | 54.8 | 0.8 |
|  | P0402 | 14 | 90.0 | 0.8 | 56.5 | 0.9 |
|  | P0403 | 15 | 85.2 | 0.8 | 56.3 | 0.9 |
|  | P0404 | 16 | 89.1 | 0.8 | 88.2 | 1.4 |
| 5 | P0503 | 17 | 79.7 | 0.7 | 54.5 | 0.9 |
|  | P0502 | 18 | 85.7 | 0.8 | 57.3 | 0.8 |
| 6 | P0601 | 19 | 87.3 | 0.8 | 58.0 | 0.9 |
|  | P0602 | 20 | 86.8 | 0.8 | 57.5 | 0.9 |
|  | P0603 | 21 | 86.8 | 0.8 | 56.1 | 0.9 |
|  | P0604 | 22 | 95.3 | 0.9 | 87.3 | 1.3 |
| 7 | P0701 | 23 | 82.6 | 0.8 | 57.0 | 0.9 |
|  | P0702 | 24 | 183.8 | 1.7 | 114.1 | 1.8 |
|  | P0703 | 25 | 84.7 | 0.8 | 56.1 | 0.9 |
|  | P0704 | 26 | 88.2 | 0.8 | 55.2 | 0.9 |
| 8 | P0801 | 27 | 85.0 | 0.8 | 56.2 | 0.9 |
|  | P0803 | 28 | 96.3 | 0.9 | 55.4 | 0.9 |

TABLE 66

*Arthroderma benhamiae*

| Group | Probe Name | SEQ ID No: | 1st Intensity | 1st S/N | 2nd Intensity | 2nd S/N |
|---|---|---|---|---|---|---|
| 9 | P0901 | 29 | 90.9 | 0.8 | 58.6 | 0.9 |
|  | P0902 | 30 | 81.9 | 0.8 | 58.3 | 0.9 |
|  | P0903 | 31 | 84.9 | 0.8 | 56.1 | 0.9 |
| 10 | P1102 | 32 | 77.0 | 0.7 | 70.3 | 1.1 |
|  | P1103 | 33 | 89.3 | 0.8 | 56.3 | 0.9 |
|  | P1104 | 34 | 82.6 | 0.8 | 1272.0 | 19.6 |
| 11 | P2701 | 35 | 88.1 | 0.8 | 56.6 | 0.9 |
|  | P2702 | 36 | 82.9 | 0.8 | 56.9 | 0.9 |
| 12 | P2801 | 37 | 91.3 | 0.8 | 55.8 | 0.9 |
|  | P2802 | 38 | 87.8 | 0.8 | 85.2 | 1.3 |
| 13 | P3301 | 39 | 162.4 | 1.5 | 78.9 | 1.2 |
|  | P3302 | 40 | 83.2 | 0.8 | 55.9 | 0.9 |
| 14 | P2901 | 41 | 91.3 | 0.8 | 56.4 | 0.9 |
|  | P2902 | 42 | 89.8 | 0.8 | 58.2 | 0.9 |
|  | P2903 | 43 | 79.3 | 0.7 | 58.3 | 0.9 |
| 15 | P3001 | 44 | 85.0 | 0.8 | 56.5 | 0.9 |
|  | P3002 | 45 | 88.1 | 0.8 | 56.9 | 0.9 |
|  | P3003 | 46 | 84.3 | 0.8 | 57.0 | 0.9 |
| 16 | P1901 | 47 | 90.5 | 0.8 | 59.6 | 0.9 |
|  | P1902 | 48 | 91.7 | 0.9 | 57.0 | 0.9 |
|  | P1903 | 49 | 139.8 | 1.3 | 136.1 | 2.1 |
|  | P1904 | 50 | 85.3 | 0.8 | 59.7 | 0.9 |
| 17 | P2001 | 51 | 92.3 | 0.9 | 66.9 | 1.0 |
|  | P2002 | 52 | 80.9 | 0.8 | 55.9 | 0.9 |
| 18 | P2105 | 53 | 86.8 | 0.8 | 61.0 | 0.9 |
|  | P2102 | 54 | 108.3 | 1.0 | 66.7 | 1.0 |
|  | P2103 | 55 | 85.2 | 0.8 | 57.3 | 0.9 |

TABLE 67

*Arthroderma benhamiae*

| Group | Probe Name | SEQ ID No: | 1st Intensity | 1st S/N | 2nd Intensity | 2nd S/N |
|---|---|---|---|---|---|---|
| 19 | P2205 | 56 | 3228.8 | 30.0 | 702.5 | 10.8 |
|  | P2202 | 57 | 24877.1 | 231.1 | 12014.8 | 185.2 |
|  | P2203 | 58 | 30529.9 | 283.6 | 12378.8 | 190.9 |
|  | P2204 | 59 | 27884.7 | 259.0 | 6543.0 | 100.9 |
| 20 | P2302 | 60 | 81.3 | 0.8 | 56.2 | 0.9 |
|  | P2306 | 61 | 93.1 | 0.9 | 88.7 | 1.4 |
|  | P2305 | 62 | 92.2 | 0.9 | 60.8 | 0.9 |
| 21 | P2405 | 63 | 83.8 | 0.8 | 65.8 | 1.0 |
|  | P2402 | 64 | 280.6 | 2.6 | 56.8 | 0.9 |
|  | P2403 | 65 | 87.1 | 0.8 | 448.8 | 6.9 |
| 22 | P2501 | 66 | 5994.4 | 55.7 | 1687.1 | 26.0 |
|  | P2502 | 67 | 2633.2 | 24.5 | 1885.1 | 29.1 |
| 23 | P2604 | 68 | 92.0 | 0.9 | 58.2 | 0.9 |
|  | P2601 | 69 | 100.0 | 0.9 | 57.1 | 0.9 |
| 24 | P3101 | 70 | 86.7 | 0.8 | 59.8 | 0.9 |
|  | P3102 | 71 | 89.2 | 0.8 | 64.9 | 1.0 |
| 25 | P3201 | 72 | 92.4 | 0.9 | 70.2 | 1.1 |
|  | P3202 | 73 | 92.2 | 0.9 | 57.2 | 0.9 |
| 26 | P3401 | 74 | 89.6 | 0.8 | 66.0 | 1.0 |
|  | P3402 | 75 | 91.6 | 0.9 | 65.7 | 1.0 |
| 27 | Ptricho1 | 76 | 20130.2 | 187.0 | 9364.5 | 144.4 |
| 28 | Pfila1 | 77 | 55960.5 | 519.8 | 23195.9 | 357.6 |
| 29 | Pfungi1 | 78 | 25557.1 | 237.4 | 10735.7 | 165.5 |
|  | Pfungi2 | 79 | 21799.3 | 202.5 | 7868.9 | 121.3 |
|  | Pfungi3 | 80 | 28187.0 | 261.8 | 12128.3 | 187.0 |

TABLE 68

*Trichophyton rubrum*

| Group | Probe Name | SEQ ID No: | 1st Intensity | 1st S/N | 2nd Intensity | 2nd S/N |
|---|---|---|---|---|---|---|
| 1 | P0101 | 1 | 89.6 | 1.0 | 46.3 | 0.9 |
|  | P0102 | 2 | 87.4 | 0.9 | 47.0 | 1.0 |
|  | P0103 | 3 | 89.8 | 1.0 | 46.9 | 0.9 |
|  | P0104 | 4 | 86.2 | 0.9 | 46.7 | 0.9 |
| 2 | P0201 | 5 | 89.6 | 1.0 | 46.3 | 0.9 |
|  | P0202 | 6 | 87.4 | 0.9 | 47.0 | 1.0 |
|  | P0204 | 7 | 89.8 | 1.0 | 46.9 | 0.9 |
|  | P0205 | 8 | 86.2 | 0.9 | 46.7 | 0.9 |
| 3 | P0302 | 9 | 81.0 | 0.9 | 46.8 | 0.9 |
|  | P0303 | 10 | 85.7 | 0.9 | 45.7 | 0.9 |
|  | P0304 | 11 | 78.4 | 0.8 | 47.1 | 1.0 |
|  | P0305 | 12 | 80.9 | 0.9 | 44.8 | 0.9 |
| 4 | P0401 | 13 | 86.7 | 0.9 | 47.5 | 1.0 |
|  | P0402 | 14 | 73.1 | 0.8 | 47.3 | 1.0 |
|  | P0403 | 15 | 78.9 | 0.8 | 46.8 | 0.9 |
|  | P0404 | 16 | 80.9 | 0.9 | 52.0 | 1.1 |
| 5 | P0503 | 17 | 79.7 | 0.9 | 46.8 | 1.0 |
|  | P0502 | 18 | 83.9 | 0.9 | 48.2 | 0.9 |
| 6 | P0601 | 19 | 81.6 | 0.9 | 44.9 | 0.9 |
|  | P0602 | 20 | 76.9 | 0.8 | 47.2 | 1.0 |
|  | P0603 | 21 | 79.4 | 0.9 | 46.3 | 0.9 |
|  | P0604 | 22 | 77.2 | 0.8 | 46.3 | 0.9 |
| 7 | P0701 | 23 | 81.7 | 0.9 | 47.3 | 1.0 |
|  | P0702 | 24 | 121.8 | 1.3 | 49.0 | 1.0 |
|  | P0703 | 25 | 81.7 | 0.9 | 46.2 | 0.9 |
|  | P0704 | 26 | 84.8 | 0.9 | 46.4 | 0.9 |
| 8 | P0801 | 27 | 87.4 | 0.9 | 46.9 | 0.9 |
|  | P0803 | 28 | 80.5 | 0.9 | 45.3 | 0.9 |

TABLE 69

*Trichophyton rubrum*

| Group | Probe Name | SEQ ID No: | 1st Intensity | S/N | 2nd Intensity | S/N |
|---|---|---|---|---|---|---|
| 9 | P0901 | 29 | 89.2 | 1.0 | 47.5 | 1.0 |
|   | P0902 | 30 | 81.6 | 0.9 | 47.5 | 1.0 |
|   | P0903 | 31 | 81.0 | 0.9 | 47.9 | 1.0 |
| 10 | P1102 | 32 | 78.4 | 0.8 | 52.1 | 1.1 |
|   | P1103 | 33 | 74.7 | 0.8 | 47.2 | 1.0 |
|   | P1104 | 34 | 88.9 | 1.0 | 46.4 | 0.9 |
| 11 | P2701 | 35 | 78.5 | 0.8 | 48.1 | 1.0 |
|   | P2702 | 36 | 81.4 | 0.9 | 47.0 | 1.0 |
| 12 | P2801 | 37 | 80.0 | 0.9 | 46.9 | 0.9 |
|   | P2802 | 38 | 88.1 | 0.9 | 48.8 | 1.0 |
| 13 | P3301 | 39 | 122.1 | 1.3 | 48.9 | 1.0 |
|   | P3302 | 40 | 82.0 | 0.9 | 46.8 | 0.9 |
| 14 | P2901 | 41 | 87.8 | 0.9 | 46.7 | 0.9 |
|   | P2902 | 42 | 83.0 | 0.9 | 46.4 | 0.9 |
|   | P2903 | 43 | 83.6 | 0.9 | 45.5 | 0.9 |
| 15 | P3001 | 44 | 84.5 | 0.9 | 46.4 | 0.9 |
|   | P3002 | 45 | 86.7 | 0.9 | 47.3 | 1.0 |
|   | P3003 | 46 | 82.5 | 0.9 | 45.9 | 0.9 |
| 16 | P1901 | 47 | 81.3 | 0.9 | 47.0 | 1.0 |
|   | P1902 | 48 | 81.2 | 0.9 | 47.1 | 1.0 |
|   | P1903 | 49 | 80.2 | 0.9 | 47.6 | 1.0 |
|   | P1904 | 50 | 84.6 | 0.9 | 47.6 | 1.0 |
| 17 | P2001 | 51 | 78.6 | 0.8 | 50.7 | 1.0 |
|   | P2002 | 52 | 79.2 | 0.8 | 47.0 | 1.0 |
| 18 | P2105 | 53 | 82.2 | 0.9 | 49.9 | 1.0 |
|   | P2102 | 54 | 86.2 | 0.9 | 47.8 | 1.0 |
|   | P2103 | 55 | 81.4 | 0.9 | 45.6 | 0.9 |

TABLE 70

*Trichophyton rubrum*

| Group | Probe Name | SEQ ID No: | 1st Intensity | S/N | 2nd Intensity | S/N |
|---|---|---|---|---|---|---|
| 19 | P2205 | 56 | 88.4 | 0.9 | 62.2 | 1.3 |
|   | P2202 | 57 | 86.8 | 0.9 | 47.9 | 1.0 |
|   | P2203 | 58 | 162.5 | 1.7 | 58.9 | 1.2 |
|   | P2204 | 59 | 82.3 | 0.9 | 47.2 | 1.0 |
| 20 | P2302 | 60 | 24613.9 | 264.0 | 2813.8 | 56.9 |
|   | P2306 | 61 | 652.6 | 7.0 | 2711.6 | 54.8 |
|   | P2305 | 62 | 12876.8 | 138.1 | 142.2 | 2.9 |
| 21 | P2405 | 63 | 84.0 | 0.9 | 54.5 | 1.1 |
|   | P2402 | 64 | 1489.8 | 16.0 | 46.8 | 0.9 |
|   | P2403 | 65 | 136.3 | 1.5 | 217.5 | 4.4 |
| 22 | P2501 | 66 | 93.8 | 1.0 | 47.5 | 1.0 |
|   | P2502 | 67 | 4324.3 | 46.4 | 477.7 | 9.7 |
| 23 | P2604 | 68 | 346.0 | 3.7 | 68.1 | 1.4 |
|   | P2601 | 69 | 514.3 | 5.5 | 52.6 | 1.1 |
| 24 | P3101 | 70 | 95.1 | 1.0 | 46.0 | 0.9 |
|   | P3102 | 71 | 89.7 | 1.0 | 46.7 | 0.9 |
| 25 | P3201 | 72 | 82.1 | 0.9 | 47.8 | 1.0 |
|   | P3202 | 73 | 81.3 | 0.9 | 47.0 | 1.0 |
| 26 | P3401 | 74 | 153.2 | 1.6 | 56.8 | 1.1 |
|   | P3402 | 75 | 186.8 | 2.0 | 53.7 | 1.1 |
| 27 | Ptricho1 | 76 | 12308.3 | 132.0 | 3885.8 | 78.5 |
| 28 | Pfila1 | 77 | 49150.9 | 527.1 | 14168.7 | 286.3 |
| 29 | Pfungi1 | 78 | 20111.7 | 215.7 | 4326.5 | 87.4 |
|   | Pfungi2 | 79 | 18883.5 | 202.5 | 3665.9 | 74.1 |
|   | Pfungi3 | 80 | 23788.6 | 255.1 | 6291.3 | 127.1 |

TABLE 71

*Trichophyton tonsurans*

| Group | Probe Name | SEQ ID No: | 1st Intensity | S/N | 2nd Intensity | S/N |
|---|---|---|---|---|---|---|
| 1 | P0101 | 1 | 85.8 | 0.9 | 48.0 | 1.0 |
|   | P0102 | 2 | 89.0 | 0.9 | 46.9 | 1.0 |
|   | P0103 | 3 | 91.0 | 0.9 | 47.0 | 1.0 |
|   | P0104 | 4 | 84.3 | 0.9 | 46.2 | 1.0 |
| 2 | P0201 | 5 | 85.8 | 0.9 | 48.0 | 1.0 |
|   | P0202 | 6 | 89.0 | 0.9 | 46.9 | 1.0 |
|   | P0204 | 7 | 91.0 | 0.9 | 47.0 | 1.0 |
|   | P0205 | 8 | 84.3 | 0.9 | 46.2 | 1.0 |
| 3 | P0302 | 9 | 77.8 | 0.8 | 45.4 | 0.9 |
|   | P0303 | 10 | 80.6 | 0.8 | 45.8 | 0.9 |
|   | P0304 | 11 | 84.8 | 0.9 | 45.1 | 0.9 |
|   | P0305 | 12 | 78.7 | 0.8 | 44.1 | 0.9 |
| 4 | P0401 | 13 | 85.4 | 0.9 | 44.7 | 0.9 |
|   | P0402 | 14 | 83.7 | 0.8 | 45.3 | 0.9 |
|   | P0403 | 15 | 81.2 | 0.8 | 45.0 | 0.9 |
|   | P0404 | 16 | 85.7 | 0.9 | 48.8 | 1.0 |
| 5 | P0503 | 17 | 81.1 | 0.8 | 45.1 | 0.9 |
|   | P0502 | 18 | 80.1 | 0.8 | 44.0 | 1.0 |
| 6 | P0601 | 19 | 84.7 | 0.9 | 44.8 | 0.9 |
|   | P0602 | 20 | 77.8 | 0.8 | 45.4 | 0.9 |
|   | P0603 | 21 | 88.3 | 0.9 | 44.8 | 0.9 |
|   | P0604 | 22 | 83.9 | 0.8 | 46.0 | 0.9 |
| 7 | P0701 | 23 | 79.7 | 0.8 | 44.8 | 0.9 |
|   | P0702 | 24 | 327.0 | 3.3 | 55.1 | 1.1 |
|   | P0703 | 25 | 83.7 | 0.8 | 45.9 | 0.9 |
|   | P0704 | 26 | 90.5 | 0.9 | 44.5 | 0.9 |
| 8 | P0801 | 27 | 77.1 | 0.8 | 46.1 | 1.0 |
|   | P0803 | 28 | 82.8 | 0.8 | 45.4 | 0.9 |

TABLE 72

*Trichophyton tonsurans*

| Group | Probe Name | SEQ ID No: | 1st Intensity | S/N | 2nd Intensity | S/N |
|---|---|---|---|---|---|---|
| 9 | P0901 | 29 | 80.5 | 0.8 | 48.0 | 1.0 |
|   | P0902 | 30 | 83.2 | 0.8 | 45.6 | 0.9 |
|   | P0903 | 31 | 78.7 | 0.8 | 44.2 | 0.9 |
| 10 | P1102 | 32 | 79.0 | 0.8 | 52.4 | 1.1 |
|   | P1103 | 33 | 90.2 | 0.9 | 45.0 | 0.9 |
|   | P1104 | 34 | 78.8 | 0.8 | 44.4 | 0.9 |
| 11 | P2701 | 35 | 79.7 | 0.8 | 46.5 | 1.0 |
|   | P2702 | 36 | 81.8 | 0.8 | 46.3 | 1.0 |
| 12 | P2801 | 37 | 84.8 | 0.9 | 46.0 | 1.0 |
|   | P2802 | 38 | 85.3 | 0.9 | 47.8 | 1.0 |
| 13 | P3301 | 39 | 160.6 | 1.6 | 52.5 | 1.1 |
|   | P3302 | 40 | 86.7 | 0.9 | 46.8 | 1.0 |
| 14 | P2901 | 41 | 88.0 | 0.9 | 46.1 | 1.0 |
|   | P2902 | 42 | 82.4 | 0.8 | 45.4 | 0.9 |
|   | P2903 | 43 | 84.4 | 0.9 | 45.9 | 0.9 |
| 15 | P3001 | 44 | 80.3 | 0.8 | 45.3 | 0.9 |
|   | P3002 | 45 | 83.6 | 0.8 | 44.9 | 0.9 |
|   | P3003 | 46 | 79.4 | 0.8 | 46.0 | 1.0 |
| 16 | P1901 | 47 | 83.0 | 0.8 | 45.8 | 0.9 |
|   | P1902 | 48 | 88.7 | 0.9 | 45.4 | 0.9 |
|   | P1903 | 49 | 591.0 | 6.0 | 104.8 | 2.2 |
|   | P1904 | 50 | 83.9 | 0.9 | 46.2 | 1.0 |
| 17 | P2001 | 51 | 89.8 | 0.9 | 48.6 | 1.0 |
|   | P2002 | 52 | 78.1 | 0.8 | 45.8 | 0.9 |
| 18 | P2105 | 53 | 80.6 | 0.8 | 47.3 | 1.0 |
|   | P2102 | 54 | 112.4 | 1.1 | 46.0 | 1.0 |
|   | P2103 | 55 | 85.2 | 0.9 | 45.5 | 0.9 |

TABLE 73

Trichophyton tonsurans

| Group | Probe Name | SEQ ID No: | 1st Intensity | 1st S/N | 2nd Intensity | 2nd S/N |
|---|---|---|---|---|---|---|
| 19 | P2205 | 56 | 84.0 | 0.8 | 61.9 | 1.3 |
|  | P2202 | 57 | 93.9 | 0.9 | 44.1 | 0.9 |
|  | P2203 | 58 | 282.6 | 2.9 | 58.5 | 1.2 |
|  | P2204 | 59 | 83.3 | 0.8 | 46.4 | 1.0 |
| 20 | P2302 | 60 | 146.5 | 1.5 | 47.8 | 1.0 |
|  | P2306 | 61 | 85.8 | 0.9 | 45.8 | 0.9 |
|  | P2305 | 62 | 83.6 | 0.8 | 46.4 | 1.0 |
| 21 | P2405 | 63 | 2774.8 | 28.0 | 142.9 | 3.0 |
|  | P2402 | 64 | 23274.1 | 234.9 | 372.4 | 7.7 |
|  | P2403 | 65 | 1086.3 | 11.0 | 4577.2 | 94.6 |
| 22 | P2501 | 66 | 134.5 | 1.4 | 48.7 | 1.0 |
|  | P2502 | 67 | 5613.4 | 56.7 | 639.2 | 13.2 |
| 23 | P2604 | 68 | 126.6 | 1.3 | 45.3 | 0.9 |
|  | P2601 | 69 | 85.6 | 0.9 | 47.1 | 1.0 |
| 24 | P3101 | 70 | 162.8 | 1.6 | 49.7 | 1.0 |
|  | P3102 | 71 | 12628.9 | 127.5 | 2255.1 | 46.6 |
| 25 | P3201 | 72 | 392.8 | 4.0 | 94.4 | 2.0 |
|  | P3202 | 73 | 84.2 | 0.9 | 46.5 | 1.0 |
| 26 | P3401 | 74 | 134.1 | 1.4 | 51.2 | 1.1 |
|  | P3402 | 75 | 125.9 | 1.3 | 51.6 | 1.1 |
| 27 | Ptricho1 | 76 | 1290.9 | 13.0 | 172.5 | 3.6 |
| 28 | Pfila1 | 77 | 55624.0 | 561.5 | 14656.2 | 302.8 |
| 29 | Pfungi1 | 78 | 25293.5 | 255.3 | 7823.6 | 161.6 |
|  | Pfungi2 | 79 | 19703.0 | 198.9 | 5647.9 | 116.7 |
|  | Pfungi3 | 80 | 26395.9 | 266.5 | 7930.3 | 163.8 |

TABLE 74

Trichophyton verrucosum

| Group | Probe Name | SEQ ID No: | 1st Intensity | 1st S/N | 2nd Intensity | 2nd S/N |
|---|---|---|---|---|---|---|
| 1 | P0101 | 1 | 89.6 | 0.8 | 49.5 | 0.9 |
|  | P0102 | 2 | 92.5 | 0.8 | 49.5 | 0.9 |
|  | P0103 | 3 | 91.4 | 0.8 | 74.9 | 1.4 |
|  | P0104 | 4 | 90.7 | 0.8 | 49.3 | 0.9 |
| 2 | P0201 | 5 | 89.6 | 0.8 | 49.5 | 0.9 |
|  | P0202 | 6 | 92.5 | 0.8 | 49.5 | 0.9 |
|  | P0204 | 7 | 91.4 | 0.8 | 74.9 | 1.4 |
|  | P0205 | 8 | 90.7 | 0.8 | 49.3 | 0.9 |
| 3 | P0302 | 9 | 91.7 | 0.8 | 48.7 | 0.9 |
|  | P0303 | 10 | 80.1 | 0.7 | 48.7 | 0.9 |
|  | P0304 | 11 | 87.4 | 0.8 | 80.6 | 1.5 |
|  | P0305 | 12 | 90.6 | 0.8 | 51.6 | 0.9 |
| 4 | P0401 | 13 | 96.9 | 0.9 | 48.4 | 0.9 |
|  | P0402 | 14 | 91.7 | 0.8 | 50.7 | 0.9 |
|  | P0403 | 15 | 88.8 | 0.8 | 51.0 | 0.9 |
|  | P0404 | 16 | 94.2 | 0.8 | 129.7 | 2.4 |
| 5 | P0503 | 17 | 86.8 | 0.8 | 48.3 | 0.9 |
|  | P0502 | 18 | 79.5 | 0.7 | 47.9 | 0.9 |
| 6 | P0601 | 19 | 91.4 | 0.8 | 56.0 | 1.0 |
|  | P0602 | 20 | 89.1 | 0.8 | 48.0 | 0.9 |
|  | P0603 | 21 | 94.2 | 0.8 | 48.7 | 0.9 |
|  | P0604 | 22 | 82.3 | 0.7 | 238.7 | 4.3 |
| 7 | P0701 | 23 | 92.0 | 0.8 | 51.7 | 0.9 |
|  | P0702 | 24 | 152.7 | 1.4 | 159.9 | 2.9 |
|  | P0703 | 25 | 95.6 | 0.9 | 49.3 | 0.9 |
|  | P0704 | 26 | 89.9 | 0.8 | 50.4 | 0.9 |
| 8 | P0801 | 27 | 100.2 | 0.9 | 49.7 | 0.9 |
|  | P0803 | 28 | 82.3 | 0.7 | 50.5 | 0.9 |

TABLE 75

Trichophyton verrucosum

| Group | Probe Name | SEQ ID No: | 1st Intensity | 1st S/N | Intensity | S/N |
|---|---|---|---|---|---|---|
| 9 | P0901 | 29 | 95.0 | 0.8 | 51.6 | 0.9 |
|  | P0902 | 30 | 96.4 | 0.9 | 71.7 | 1.3 |
|  | P0903 | 31 | 99.9 | 0.9 | 50.6 | 0.9 |
| 10 | P1102 | 32 | 87.8 | 0.8 | 62.0 | 1.1 |
|  | P1103 | 33 | 93.4 | 0.8 | 46.8 | 0.8 |
|  | P1104 | 34 | 82.3 | 0.7 | 53.8 | 1.0 |
| 11 | P2701 | 35 | 90.8 | 0.8 | 49.4 | 0.9 |
|  | P2702 | 36 | 91.2 | 0.8 | 50.4 | 0.9 |
| 12 | P2801 | 37 | 99.3 | 0.9 | 50.4 | 0.9 |
|  | P2802 | 38 | 96.5 | 0.9 | 104.3 | 1.9 |
| 13 | P3301 | 39 | 114.1 | 1.0 | 74.2 | 1.3 |
|  | P3302 | 40 | 92.5 | 0.8 | 49.6 | 0.9 |
| 14 | P2901 | 41 | 98.8 | 0.9 | 48.3 | 0.9 |
|  | P2902 | 42 | 86.5 | 0.8 | 49.0 | 0.9 |
|  | P2903 | 43 | 94.4 | 0.8 | 49.3 | 0.9 |
| 15 | P3001 | 44 | 87.1 | 0.8 | 54.1 | 1.0 |
|  | P3002 | 45 | 97.0 | 0.9 | 51.3 | 0.9 |
|  | P3003 | 46 | 99.9 | 0.9 | 51.5 | 0.9 |
| 16 | P1901 | 47 | 94.0 | 0.8 | 53.8 | 1.0 |
|  | P1902 | 48 | 88.9 | 0.8 | 51.6 | 0.9 |
|  | P1903 | 49 | 102.4 | 0.9 | 113.1 | 2.1 |
|  | P1904 | 50 | 95.0 | 0.8 | 53.8 | 1.0 |
| 17 | P2001 | 51 | 95.3 | 0.9 | 55.7 | 1.0 |
|  | P2002 | 52 | 92.1 | 0.8 | 51.6 | 0.9 |
| 18 | P2105 | 53 | 103.6 | 0.9 | 51.8 | 0.9 |
|  | P2102 | 54 | 91.7 | 0.8 | 59.5 | 1.1 |
|  | P2103 | 55 | 91.4 | 0.8 | 54.2 | 1.0 |

TABLE 76

Trichophyton verrucosum

| Group | Probe Name | SEQ ID No: | 1st Intensity | 1st S/N | 2nd Intensity | 2nd S/N |
|---|---|---|---|---|---|---|
| 19 | P2205 | 56 | 111.9 | 1.0 | 117.6 | 2.1 |
|  | P2202 | 57 | 898.8 | 8.0 | 920.7 | 16.7 |
|  | P2203 | 58 | 1110.9 | 9.9 | 1731.7 | 31.4 |
|  | P2204 | 59 | 183.7 | 16.4 | 1903.4 | 34.5 |
| 20 | P2302 | 60 | 96.9 | 0.9 | 50.3 | 0.9 |
|  | P2306 | 61 | 83.7 | 0.7 | 55.2 | 1.0 |
|  | P2305 | 62 | 90.1 | 0.8 | 51.4 | 0.9 |
| 21 | P2405 | 63 | 89.0 | 0.8 | 54.8 | 1.0 |
|  | P2402 | 64 | 191.4 | 1.7 | 49.4 | 0.9 |
|  | P2403 | 65 | 86.2 | 0.8 | 526.4 | 9.6 |
| 22 | P2501 | 66 | 14413.9 | 128.8 | 9419.7 | 170.9 |
|  | P2502 | 67 | 6766.2 | 60.4 | 5521.3 | 100.2 |
| 23 | P2604 | 68 | 95.8 | 0.9 | 53.4 | 1.0 |
|  | P2601 | 69 | 101.4 | 0.9 | 52.5 | 1.0 |
| 24 | P3101 | 70 | 88.5 | 0.8 | 50.3 | 0.9 |
|  | P3102 | 71 | 85.6 | 0.8 | 53.4 | 1.0 |
| 25 | P3201 | 72 | 86.6 | 0.8 | 84.7 | 1.5 |
|  | P3202 | 73 | 82.5 | 0.7 | 50.5 | 0.9 |
| 26 | P3401 | 74 | 91.6 | 0.8 | 52.6 | 1.0 |
|  | P3402 | 75 | 91.1 | 0.8 | 53.4 | 1.0 |
| 27 | Ptricho1 | 76 | 8297.6 | 74.1 | 9387.2 | 170.3 |
| 28 | Pfila1 | 77 | 21048.1 | 188.0 | 18000.8 | 326.6 |
| 29 | Pfungi1 | 78 | 13402.2 | 119.7 | 8912.2 | 161.7 |
|  | Pfungi2 | 79 | 10136.2 | 90.5 | 7677.3 | 139.3 |
|  | Pfungi3 | 80 | 14086.3 | 125.8 | 9723.9 | 176.4 |

TABLE 77

*Trichophyton violaceum*

| Group | Probe Name | SEQ ID No: | 1st Intensity | 1st S/N | 2nd Intensity | 2nd S/N |
|---|---|---|---|---|---|---|
| 1 | P0101 | 1 | 84.8 | 0.7 | 48.3 | 0.9 |
|  | P0102 | 2 | 94.2 | 0.8 | 50.9 | 1.0 |
|  | P0103 | 3 | 90.3 | 0.8 | 52.9 | 1.0 |
|  | P0104 | 4 | 87.1 | 0.7 | 49.7 | 0.9 |
| 2 | P0201 | 5 | 84.8 | 0.7 | 48.3 | 0.9 |
|  | P0202 | 6 | 94.2 | 0.8 | 50.9 | 1.0 |
|  | P0204 | 7 | 90.3 | 0.8 | 52.9 | 1.0 |
|  | P0205 | 8 | 87.1 | 0.7 | 49.7 | 0.9 |
| 3 | P0302 | 9 | 86.5 | 0.7 | 49.3 | 0.9 |
|  | P0303 | 10 | 90.9 | 0.8 | 50.0 | 1.0 |
|  | P0304 | 11 | 84.6 | 0.7 | 50.5 | 1.0 |
|  | P0305 | 12 | 89.0 | 0.8 | 49.6 | 0.9 |
| 4 | P0401 | 13 | 100.2 | 0.9 | 48.1 | 0.9 |
|  | P0402 | 14 | 93.1 | 0.8 | 50.2 | 1.0 |
|  | P0403 | 15 | 92.1 | 0.8 | 49.5 | 0.9 |
|  | P0404 | 16 | 82.0 | 0.7 | 75.8 | 1.4 |
| 5 | P0503 | 17 | 89.1 | 0.8 | 49.3 | 1.0 |
|  | P0502 | 18 | 104.1 | 0.9 | 50.4 | 0.9 |
| 6 | P0601 | 19 | 90.9 | 0.8 | 49.9 | 0.9 |
|  | P0602 | 20 | 104.8 | 0.9 | 49.0 | 0.9 |
|  | P0603 | 21 | 81.2 | 0.7 | 48.0 | 0.9 |
|  | P0604 | 22 | 92.0 | 0.8 | 70.0 | 1.3 |
| 7 | P0701 | 23 | 85.0 | 0.7 | 49.3 | 0.9 |
|  | P0702 | 24 | 172.0 | 1.5 | 52.0 | 1.0 |
|  | P0703 | 25 | 80.0 | 0.7 | 50.0 | 1.0 |
|  | P0704 | 26 | 81.1 | 0.7 | 49.1 | 0.9 |
| 8 | P0801 | 27 | 84.0 | 0.7 | 48.6 | 0.9 |
|  | P0803 | 28 | 95.3 | 0.8 | 49.3 | 0.9 |

TABLE 78

*Trichophyton violaceum*

| Group | Probe Name | SEQ ID No: | 1st Intensity | 1st S/N | 2nd Intensity | 2nd S/N |
|---|---|---|---|---|---|---|
| 9 | P0901 | 29 | 86.1 | 0.7 | 51.7 | 1.0 |
|  | P0902 | 30 | 86.0 | 0.7 | 51.5 | 1.0 |
|  | P0903 | 31 | 83.5 | 0.7 | 47.8 | 0.9 |
| 10 | P1102 | 32 | 93.8 | 0.8 | 58.3 | 1.1 |
|  | P1103 | 33 | 91.4 | 0.8 | 49.6 | 0.9 |
|  | P1104 | 34 | 89.9 | 0.8 | 49.7 | 0.9 |
| 11 | P2701 | 35 | 215.8 | 1.9 | 52.9 | 1.0 |
|  | P2702 | 36 | 100.5 | 0.9 | 50.3 | 1.0 |
| 12 | P2801 | 37 | 89.3 | 0.8 | 49.0 | 0.9 |
|  | P2802 | 38 | 92.1 | 0.8 | 54.8 | 1.0 |
| 13 | P3301 | 39 | 120.0 | 1.0 | 50.9 | 1.0 |
|  | P3302 | 40 | 75.8 | 0.7 | 49.6 | 0.9 |
| 14 | P2901 | 41 | 103.8 | 0.9 | 48.3 | 0.9 |
|  | P2902 | 42 | 92.2 | 0.8 | 48.3 | 0.9 |
|  | P2903 | 43 | 94.0 | 0.8 | 50.8 | 1.0 |
| 15 | P3001 | 44 | 94.7 | 0.8 | 49.7 | 0.9 |
|  | P3002 | 45 | 96.8 | 0.8 | 48.9 | 0.9 |
|  | P3003 | 46 | 83.0 | 0.7 | 50.7 | 1.0 |
| 16 | P1901 | 47 | 95.0 | 0.8 | 50.2 | 1.0 |
|  | P1902 | 48 | 99.8 | 0.9 | 49.1 | 0.9 |
|  | P1903 | 49 | 95.8 | 0.8 | 54.3 | 1.0 |
|  | P1904 | 50 | 86.2 | 0.7 | 51.4 | 1.0 |
| 17 | P2001 | 51 | 92.2 | 0.8 | 56.4 | 1.1 |
|  | P2002 | 52 | 90.1 | 0.8 | 50.0 | 1.0 |
| 18 | P2105 | 53 | 93.3 | 0.8 | 51.1 | 1.0 |
|  | P2102 | 54 | 81.3 | 0.7 | 48.8 | 0.9 |
|  | P2103 | 55 | 100.9 | 0.9 | 50.5 | 1.0 |

TABLE 79

*Trichophyton violaceum*

| Group | Probe Name | SEQ ID No: | 1st Intensity | 1st S/N | 2nd Intensity | 2nd S/N |
|---|---|---|---|---|---|---|
| 19 | P2205 | 56 | 103.4 | 0.9 | 71.4 | 1.4 |
|  | P2202 | 57 | 95.5 | 0.8 | 49.1 | 0.9 |
|  | P2203 | 58 | 1174.3 | 10.1 | 678.9 | 12.9 |
|  | P2204 | 59 | 87.4 | 0.7 | 50.6 | 1.0 |
| 20 | P2302 | 60 | 132.8 | 1.1 | 50.6 | 1.0 |
|  | P2306 | 61 | 93.9 | 0.8 | 59.7 | 1.1 |
|  | P2305 | 62 | 111.3 | 1.0 | 51.0 | 1.0 |
| 21 | P2405 | 63 | 96.1 | 0.8 | 48.9 | 0.9 |
|  | P2402 | 64 | 107.0 | 0.9 | 49.9 | 0.9 |
|  | P2403 | 65 | 83.5 | 0.7 | 55.3 | 1.1 |
| 22 | P2501 | 66 | 85.4 | 0.7 | 49.5 | 0.9 |
|  | P2502 | 67 | 1472.1 | 12.6 | 297.3 | 5.7 |
| 23 | P2604 | 68 | 17034.1 | 146.1 | 798.0 | 15.2 |
|  | P2601 | 69 | 17648.8 | 151.4 | 765.4 | 14.6 |
| 24 | P3101 | 70 | 88.2 | 0.8 | 49.5 | 0.9 |
|  | P3102 | 71 | 93.7 | 0.8 | 49.1 | 0.9 |
| 25 | P3201 | 72 | 91.3 | 0.8 | 50.7 | 1.0 |
|  | P3202 | 73 | 91.4 | 0.8 | 53.2 | 1.0 |
| 26 | P3401 | 74 | 616.5 | 5.3 | 164.8 | 3.1 |
|  | P3042 | 75 | 637.0 | 5.5 | 161.6 | 3.1 |
| 27 | Ptricho1 | 76 | 5986.7 | 51.3 | 979.8 | 18.7 |
| 28 | Pfila1 | 77 | 33273.3 | 285.4 | 17881.6 | 340.4 |
| 29 | Pfungi1 | 78 | 15805.5 | 135.6 | 1039.1 | 19.8 |
|  | Pfungi2 | 79 | 12582.6 | 107.9 | 779.6 | 14.8 |
|  | Pfungi3 | 80 | 18317.5 | 157.1 | 1676.2 | 31.9 |

TABLE 80

*Arthroderma vanbreuseghemii*

| Group | Probe Name | SEQ ID No: | 1st Intensity | 1st S/N | 2nd Intensity | 2nd S/N |
|---|---|---|---|---|---|---|
| 1 | P0101 | 1 | 75.0 | 0.8 | 50.6 | 1.0 |
|  | P0102 | 2 | 77.9 | 0.8 | 51.4 | 1.0 |
|  | P0103 | 3 | 75.7 | 0.8 | 67.5 | 1.3 |
|  | P0104 | 4 | 83.2 | 0.8 | 50.1 | 1.0 |
| 2 | P0201 | 5 | 75.0 | 0.8 | 50.6 | 1.0 |
|  | P0202 | 6 | 77.9 | 0.8 | 51.4 | 1.0 |
|  | P0204 | 7 | 75.7 | 0.8 | 67.5 | 1.3 |
|  | P0205 | 8 | 83.2 | 0.8 | 50.1 | 1.0 |
| 3 | P0302 | 9 | 73.0 | 0.7 | 49.1 | 0.9 |
|  | P0303 | 10 | 73.7 | 0.7 | 48.0 | 0.9 |
|  | P0304 | 11 | 78.1 | 0.8 | 53.2 | 1.0 |
|  | P0305 | 12 | 72.3 | 0.7 | 48.4 | 0.9 |
| 4 | P0401 | 13 | 83.0 | 0.8 | 48.3 | 0.9 |
|  | P0402 | 14 | 73.8 | 0.7 | 49.7 | 0.9 |
|  | P0403 | 15 | 76.0 | 0.8 | 52.2 | 1.0 |
|  | P0404 | 16 | 76.7 | 0.8 | 100.4 | 1.9 |
| 5 | P0503 | 17 | 73.2 | 0.7 | 49.9 | 0.9 |
|  | P0502 | 18 | 74.1 | 0.7 | 49.9 | 0.9 |
| 6 | P0601 | 19 | 72.5 | 0.7 | 51.7 | 1.0 |
|  | P0602 | 20 | 79.6 | 0.8 | 48.4 | 0.9 |
|  | P0603 | 21 | 74.7 | 0.8 | 49.8 | 1.0 |
|  | P0604 | 22 | 81.3 | 0.8 | 149.6 | 2.9 |
| 7 | P0701 | 23 | 74.3 | 0.7 | 48.8 | 0.9 |
|  | P0702 | 24 | 140.6 | 1.4 | 83.5 | 1.6 |
|  | P0703 | 25 | 74.7 | 0.8 | 49.8 | 1.0 |
|  | P0704 | 26 | 79.2 | 0.8 | 48.4 | 0.9 |
| 8 | P0801 | 27 | 72.3 | 0.7 | 50.3 | 1.0 |
|  | P0803 | 28 | 76.2 | 0.8 | 49.5 | 0.9 |

TABLE 81

*Arthroderma vanbreuseghemii*

| Group | Probe Name | SEQ ID No: | 1st Intensity | S/N | 2nd Intensity | S/N |
|---|---|---|---|---|---|---|
| 9 | P0901 | 29 | 77.3 | 0.8 | 53.0 | 1.0 |
|   | P0902 | 30 | 73.8 | 0.7 | 67.8 | 1.3 |
|   | P0903 | 31 | 75.2 | 0.8 | 50.3 | 1.0 |
| 10 | P1102 | 32 | 75.6 | 0.8 | 60.3 | 1.2 |
|   | P1103 | 33 | 72.7 | 0.7 | 49.9 | 1.0 |
|   | P1104 | 34 | 70.9 | 0.7 | 49.6 | 0.9 |
| 11 | P2701 | 35 | 75.6 | 0.8 | 49.6 | 0.9 |
|   | P2702 | 36 | 75.3 | 0.8 | 49.1 | 0.9 |
| 12 | P2801 | 37 | 75.8 | 0.8 | 48.8 | 0.9 |
|   | P2802 | 38 | 82.2 | 0.8 | 131.4 | 2.5 |
| 13 | P3301 | 39 | 128.3 | 1.3 | 61.9 | 1.2 |
|   | P3302 | 40 | 75.3 | 0.8 | 48.4 | 0.9 |
| 14 | P2901 | 41 | 82.8 | 0.8 | 49.9 | 1.0 |
|   | P2902 | 42 | 71.6 | 0.7 | 48.5 | 0.9 |
|   | P2903 | 43 | 67.4 | 0.7 | 48.4 | 0.9 |
| 15 | P3001 | 44 | 74.2 | 0.7 | 46.8 | 0.9 |
|   | P3002 | 45 | 77.8 | 0.8 | 48.3 | 0.9 |
|   | P3003 | 46 | 72.1 | 0.7 | 48.4 | 0.9 |
| 16 | P1901 | 47 | 77.3 | 0.8 | 54.3 | 1.0 |
|   | P1902 | 48 | 75.9 | 0.8 | 48.3 | 0.9 |
|   | P1903 | 49 | 385.2 | 3.9 | 138.4 | 2.6 |
|   | P1904 | 50 | 78.4 | 0.8 | 51.9 | 1.0 |
| 17 | P2001 | 51 | 78.9 | 0.8 | 57.6 | 1.1 |
|   | P2002 | 52 | 76.8 | 0.8 | 49.1 | 0.9 |
| 18 | P2105 | 53 | 77.7 | 0.8 | 51.3 | 1.0 |
|   | P2102 | 54 | 79.7 | 0.8 | 55.5 | 1.1 |
|   | P2103 | 55 | 74.3 | 0.7 | 48.8 | 0.9 |

TABLE 82

*Arthroderma vanbreuseghemii*

| Group | Probe Name | SEQ ID No: | 1st Intensity | S/N | 2nd Intensity | S/N |
|---|---|---|---|---|---|---|
| 19 | P2205 | 56 | 85.3 | 0.9 | 72.9 | 1.4 |
|   | P2202 | 57 | 75.7 | 0.8 | 50.2 | 1.0 |
|   | P2203 | 58 | 132.0 | 1.3 | 99.4 | 1.9 |
|   | P2204 | 59 | 79.8 | 0.8 | 49.3 | 0.9 |
| 20 | P2302 | 60 | 82.9 | 0.8 | 87.3 | 1.7 |
|   | P2306 | 61 | 82.2 | 0.8 | 49.8 | 1.0 |
|   | P2305 | 62 | 75.4 | 0.8 | 51.3 | 1.0 |
| 21 | P2405 | 63 | 81.3 | 0.8 | 53.7 | 1.0 |
|   | P2402 | 64 | 6476.4 | 65.1 | 52.5 | 1.0 |
|   | P2403 | 65 | 77.0 | 0.8 | 1036.1 | 19.8 |
| 22 | P2501 | 66 | 84.1 | 0.8 | 64.2 | 1.2 |
|   | P2502 | 67 | 3635.5 | 36.6 | 881.0 | 16.8 |
| 23 | P2604 | 68 | 84.3 | 0.8 | 47.6 | 0.9 |
|   | P2601 | 69 | 76.7 | 0.8 | 58.2 | 1.1 |
| 24 | P3101 | 70 | 4336.5 | 43.6 | 581.6 | 11.1 |
|   | P3102 | 71 | 18609.4 | 187.2 | 5445.7 | 104.0 |
| 25 | P3201 | 72 | 247.7 | 2.5 | 119.9 | 2.3 |
|   | P3202 | 73 | 75.2 | 0.8 | 48.8 | 0.9 |
| 26 | P3401 | 74 | 152.3 | 1.5 | 95.5 | 1.8 |
|   | P3402 | 75 | 1610.4 | 16.2 | 756.0 | 14.4 |
| 27 | Ptricho1 | 76 | 679.7 | 6.8 | 517.9 | 9.9 |
| 28 | Pfila1 | 77 | 41281.2 | 415.3 | 17554.3 | 335.2 |
| 29 | Pfungi1 | 78 | 21701.2 | 218.3 | 7789.3 | 148.7 |
|   | Pfungi2 | 79 | 17010.4 | 171.1 | 6768.1 | 129.2 |
|   | Pfungi3 | 80 | 23172.8 | 233.1 | 8751.6 | 167.1 |

TABLE 83

*Arthroderma incurvatum*

| Group | Probe Name | SEQ ID No: | 1st Intensity | S/N | 2nd Intensity | S/N |
|---|---|---|---|---|---|---|
| 1 | P0101 | 1 | 105.2 | 1.0 | 47.8 | 1.0 |
|   | P0102 | 2 | 105.1 | 0.9 | 47.7 | 1.0 |
|   | P0103 | 3 | 102.2 | 0.9 | 47.3 | 1.0 |
|   | P0104 | 4 | 104.9 | 0.9 | 46.5 | 0.9 |
| 2 | P0201 | 5 | 105.2 | 1.0 | 47.8 | 1.0 |
|   | P0202 | 6 | 105.1 | 0.9 | 47.7 | 1.0 |
|   | P0204 | 7 | 102.2 | 0.9 | 47.3 | 1.0 |
|   | P0205 | 8 | 104.9 | 0.9 | 46.5 | 0.9 |
| 3 | P0302 | 9 | 98.9 | 0.9 | 45.5 | 0.9 |
|   | P0303 | 10 | 101.5 | 0.9 | 47.2 | 1.0 |
|   | P0304 | 11 | 93.6 | 0.8 | 46.2 | 0.9 |
|   | P0305 | 12 | 91.1 | 0.8 | 45.7 | 0.9 |
| 4 | P0401 | 13 | 102.3 | 0.9 | 46.9 | 0.9 |
|   | P0402 | 14 | 98.6 | 0.9 | 46.5 | 0.9 |
|   | P0403 | 15 | 93.3 | 0.8 | 45.7 | 0.9 |
|   | P0404 | 16 | 101.5 | 0.9 | 53.0 | 1.1 |
| 5 | P0503 | 17 | 86.9 | 0.8 | 45.8 | 1.0 |
|   | P0502 | 18 | 91.1 | 0.8 | 47.5 | 0.9 |
| 6 | P0601 | 19 | 92.8 | 0.8 | 47.3 | 1.0 |
|   | P0602 | 20 | 95.7 | 0.9 | 45.4 | 0.9 |
|   | P0603 | 21 | 98.4 | 0.9 | 47.4 | 1.0 |
|   | P0604 | 22 | 96.5 | 0.9 | 49.8 | 1.0 |
| 7 | P0701 | 23 | 91.7 | 0.8 | 47.8 | 1.0 |
|   | P0702 | 24 | 145.0 | 1.3 | 45.9 | 0.9 |
|   | P0703 | 25 | 97.2 | 0.9 | 45.9 | 0.9 |
|   | P0704 | 26 | 102.3 | 0.9 | 47.9 | 1.0 |
| 8 | P0801 | 27 | 96.7 | 0.9 | 45.8 | 0.9 |
|   | P0803 | 28 | 96.2 | 0.9 | 46.5 | 0.9 |

TABLE 84

*Arthroderma incurvatum*

| Group | Probe Name | SEQ ID No: | 1st Intensity | S/N | 2nd Intensity | S/N |
|---|---|---|---|---|---|---|
| 9 | P0901 | 29 | 97.4 | 0.9 | 47.8 | 1.0 |
|   | P0902 | 30 | 95.7 | 0.9 | 46.3 | 0.9 |
|   | P0903 | 31 | 94.5 | 0.9 | 46.2 | 0.9 |
| 10 | P1102 | 32 | 95.7 | 0.9 | 49.7 | 1.0 |
|   | P1103 | 33 | 98.2 | 0.9 | 46.1 | 0.9 |
|   | P1104 | 34 | 93.9 | 0.8 | 46.6 | 0.9 |
| 11 | P2701 | 35 | 94.2 | 0.9 | 46.9 | 0.9 |
|   | P2702 | 36 | 91.6 | 0.8 | 47.3 | 1.0 |
| 12 | P2801 | 37 | 96.5 | 0.9 | 45.9 | 0.9 |
|   | P2802 | 38 | 95.8 | 0.9 | 48.2 | 1.0 |
| 13 | P3301 | 39 | 157.0 | 1.4 | 47.5 | 1.0 |
|   | P3302 | 40 | 90.7 | 0.8 | 46.9 | 0.9 |
| 14 | P2901 | 41 | 102.8 | 0.9 | 45.8 | 0.9 |
|   | P2902 | 42 | 90.0 | 0.8 | 46.2 | 0.9 |
|   | P2903 | 43 | 89.2 | 0.8 | 47.0 | 0.9 |
| 15 | P3001 | 44 | 97.1 | 0.9 | 46.2 | 0.9 |
|   | P3002 | 45 | 91.1 | 0.8 | 46.4 | 0.9 |
|   | P3003 | 46 | 92.5 | 0.8 | 46.3 | 0.9 |
| 16 | P1901 | 47 | 109.5 | 1.0 | 47.2 | 1.0 |
|   | P1902 | 48 | 99.3 | 0.9 | 46.8 | 0.9 |
|   | P1903 | 49 | 108.0 | 1.0 | 46.4 | 0.9 |
|   | P1904 | 50 | 93.4 | 0.8 | 47.3 | 1.0 |
| 17 | P2001 | 51 | 112.2 | 1.0 | 50.7 | 1.0 |
|   | P2002 | 52 | 101.6 | 0.9 | 46.0 | 0.9 |
| 18 | P2105 | 53 | 124.1 | 1.1 | 47.1 | 1.0 |
|   | P2102 | 54 | 13322.3 | 120.4 | 394.6 | 8.0 |
|   | P2103 | 55 | 160.2 | 1.4 | 48.5 | 1.0 |

TABLE 85

*Arthroderma incurvatum*

| Group | Probe Name | SEQ ID No: | 1st Intensity | 1st S/N | 2nd Intensity | 2nd S/N |
|---|---|---|---|---|---|---|
| 19 | P2205 | 56 | 107.1 | 1.0 | 59.4 | 1.2 |
|  | P2202 | 57 | 101.1 | 0.9 | 47.0 | 0.9 |
|  | P2203 | 58 | 125.7 | 1.1 | 50.0 | 1.0 |
|  | P2204 | 59 | 91.0 | 0.8 | 46.6 | 0.9 |
| 20 | P2302 | 60 | 86.2 | 0.8 | 47.3 | 1.0 |
|  | P2306 | 61 | 93.8 | 0.8 | 46.6 | 0.9 |
|  | P2305 | 62 | 91.1 | 0.8 | 46.8 | 0.9 |
| 21 | P2405 | 63 | 83.4 | 0.8 | 47.1 | 1.0 |
|  | P2402 | 64 | 136.9 | 1.2 | 46.2 | 0.9 |
|  | P2403 | 65 | 89.1 | 0.8 | 47.7 | 1.0 |
| 22 | P2501 | 66 | 93.9 | 0.8 | 47.8 | 1.0 |
|  | P2502 | 67 | 1099.3 | 9.9 | 60.4 | 1.2 |
| 23 | P2604 | 68 | 95.3 | 0.9 | 46.6 | 0.9 |
|  | P2601 | 69 | 94.1 | 0.9 | 45.7 | 0.9 |
| 24 | P3101 | 70 | 98.3 | 0.9 | 46.7 | 0.9 |
|  | P3102 | 71 | 94.3 | 0.9 | 45.8 | 0.9 |
| 25 | P3201 | 72 | 10494.8 | 94.8 | 212.8 | 4.3 |
|  | P3202 | 73 | 32823.1 | 296.6 | 859.3 | 17.3 |
| 26 | P3401 | 74 | 104.0 | 0.9 | 49.9 | 1.0 |
|  | P3402 | 75 | 103.8 | 0.9 | 49.7 | 1.0 |
| 27 | Ptricho1 | 76 | 14541.6 | 131.4 | 572.1 | 11.5 |
| 28 | Pfila1 | 77 | 32440.4 | 293.2 | 1685.6 | 34.0 |
| 29 | Pfungi1 | 78 | 17498.3 | 158.1 | 668.8 | 13.5 |
|  | Pfungi2 | 79 | 7239.9 | 65.4 | 269.7 | 5.4 |
|  | Pfungi3 | 80 | 16399.9 | 148.2 | 839.4 | 16.9 |

TABLE 86

*Trichophyton interdigitale*

| Group | Probe Name | SEQ ID No: | 1st Intensity | 1st S/N | 2nd Intensity | 2nd S/N |
|---|---|---|---|---|---|---|
| 1 | P0101 | 1 | 112.5 | 1.0 | 86.3 | 0.7 |
|  | P0102 | 2 | 133.0 | 1.2 | 131.0 | 1.1 |
|  | P0103 | 3 | 205.3 | 1.8 | 170.8 | 1.5 |
|  | P0104 | 4 | 142.7 | 1.3 | 104.1 | 0.9 |
| 2 | P0201 | 5 | 123.7 | 1.1 | 81.8 | 0.7 |
|  | P0202 | 6 | 135.7 | 1.2 | 106.3 | 0.9 |
|  | P0204 | 7 | 241.8 | 2.1 | 364.4 | 3.1 |
|  | P0205 | 8 | 156.4 | 1.4 | 121.7 | 1.0 |
| 3 | P0302 | 9 | 122.1 | 1.1 | 86.7 | 0.7 |
|  | P0303 | 10 | 137.4 | 1.2 | 92.8 | 0.8 |
|  | P0304 | 11 | 113.4 | 1.0 | 306.1 | 2.6 |
|  | P0305 | 12 | 106.6 | 0.9 | 95.3 | 0.8 |
| 4 | P0401 | 13 | 165.4 | 1.5 | 120.6 | 1.0 |
|  | P0402 | 14 | 149.4 | 1.3 | 107.1 | 0.9 |
|  | P0403 | 15 | 130.3 | 1.2 | 96.9 | 0.8 |
|  | P0404 | 16 | 113.9 | 1.0 | 183.5 | 1.6 |
| 5 | P0503 | 17 | 100.7 | 0.9 | 96.6 | 0.8 |
|  | P0502 | 18 | 133.9 | 1.2 | 92.5 | 0.8 |
| 6 | P0601 | 19 | 153.3 | 1.4 | 98.3 | 0.8 |
|  | P0602 | 20 | 133.9 | 1.0 | 86.9 | 0.7 |
|  | P0603 | 21 | 199.3 | 1.8 | 124.8 | 1.1 |
|  | P0604 | 22 | 117.9 | 1.0 | 86.0 | 0.7 |
| 7 | P0701 | 23 | 191.2 | 1.7 | 169.6 | 1.5 |
|  | P0702 | 24 | 172.1 | 1.5 | 235.1 | 2.0 |
|  | P0703 | 25 | 163.1 | 1.4 | 517.6 | 4.4 |
|  | P0704 | 26 | 185.2 | 1.6 | 111.9 | 1.0 |
| 8 | P0801 | 27 | 141.2 | 1.2 | 101.2 | 0.9 |
|  | P0803 | 28 | 140.5 | 1.2 | 95.9 | 0.8 |

TABLE 87

*Trichophyton interdigitale*

| Group | Probe Name | SEQ ID No: | 1st Intensity | 1st S/N | 2nd Intensity | 2nd S/N |
|---|---|---|---|---|---|---|
| 9 | P0901 | 29 | 106.1 | 0.9 | 154.4 | 1.3 |
|  | P0902 | 30 | 170.1 | 1.5 | 140.7 | 1.2 |
|  | P0903 | 31 | 148.3 | 1.3 | 113.0 | 1.0 |
| 10 | P1102 | 32 | 118.8 | 1.0 | 86.5 | 0.7 |
|  | P1103 | 33 | 153.8 | 1.4 | 134.3 | 1.2 |
|  | P1104 | 34 | 131.3 | 1.2 | 160.1 | 1.4 |
| 11 | P2701 | 35 | 122.7 | 1.1 | 160.4 | 1.4 |
|  | P2702 | 36 | 176.1 | 1.6 | 194.9 | 1.7 |
| 12 | P2801 | 37 | 154.4 | 1.4 | 122.4 | 1.1 |
|  | P2802 | 38 | 152.4 | 1.3 | 121.9 | 1.0 |
| 13 | P3301 | 39 | 163.7 | 1.4 | 128.0 | 1.1 |
|  | P3302 | 40 | 137.0 | 1.2 | 108.7 | 0.9 |
| 14 | P2901 | 41 | 157.3 | 1.4 | 159.0 | 1.4 |
|  | P2902 | 42 | 178.3 | 1.6 | 132.3 | 1.1 |
|  | P2903 | 43 | 160.6 | 1.4 | 122.4 | 1.1 |
| 15 | P3001 | 44 | 127.7 | 1.1 | 140.7 | 1.2 |
|  | P3002 | 45 | 116.8 | 1.0 | 161.5 | 1.4 |
|  | P3003 | 46 | 124.1 | 1.1 | 156.5 | 1.3 |
| 16 | P1901 | 47 | 131.8 | 1.2 | 111.3 | 1.0 |
|  | P1902 | 48 | 160.6 | 1.4 | 118.2 | 1.0 |
|  | P1903 | 49 | 733.0 | 6.5 | 646.8 | 5.5 |
|  | P1904 | 50 | 168.4 | 1.5 | 121.5 | 1.0 |
| 17 | P2001 | 51 | 115.1 | 1.0 | 90.7 | 0.8 |
|  | P2002 | 52 | 173.4 | 1.5 | 138.5 | 1.2 |
| 18 | P2105 | 53 | 134.0 | 1.2 | 176.9 | 1.5 |
|  | P2102 | 54 | 143.0 | 1.3 | 254.1 | 2.2 |
|  | P2103 | 55 | 223.6 | 2.0 | 140.1 | 1.2 |

TABLE 88

*Trichophyton interdigitale*

| Group | Probe Name | SEQ ID No: | 1st Intensity | 1st S/N | 2nd Intensity | 2nd S/N |
|---|---|---|---|---|---|---|
| 19 | P2205 | 56 | 175.5 | 1.5 | 148.6 | 1.3 |
|  | P2202 | 57 | 180.3 | 1.6 | 169.4 | 1.5 |
|  | P2203 | 58 | 348.8 | 3.1 | 318.0 | 2.7 |
|  | P2204 | 59 | 127.0 | 1.1 | 117.7 | 1.0 |
| 20 | P2302 | 60 | 416.2 | 3.7 | 424.7 | 3.6 |
|  | P2306 | 61 | 176.8 | 1.6 | 207.2 | 1.8 |
|  | P2305 | 62 | 205.1 | 1.8 | 269.3 | 2.3 |
| 21 | P2405 | 63 | 155.1 | 1.4 | 141.7 | 1.2 |
|  | P2402 | 64 | 3126.5 | 27.6 | 2376.3 | 20.4 |
|  | P2403 | 65 | 201.0 | 1.8 | 260.6 | 2.2 |
| 22 | P2501 | 66 | 302.2 | 2.7 | 228.1 | 2.0 |
|  | P2502 | 67 | 793.9 | 7.0 | 1017.4 | 8.7 |
| 23 | P2604 | 68 | 131.7 | 1.2 | 186.1 | 1.6 |
|  | P2601 | 69 | 132.1 | 1.2 | 164.4 | 1.4 |
| 24 | P3101 | 70 | 141.7 | 1.3 | 129.3 | 1.1 |
|  | P3102 | 71 | 6558.1 | 57.9 | 7037.3 | 60.4 |
| 25 | P3201 | 72 | 286.6 | 2.5 | 231.4 | 2.0 |
|  | P3202 | 73 | 131.4 | 1.2 | 96.5 | 0.8 |
| 26 | P3401 | 74 | 6545.0 | 57.8 | 8535.7 | 73.2 |
|  | P3402 | 75 | 31173.9 | 275.3 | 35787.2 | 307.0 |
| 27 | Ptricho1 | 76 | 5583.2 | 49.3 | 6475.3 | 55.6 |
| 28 | Pfila1 | 77 | 47651.6 | 420.8 | 48016.3 | 411.9 |
| 29 | Pfungi1 | 78 | 22274.5 | 196.7 | 29041.4 | 249.1 |
|  | Pfungi2 | 79 | 18990.5 | 167.7 | 23047.2 | 197.7 |
|  | Pfungi3 | 80 | 22259.4 | 196.6 | 27115.2 | 232.6 |

The results of Tables 11 to 88 demonstrate that the 80 probes exhibit their respective distinctly characteristic patterns of fluorescence intensity in the experiment results for each fungus. Such a pattern of fluorescence intensity of each probe distinctive of each fungus is hereinafter referred to as an "intensity profile for each fungus". The intensity profile well conserves the characteristic pattern of fluorescence intensity of the probe in experiments other than those shown in the present Example, even when the absolute value of fluorescence intensity differs among the experiments. Specifically, it was demonstrated that the intensity profile is conserved for each fungal species.

In conclusion, the use of a carrier in which the probe sets described in the present Example are immobilized gives a fluorescence intensity profile distinctive of each fungus after hybridization and permits fungal species identification.

Specifically, a DNA chip could be prepared in which a probe set capable of specifically detecting only each fungus to be detected in a specimen was immobilized. Furthermore, the use of this DNA chip enabled identification of a pathogen of infection and solved problems associated with microorganism-derived DNA probes. Specifically, oligonucleotide probes can be synthesized chemically in large amounts and can be purified or controlled in terms of concentrations. Moreover, a probe set intended for fungal species classification could be provided which is capable of collectively detecting the same fungal species and detecting different fungal species in distinction from each other. According to the embodiment, the presence of a pathogen of infection can be determined efficiently and with high precision by detecting in just proportion the ITS region nucleotide sequence of DNA of the pathogen of infection.

As described above, a nucleic acid contained in a specimen is amplified based on a common region and hybridized with fungus-specific probes. This method enabled rapid and convenient identification of a fungal species.

Example 2

Identification of Causative Fungus of Nail Disease

DNA is directly extracted without culture from a nail disease-affected area and used for identifying a causative fungal species thereof.

1. Specimen Collection

Nail specimens were collected from the affected areas of patients who gave informed consent, of patients who visited dermatology.

These nail specimens are divided into two groups, one of which is subjected to identification by culture according to a standard method, and the other of which is subjected to identification by the method described in the present invention.

2. Pretreatment

DNA was amplified after extraction using the primers shown in Table 2 in the same way as in Example 1. In this context, obvious nucleic acid amplification was observed, demonstrating the presence of some fungus in the nail specimens.

The amplification products were labeled using the primer for labeling shown in Table 8 and then subjected to hybridization reaction and fluorescence measurement.

Fluorescence intensities obtained by the fluorescence measurement are shown in Tables 89 to 91 below. The fluorescence intensity described in Tables 89 to 91 is an average value of results of the same experiments performed 3 times. Tables 89 to 91 also shows intensities obtained by hybridization using a fungus-free negative control.

TABLE 89

Hybridization results of nucleic acid obtained from specimen

| Group | Probe Name | SEQ ID No: | Fluorescence Intensity Analyte (average value of n = 3) | Control |
|---|---|---|---|---|
| 1 | P0101 | 1 | 73.7 | 72.1 |
|  | P0102 | 2 | 69.4 | 75.3 |
|  | P0103 | 3 | 77.5 | 75.5 |
|  | P0104 | 4 | 69.9 | 73.3 |
| 2 | P0201 | 5 | 67.5 | 73.8 |
|  | P0202 | 6 | 67.4 | 72.7 |
|  | P0204 | 7 | 215.7 | 74.8 |
|  | P0205 | 8 | 68.9 | 71.7 |
| 3 | P0302 | 9 | 69.3 | 76.4 |
|  | P0303 | 10 | 69.9 | 74.8 |
|  | P0304 | 11 | 73.3 | 74.5 |
|  | P0305 | 12 | 68.1 | 74.5 |
| 4 | P0401 | 13 | 70.5 | 73.4 |
|  | P0402 | 14 | 70.3 | 73.2 |
|  | P0403 | 15 | 74.8 | 73.8 |
|  | P0404 | 16 | 69.8 | 75.2 |
| 5 | P0503 | 17 | 67.9 | 74.2 |
|  | P0502 | 18 | 65.6 | 72.8 |
| 6 | P0601 | 19 | 69.2 | 75.4 |
|  | P0602 | 20 | 70.1 | 74.0 |
|  | P0603 | 21 | 71.7 | 73.5 |
|  | P0604 | 22 | 67.4 | 72.6 |
| 7 | P0701 | 23 | 70.2 | 75.2 |
|  | P0702 | 24 | 216.4 | 75.1 |
|  | P0703 | 25 | 69.2 | 71.6 |
|  | P0704 | 26 | 70.8 | 72.4 |
| 8 | P0801 | 27 | 69.2 | 72.8 |
|  | P0803 | 28 | 69.6 | 74.6 |

TABLE 90

Hybridization results of nucleic acid obtained from specimen

| Group | Probe Name | SEQ ID No: | Fluorescence Intensity Analyte (average value of n = 3) | Control |
|---|---|---|---|---|
| 9 | P0901 | 29 | 72.7 | 73.9 |
|  | P0902 | 30 | 70.5 | 73.8 |
|  | P0903 | 31 | 69.2 | 72.7 |
| 10 | P1102 | 32 | 68.7 | 71.8 |
|  | P1103 | 33 | 70.4 | 74.8 |
|  | P1104 | 34 | 78.0 | 75.8 |
| 11 | P2701 | 35 | 74.3 | 73.6 |
|  | P2702 | 36 | 80.7 | 72.6 |
| 12 | P2801 | 37 | 72.5 | 74.3 |
|  | P2802 | 38 | 71.2 | 73.2 |
| 13 | P3301 | 39 | 111.2 | 72.4 |
|  | P3302 | 40 | 70.0 | 74.1 |
| 14 | P2901 | 41 | 92.9 | 73.4 |
|  | P2902 | 42 | 73.6 | 75.4 |
|  | P2903 | 43 | 71.0 | 74.2 |
| 15 | P3001 | 44 | 77.4 | 74.8 |
|  | P3002 | 45 | 108.9 | 74.2 |
|  | P3003 | 46 | 72.2 | 74.9 |
| 16 | P1901 | 47 | 71.9 | 74.8 |
|  | P1902 | 48 | 72.1 | 73.3 |
|  | P1903 | 49 | 69.4 | 73.6 |
|  | P1904 | 50 | 72.2 | 73.7 |
| 17 | P2001 | 51 | 80.4 | 72.1 |
|  | P2002 | 52 | 71.2 | 73.4 |
| 18 | P2105 | 53 | 81.1 | 75.9 |
|  | P2102 | 54 | 79.9 | 73.0 |
|  | P2103 | 55 | 71.7 | 73.9 |

TABLE 91

Hybridization results of nucleic acid obtained from specimen

| Group | Probe Name | SEQ ID No: | Fluorescence Intensity Analyte (average value of n = 3) | Control |
|---|---|---|---|---|
| 19 | P2205 | 56 | 82.2 | 74.8 |
|  | P2202 | 57 | 71.7 | 74.6 |
|  | P2203 | 58 | 164.9 | 71.1 |
|  | P2204 | 59 | 68.8 | 73.2 |
| 20 | P2302 | 60 | 15036.1 | 75.3 |
|  | P2306 | 61 | 399.1 | 73.0 |
|  | P2305 | 62 | 10349.6 | 73.5 |
| 21 | P2405 | 63 | 72.0 | 73.9 |
|  | P2402 | 64 | 1104.3 | 73.9 |
|  | P2403 | 65 | 119.1 | 73.2 |
| 22 | P2501 | 66 | 94.1 | 73.4 |
|  | P2502 | 67 | 3190.5 | 72.5 |
| 23 | P2604 | 68 | 268.0 | 74.1 |
|  | P2601 | 69 | 270.4 | 74.5 |
| 24 | P3101 | 70 | 71.0 | 73.6 |
|  | P3102 | 71 | 71.3 | 74.3 |
| 25 | P3201 | 72 | 70.9 | 75.6 |
|  | P3202 | 73 | 67.2 | 75.8 |
| 26 | P3401 | 74 | 71.5 | 74.6 |
|  | P3402 | 75 | 95.2 | 72.7 |
| 27 | Ptricho1 | 76 | 12445.6 | 72.1 |
| 28 | Pfila1 | 77 | 42101.3 | 73.3 |
| 29 | Pfungi1 | 78 | 18941.1 | 72.4 |
|  | Pfungi2 | 79 | 15137.9 | 73.8 |
|  | Pfungi3 | 80 | 21536.4 | 74.0 |

3. Analysis of Fluorescence Measurement Results 3-1. Identification of Characteristic Probe A null hypothesis below was made about the fluorescence intensity of each probe shown in Tables 89 to 91. "Null hypothesis: variations in fluorescence intensities obtained by the hybridization of the specimen-derived nucleic acids are not different from variations in fluorescence intensities obtained using the negative controls." Based on this null hypothesis, the student T test was conducted at a significance level of 0.05. As a result of the T test, a P value was 0.01368. According to this test, which was conducted at a significance level of 0.05, the null hypothesis was rejected. Specifically, the results demonstrated that variations in fluorescence intensities obtained by the hybridization of the specimen-derived nucleic acids are significantly different from variations in fluorescence intensities obtained using the negative controls.

In this context, the fluorescence intensities obtained by the hybridization of the specimen-derived nucleic acids have significant variations. Therefore, probes that give particularly large variations are selected.

The average intensity of all the probes for the specimen-derived nucleic acids shown in Tables 89 to 91 is 1827.9, and the standard deviation thereof is 6220.9. Probes that exhibited significantly high fluorescence intensity outside the average+ standard deviation are shown in Table 92 below.

TABLE 92

Probe that had significantly high intensity

| Group | Fungal Name | Probe Name | Fluorescence Intensity |
|---|---|---|---|
| 20 | Trichophyton rubrum | P2302 | 15036.1 |
|  |  | P2305 | 10349.6 |
| 27 | Common to Trichophyton | Ptricho1 | 12445.6 |
| 28 | Common to Filamentous Fungi | Pfila1 | 42101.3 |

TABLE 92-continued

Probe that had significantly high intensity

| Group | Fungal Name | Probe Name | Fluorescence Intensity |
|---|---|---|---|
| 29 | Common to Fungi | Pfungi1 | 18941.1 |
|  |  | Pfungi2 | 15137.9 |
|  |  | Pfungi3 | 21536.4 |

3-2. Comparison with Intensity Profile of Model Specimen

The intensity profile for each of 26 fungal species could be obtained by this DNA chip in (Example 1). This intensity profile for each fungus was compared with an intensity profile obtained from the clinical specimens used in the present Example to determine a fungus most similar in intensity profile characteristics to the fungus in the specimens. As a result, it was demonstrated that *Trichophyton rubrum* was very similar in intensity pattern thereto.

4. Fungal Species Identification

From the results of Table 92 shown in the paragraph '3-1. Identification of characteristic probe' or the results of comparison with the intensity patterns of model fungi shown in the paragraph '3-2. Comparison with intensity profile of model specimen', it was concluded that the fungus present in the nail specimens collected in the paragraph '1. Specimen collection' is *Trichophyton rubrum*.

As a result of culture for approximately 4 weeks, it was also concluded that the fungus present in the nail specimens is *Trichophyton rubrum*. The method of the present invention does not require a period as long as 4 weeks and achieved more rapid identification of a fungal species than that by culture.

A conventional PCR kit capable of specifically amplifying a nucleic acid derived from each organism species may be used without the use of the method of the present invention. In such a case, the PCR kit requires preparing primer sets according to the number of candidate fungal species such primer sets for 26 fungi are prepared for 26 candidate fungal species, as in this experiment. In this case, amplification operation must be performed 26 times, and very complicated procedures are necessary.

As described above, a nucleic acid contained in a specimen collected from a nail as an affected area is amplified based on a common region and hybridized with fungus-specific probes. This method achieved more rapid identification of a fungal species than the conventional identification method.

In the present Example, the identification of *Trichophyton rubrum* in nail specimens is described as an example. The same results are obtained for specimens other than nails, such as hair or skin slices. Moreover, the same detection can be conducted on fungi other than *Trichophyton rubrum* in specimens.

Example 3

Identification of Causative Fungi of Nail Disease (Identification of Plural Fungal Species)

In the present Example, the extraction of plural fungi from a nail will be described as an example.

1. Hybridization

The amplification and hybridization of DNA extracted from a nail were performed in the same way as in the method shown in (Example 2). As a result, fluorescence intensities shown in Tables 93 to 95 below were obtained. The fluorescence intensity shown in Tables 93 to 95 is a mean value of results of experiments performed 9 times using DNA extracted from the same specimen.

TABLE 93

| Group | Probe Name | Fluorescence Intensity |
|---|---|---|
| 1 | P0101 | 246.4 |
|  | P0102 | 482.2 |
|  | P0103 | 587.7 |
|  | P0104 | 47.9 |
| 2 | P0201 | 47.9 |
|  | P0202 | 47.7 |
|  | P0204 | 287.8 |
|  | P0205 | 46.3 |
| 3 | P0302 | 46.0 |
|  | P0303 | 48.3 |
|  | P0304 | 46.2 |
|  | P0305 | 45.6 |
| 4 | P0401 | 463.6 |
|  | P0402 | 2601.0 |
|  | P0403 | 3486.9 |
|  | P0404 | 4171.6 |
| 5 | P0503 | 46.2 |
|  | P0502 | 46.3 |
| 6 | P0601 | 44.4 |
|  | P0602 | 46.0 |
|  | P0603 | 48.0 |
|  | P0604 | 46.3 |
| 7 | P0701 | 45.1 |
|  | P0702 | 91.7 |
|  | P0703 | 44.2 |
|  | P0704 | 45.3 |
| 8 | P0801 | 46.1 |
|  | P0803 | 46.1 |
| 9 | P0901 | 387.8 |
|  | P0902 | 737.9 |
|  | P0903 | 2294.4 |

TABLE 94

| Group | Probe Name | Fluorescence Intensity |
|---|---|---|
| 10 | P1102 | 49.1 |
|  | P1103 | 51.4 |
|  | P1104 | 48.5 |
| 11 | P2701 | 210.0 |
|  | P2702 | 47.5 |
| 12 | P2801 | 46.7 |
|  | P2802 | 44.4 |
| 13 | P3301 | 165.1 |
|  | P3302 | 46.8 |
| 14 | P2901 | 45.0 |
|  | P2902 | 42.9 |
|  | P2903 | 45.6 |
| 15 | P3001 | 46.8 |
|  | P3002 | 44.7 |
|  | P3003 | 45.0 |
| 16 | P1901 | 45.3 |
|  | P1902 | 45.7 |
|  | P1903 | 47.0 |
|  | P1904 | 46.1 |
| 17 | P2001 | 49.7 |
|  | P2002 | 44.9 |
| 18 | P2105 | 46.2 |
|  | P2102 | 52.3 |
|  | P2103 | 45.3 |
| 19 | P2205 | 57.3 |
|  | P2202 | 47.2 |
|  | P2203 | 95.6 |
|  | P2204 | 45.4 |
| 20 | P2302 | 7410.5 |
|  | P2306 | 236.4 |
|  | P2305 | 5837.7 |

TABLE 95

| Group | Probe Name | Fluorescence Intensity |
|---|---|---|
| 21 | P2405 | 43.8 |
|  | P2402 | 805.0 |
|  | P2403 | 72.8 |
| 22 | P2501 | 60.5 |
|  | P2502 | 2604.4 |
| 23 | P2604 | 117.2 |
|  | P2601 | 102.1 |
| 24 | P3101 | 45.1 |
|  | P3102 | 47.5 |
| 25 | P3201 | 43.4 |
|  | P3202 | 44.7 |
| 26 | P3401 | 45.6 |
|  | P3402 | 56.7 |
| 27 | Ptricho1 | 8215.4 |
| 28 | Pfila1 | 23049.3 |
| 29 | Pfungi1 | 11344.7 |
|  | Pfungi2 | 10296.1 |
|  | Pfungi3 | 11586.3 |

The average of spot intensities obtained using negative controls in this experiment was 49.2, and the standard deviation thereof was 18.7.

2. Fungal Species Determination

To determine fungal species from the hybridization results, software was prepared in which determination logic was incorporated.

2-1. Determination Software

Figure 6:
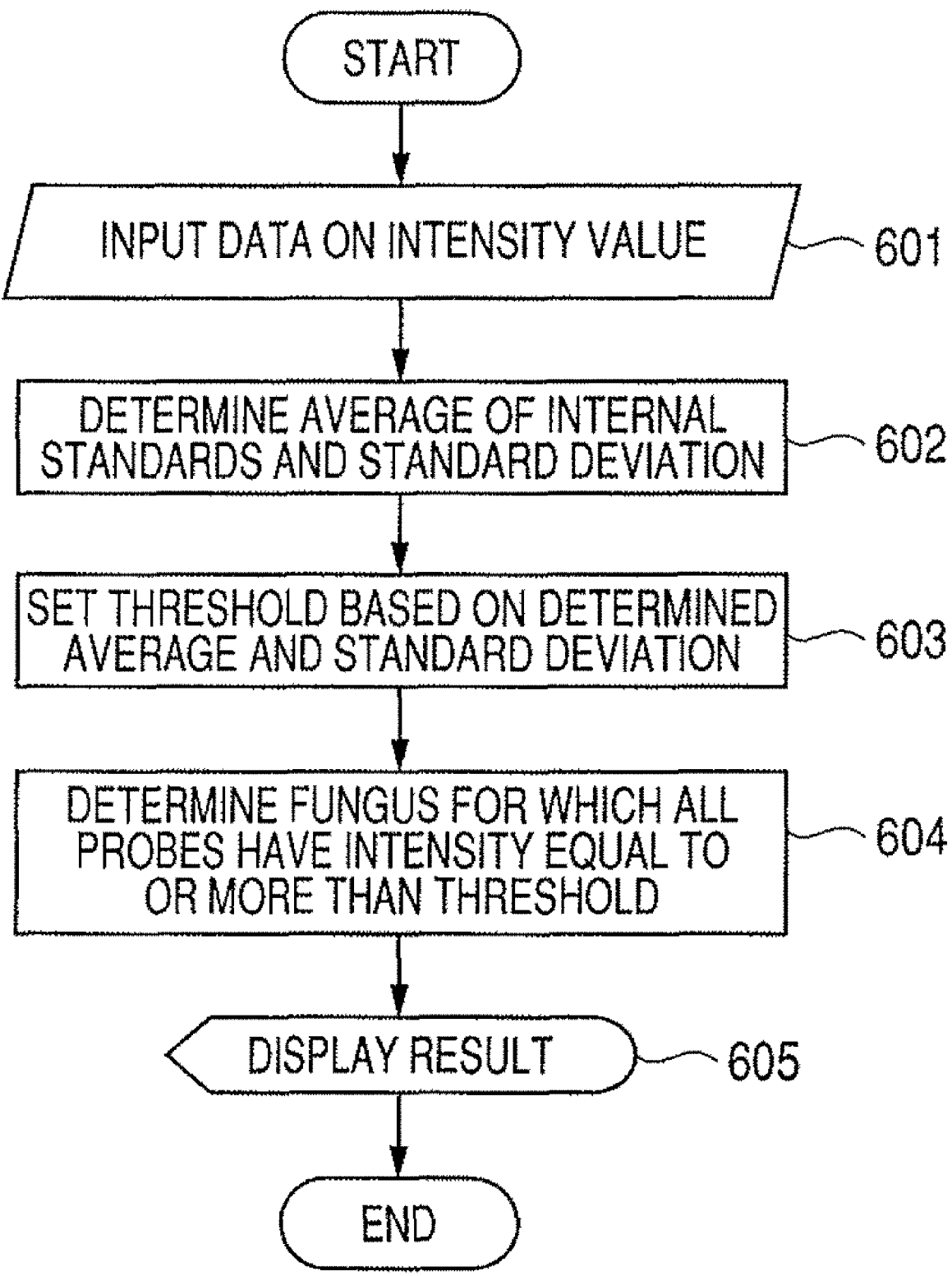
FIG. 6 is a flow chart illustrating fungal species determi-
nation logic, in which 601 is a step of inputting data on
intensity value; 602 is a step of analyzing intensity value for
determination; 603 is a step of determining threshold for
determination; 604 is a step of extracting fungus for which
probes have significantly high intensity; and 605 is a step of
displaying determination result.

Determination software in which logic shown in FIG. 6 was incorporated was prepared as determination software. In a step 601, data including hybridization intensity is input. In a step 602, an average value and standard deviation thereof are determined from the data of negative controls. In a step 603, a threshold for determining whether the fluorescence intensity of each spot is significantly high is determined from the average value of spots of negative controls and the standard deviation. In the present Example, a value obtained by adding the tripled standard deviation to the average value is defined as a threshold. A spot that has high intensity exceeding this threshold is determined as a spot in which hybridization significantly occurs. In the DNA chip of the present Example, two to four probes are designed for each fungus. In a step 604, a fungus for which all probes have intensity exceeding the threshold is extracted. In a step 605, the name of a fungus for which significantly strong hybridization reaction occurs as a result is displayed.

2-2. Fungal Species Determination

The determination software was used by inputting the hybridization results shown in Tables 93 to 95.

As a result, three fungi shown in Table 96 below could be extracted as fungi that gave significantly high intensity.

TABLE 96

| Determination results ||||
|---|---|---|---|
| Group | Fungal Name | Probe Name | Intensity |
| 4 | *Candida guilliermondii* | P0401 | 463.6 |
|  |  | P0402 | 2601.0 |
|  |  | P0403 | 3486.9 |
|  |  | P0404 | 4171.6 |
| 9 | *Candida parapsilosis* | P0901 | 387.8 |
|  |  | P0902 | 737.9 |
|  |  | P0903 | 2294.4 |
| 20 | *Trichophyton rubrum* | P2302 | 7410.5 |
|  |  | P2306 | 236.4 |
|  |  | P2305 | 5837.7 |
| 27 | Common to Trichophyton | Ptricho1 | 8215.4 |
| 28 | Common to Filamentous Fungi | Pfila1 | 23049.3 |

TABLE 96-continued

Determination results

| Group | Fungal Name | Probe Name | Intensity |
|---|---|---|---|
| 29 | Common to Fungi | Pfungi1 | 11344.7 |
| | | Pfungi2 | 10296.1 |
| | | Pfungi3 | 11586.3 |

In an experiment using negative controls, such a probe that had significantly high intensity was not detected. Thus, it was determined that the specimen in the present Example contains "*Candida guilliermondii*", "*Candida parapsilosis*", and "*Trichophyton rubrum*".

As a result of comparison with the intensity profile for each fungus obtained in (Example 1), it was demonstrated that the fungi in the specimen are not similar to any fungus in terms of a single intensity profile. Comparison also involving intensity profiles for these three fungi demonstrated that the fungi in the specimen are similar to these three fungi. Accordingly, it was demonstrated that a method for determining fungi from similar profiles using the previously obtained intensity profile as dictionary data is also effective.

3. Comparison with Culture Result

As a result of culturing the specimen in the present Example, the growth of "*Trichophyton rubrum*" was confirmed. In terms of fluorescence intensity, *Candida guilliermondii* and *Candida parapsilosis* give lower intensity than that of *Trichophyton rubrum*, suggesting that in terms of a quantitative ratio among the fungi, *Trichophyton rubrum* is contained in the largest amounts. This suggests that the growth of the fungi other than *Trichophyton rubrum* was not confirmed because of the quantitative ratio among the fungi. From these results, it can be concluded that the method for identifying a fungal species according to the present invention has higher sensitivity than the conventional culture method.

The present invention is not limited to the above embodiments and various changes and modifications can be made within the spirit and scope of the present invention. Therefore to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-128664, filed May 14, 2007, which is hereby incorporated by reference herein in its entirety.

What is claimed is:

1. A method for identifying a fungal species, comprising:
extracting a nucleic acid from an affected tissue;
amplifying the extracted nucleic acid using a primer set capable of amplifying at least a portion of an ITS region of fungi; and
obtaining information about a partial sequence of the amplified nucleic acid which permits fungal species identification and determining and identifying a fungal species of the amplified nucleic acid,
wherein the fungal species of the amplified nucleic acid is determined and identified by using a probe set comprising a plurality of nucleic acid probes, at least one of which is designed from a partial sequence specific to the fungal species of the amplified nucleic acid,
wherein a hybridization reaction is performed with the at least one of the plurality of nucleic acid probes, and the fungal species of the amplified nucleic acid is determined and identified from a signal intensity obtained from the hybridization reaction, and
wherein the plurality of nucleic acid probes comprises:
(1) a first probe belonging to any group selected from the following groups 1 to 29 and a second probe belonging to any group selected from the following groups 1 to 29 and not belonging to the group to which the first probe belongs, or
(2) a third probe consisting of the complementary sequence of the first probe and a fourth probe consisting of the complementary sequence of the second probe:

group 1:
(1) a probe consisting of tctttgaaacaaacttgctttggcgg (SEQ ID NO: 1),
(2) a probe consisting of ccgccagaggtctaaacttacaacc (SEQ ID NO: 2),
(3) a probe consisting of gacggtagtggtaaggcgggat (SEQ ID NO: 3), and
(4) a probe consisting of ggcggtaacgtccaccacgtat (SEQ ID NO: 4), group 2:
(1) a probe consisting of tgtgttttgttctggacaaacttgctttg (SEQ ID NO: 5),
(2) a probe consisting of ctgccgccagaggacataaacttac (SEQ ID NO: 6),
(3) a probe consisting of tagtggtataaggcggagatgcttga (SEQ ID NO: 7), and
(4) a probe consisting of tctggcgtcgcccattttattcttc (SEQ ID NO: 8), group 3:
(1) a probe consisting of ggtgttttatcacacgactcgacact (SEQ ID NO: 9),
(2) a probe consisting of ggagttctcccagtggatgcaaac (SEQ ID NO: 10),
(3) a probe consisting of ggccatatcagtatgtgggacacg (SEQ ID NO: 11), and
(4) a probe consisting of aggttttaccaactcggtgttgatctag (SEQ ID NO: 12), group 4:
(1) a probe consisting of gcttaactgcgcggcgaaaaac (SEQ ID NO: 13),
(2) a probe consisting of agataggttgggccagaggtttaaca (SEQ ID NO: 14),
(3) a probe consisting of tcttagtcggactaggcgtttgctt (SEQ ID NO: 15), and
(4) probe consisting of tcgttgaatggtgtggcggat (SEQ ID NO: 16), group 5:
(1) a probe consisting of gtgttgccttccgaaatatcacagttg (SEQ ID NO: 17), and
(2) a probe consisting of cagttgtcgcaatacgttacttcaacttt (SEQ ID NO: 18), group 6:
(1) a probe consisting of gcggccagttcttgattctctgc (SEQ ID NO: 19),
(2) a probe consisting of agctcgtctctccagtggacataaac (SEQ ID NO: 20),
(3) a probe consisting of ttgaaagtggctagccgttgcc (SEQ ID NO: 21), and
(4) consisting of tcgtggtaagcttgggtcatagagac (SEQ ID NO: 22), group 7:
(1) a probe consisting of agcggaacgaaaacaacaacacct (SEQ ID NO: 23),
(2) a probe consisting of acctagtgtgaattgcagccatcg (SEQ ID NO: 24),
(3) a probe consisting of gacgtgtaaagagcgtcggagc (SEQ ID NO: 25), and
(4) a probe consisting of gcgagtgttgcgagacaacaaaaag (SEQ ID NO: 26), group 8:
(2) a probe consisting of aggcgttgctccgaaatatcaacc (SEQ ID NO: 28), group 9:
(1) a probe consisting of tggggcctgccagagattaaact (SEQ ID NO: 29),
(2) a probe consisting of gtgttgagcgatacgctgggttt (SEQ ID NO: 30), and
(3) a probe consisting of gtttttccactcattggtacaaactcca (SEQ ID NO: 31), group 10:
(1) a probe consisting of accgccagaggttataactaaaccaaa (SEQ ID NO: 32),
(2) a probe consisting of gagcaatacgctaggtttgtttgaaagaa (SEQ ID NO: 33), and
(3) a probe consisting of acgcttattttgctagtggccacc (SEQ ID NO: 34), group 11:
(1) a probe consisting of tgaactgttgattgacttcggtcaattga (SEQ ID NO: 35), and
(2) a probe consisting of gcgtgtttaacttgtcttatctggcg (SEQ ID NO: 36), group 12:
(1) a probe consisting of gttctactacttgacgcaagtcgagt (SEQ ID NO: 37), and
(2) a probe consisting of ttgggcgtctgcgatttctgatc (SEQ ID NO: 38), group 13:
(1) a probe consisting of caacggatctcttggcttccaca (SEQ ID NO: 39), and
(2) a probe consisting of ttgagagtcatgaaaatctcaatccctcg (SEQ ID NO: 40), group 14:
(1) a probe consisting of cccgtgtctatcgtaccttgttgc (SEQ ID NO: 41),
(2) a probe consisting of tgaacgctgttctgaaagtatgcagt (SEQ ID NO: 42), and
(3) a probe consisting of gccagccgacacccaactttatt (SEQ ID NO: 43), group 15:
(1) a probe consisting of cccatccgtgtctattgtaccctgt (SEQ ID NO: 44),
(2) a probe consisting of acacgaacactgtctgaaagcgtg (SEQ ID NO: 45), and (3) a probe consisting of cctgccgacgttttccaaccat (SEQ ID NO: 46), group 16:
(1) a probe consisting of tctctctgaatgctggacggtgtc (SEQ ID NO: 47),
(2) a probe consisting of ctcgccgaaggagtgattctcaga (SEQ ID NO: 48),
(3) a probe consisting of ttccaccgggagaggagaaagg (SEQ ID NO: 49), and
(4) a probe consisting of acaaaaccagcgccttcaggac (SEQ ID NO: 50), group 17:
(2) a probe consisting of cgccggaggattactctggaaaac (SEQ ID NO: 52), group 18:
(1) a probe consisting of gtccggggacaatcaactccct (SEQ ID NO: 53),
(2) a probe consisting of aatccatgaatactgttccgtctgagc (SEQ ID NO: 54), and
(3) a probe consisting of ggccggttttctggcctagtttt (SEQ ID NO: 55), group 19:
(1) a probe consisting of agcctctttgggggctttagct (SEQ ID NO: 56),
(2) a probe consisting of acagacatcaaaaaatcttggaaagctgt (SEQ ID NO: 57),
(3) a probe consisting of ctgggcgaatgggcagtcaaac (SEQ ID NO: 58), and
(4) a probe consisting of ctctggccttcccccaaatctc (SEQ ID NO: 59), group 20:
(1) a probe consisting of agacaccaagaaaaattctctgaagage (SEQ ID NO: 60),
(2) a probe consisting of gaatgggcagccaattcagcgc (SEQ ID NO: 61), and
(3) a probe consisting of cttctgggagcctcgagccg (SEQ ID NO: 62), group 21:
(1) a probe consisting of cggcgagcctctctttatagcg (SEQ ID NO: 63),
(2) a probe consisting of cctctctttatagcggctcaacgc (SEQ ID NO: 64), and
(3) a probe consisting of ggctttctaggcgaatgggcaa (SEQ ID NO: 65), group 22:
(1) a probe consisting of aggacagacatcaaaaaatcttgaagagc (SEQ ID NO: 66), and
(2) a probe consisting of aagctcggcttgtgtgatggac (SEQ ID NO: 67), group 23:
(1) a probe consisting of acaccaaggaaaattctctgaagggc (SEQ ID NO: 68), and
(2) a probe consisting of ccaaggaaaattctctgaagggctgt (SEQ ID NO: 69), group 24:
(1) a probe consisting of tctctttagtggctcaacgctgga (SEQ ID NO: 70), and
(2) a probe consisting of ggacagacgcaaaaaattctttcagaag (SEQ ID NO: 71), group 25:
(1) a probe consisting of tgggcaataaccagcgcctcta (SEQ ID NO: 72), and
(2) a probe consisting of tcagggatgcatttctctgcgaatc (SEQ ID NO: 73), group 26:
(1) a probe consisting of cctctctttagtggctaaacgctgg (SEQ ID NO: 74), and
(2) a probe consisting of cgccctggcctcaaaatctgtt (SEQ ID NO: 75), group 27:
(1) a probe consisting of ttcgagcgtcatttcaacccctc (SEQ ID NO: 76), group 28:
(1) a probe consisting of gttgacctcggatcaggtagggat (SEQ ID NO: 77), and group 29:
(1) a probe consisting of aactttcaacaacggatctcttggttct (SEQ ID NO: 78),
(2) a probe consisting of gcatcgatgaagaacgcagcga (SEQ ID NO: 79)), and
(3) a probe consisting of gtgaatcatcgaatctttgaacgcaca (SEQ ID NO: 80).

2. The method for identifying a fungal species according to claim 1, wherein the amplifying of the extracted nucleic acid is performed using PCR.

3. The method for identifying a fungal species according to claim 1, wherein each of the plurality of nucleic acid probes constituting the probe set is designed from the partial sequence.

4. The method for identifying a fungal species according to claim 1, wherein the plurality of nucleic acid probes constituting the probe set are designed from partial sequences respectively specific to plural fungal species, and the probe set is immobilized on a carrier.

5. The method for identifying a fungal species according to claim 3, wherein the plurality of nucleic acid probes constituting the probe set are arranged at a distance from each other on a carrier.

6. The method for identifying a fungal species according to claim 3, wherein each of the plurality of nucleic acid probes constituting the probe set meets hybridization conditions suitable to determining and identifying the fungal species of the amplified nucleic acid.

7. The method for identifying a fungal species according to claim 3, wherein the plurality of nucleic acid probes constituting the probe set are designed to have a melting temperature falling within a predetermined range.

8. The method for identifying a fungal species according to claim 1, wherein the determining and identifying the fungal species of the amplified nucleic acid comprises using the fact that probes respectively designed for fungal species produce hybridization signal intensities different from each other.

9. A kit for performing a method for identifying a fungal species according to claim 4, comprising: the carrier on which the probe set is immobilized; and a reagent for detecting the hybridization reaction.

10. The method according to claim 1, wherein the primer set comprises ITS1 (SEQ ID NO: 81) and ITS4 (SEQ ID NO: 82).

* * * * *